(12) United States Patent
Yen

(10) Patent No.: US 9,166,177 B2
(45) Date of Patent: Oct. 20, 2015

(54) DITRIPHENYLENE DERIVATIVE AND ORGANIC ELECTROLUMINESCENT DEVICE USING THE SAME

(71) Applicant: Feng-Wen Yen, Taipei (TW)

(72) Inventor: Feng-Wen Yen, Taipei (TW)

( * ) Notice: Subject to any disclaimer, the term of this patent is extended or adjusted under 35 U.S.C. 154(b) by 381 days.

(21) Appl. No.: 13/771,105

(22) Filed: Feb. 20, 2013

(65) Prior Publication Data

US 2014/0231754 A1    Aug. 21, 2014

(51) Int. Cl.
*H01L 51/00*   (2006.01)
*C07C 255/58*   (2006.01)
(Continued)

(52) U.S. Cl.
CPC ............ *H01L 51/0074* (2013.01); *C07C 13/62* (2013.01); *C07C 211/61* (2013.01); *C07C 255/58* (2013.01); *C07D 333/08* (2013.01); *C07D 333/22* (2013.01); *C07D 409/14* (2013.01); *C09K 11/06* (2013.01); *H01L 51/0056* (2013.01); *H01L 51/0072* (2013.01); *C07C 2103/24* (2013.01); *C07C 2103/48* (2013.01); *C07C 2103/50* (2013.01); *C07C 2103/54* (2013.01); *C09K 2211/1011* (2013.01);
(Continued)

(58) Field of Classification Search
CPC ............ H01L 51/0071; H01L 51/0072; H01L 51/0074; C09K 11/06; H05B 33/14
See application file for complete search history.

(56) References Cited

U.S. PATENT DOCUMENTS 6,861,163 B2   3/2005 Cheng et al.
8,092,924 B2   1/2012 Kwong et al.
(Continued)

FOREIGN PATENT DOCUMENTS

EP   2143775        1/2010
EP   2143775 A1 *   1/2010
(Continued)

OTHER PUBLICATIONS

Journal of the American Chemical Society, vol. 130, No. 48, (2008), pp. 16435-16441.*
(Continued)

*Primary Examiner* — Dawn L. Garrett

(57) ABSTRACT

The present invention discloses a novel ditriphenylene derivative is represented by the following formula (I), the organic EL device employing the ditriphenylene derivative as host material or dopant material of emitting layer can lower driving voltage, prolong half-life time and increase the efficiency.

formula (I)

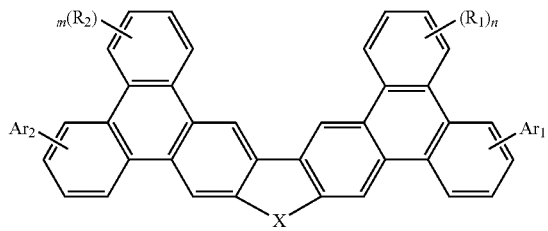

Wherein m, n represent an integer of 0 to 10. X is a divalent bridge selected from the atom or group consisting from O, S, $C(R_3)(R_4)$, $NR_5$, $Si(R_6)(R_7)$. $Ar_1$, $Ar_2$, $R_1$ to $R_7$ are substituents and the same definition as described in the present invention.

13 Claims, 3 Drawing Sheets

| 12 | — metal electrode |
| 11 | — electron injection layer |
| 10 | — electron transport layer |
| 9  | — emitting layer |
| 8  | — hole transport layer |
| 7  | — hole injection layer |
| 6  | — transparent electrode |

(51) Int. Cl.
*C07C 211/61* (2006.01)
*C07C 13/62* (2006.01)
*C09K 11/06* (2006.01)
*C07D 333/08* (2006.01)
*C07D 333/22* (2006.01)
*C07D 409/14* (2006.01)
*H01L 51/50* (2006.01)

(52) U.S. Cl.
CPC ......... *C09K 2211/185* (2013.01); *H01L 51/006* (2013.01); *H01L 51/0058* (2013.01); *H01L 51/5012* (2013.01)

(56) References Cited

U.S. PATENT DOCUMENTS

| | | | |
|---|---|---|---|
| 9,040,174 B2 * | 5/2015 | Yen et al. | 428/690 |
| 9,048,437 B2 * | 6/2015 | Yen | 1/1 |
| 2004/0076852 A1 | 4/2004 | Cheng et al. | |
| 2011/0266526 A1 | 11/2011 | Ma et al. | |

FOREIGN PATENT DOCUMENTS

| WO | 2006130598 | | 12/2006 |
|---|---|---|---|
| WO | WO 2006/130598 A2 | * | 12/2006 |
| WO | 2011137157 | | 11/2011 |
| WO | WO 2011/137157 A1 | * | 11/2011 |
| WO | 2012005362 | | 1/2012 |
| WO | WO 2012/005362 A1 | * | 1/2012 |
| WO | 2012035962 | | 3/2012 |
| WO | WO 2012/035962 A1 | * | 3/2012 |

OTHER PUBLICATIONS

Journal of Organic Chemistry, vol. 71, (2006), pp. 6822-6828.*
Journal of Physical Chemistry C, (2010), vol. 114, pp. 18702-18711.*

* cited by examiner

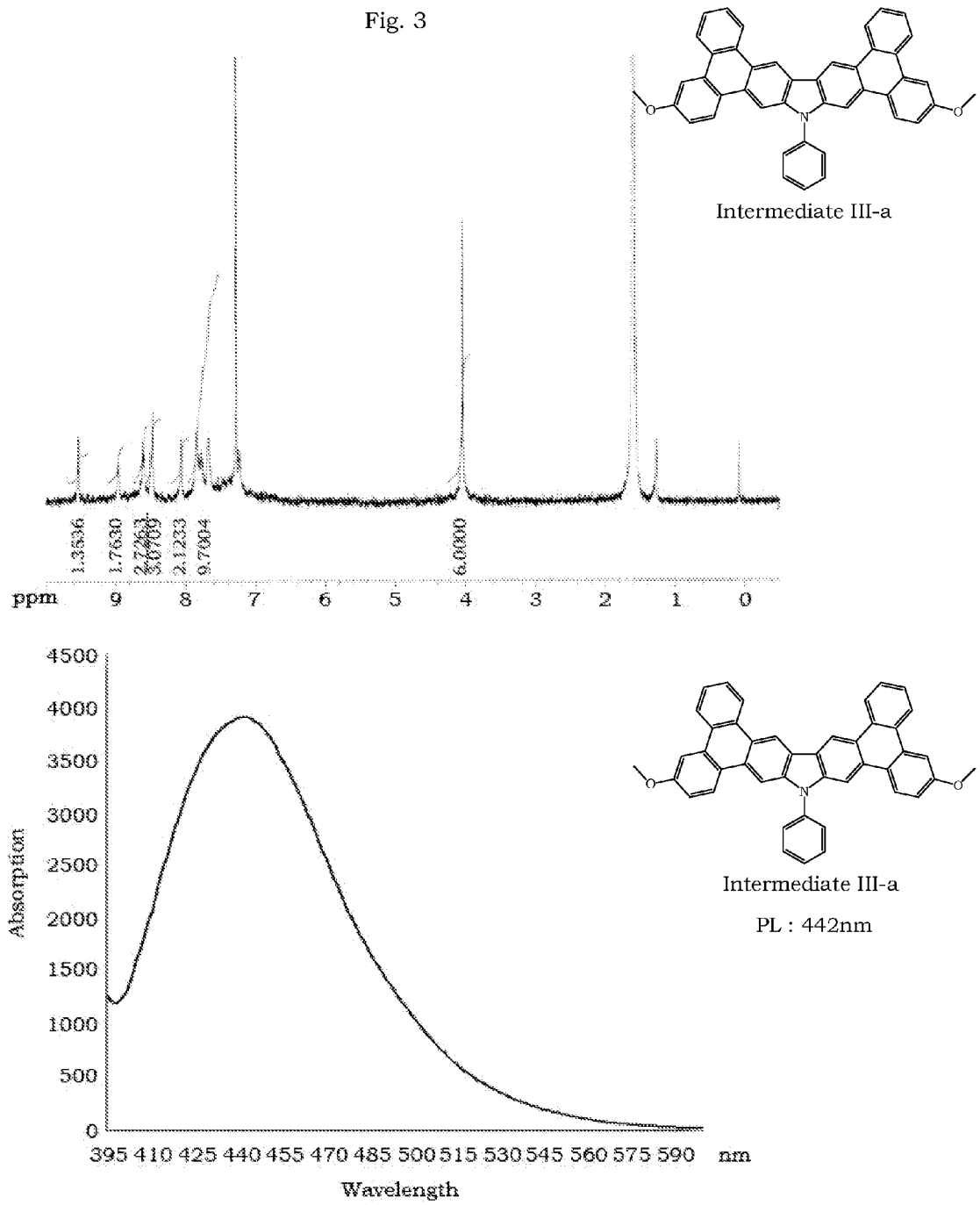

DITRIPHENYLENE DERIVATIVE AND ORGANIC ELECTROLUMINESCENT DEVICE USING THE SAME

FIELD OF INVENTION

The present invention generally relates to a novel ditriphenylene derivative and organic electroluminescent (herein referred to as organic EL) device using the ditriphenylene derivative. More specifically, the present invention relates to the ditriphenylene derivative having general formula (I), an organic EL device employing the ditriphenylene derivative as host material or dopant material of emitting layer.

BACKGROUND OF THE INVENTION

Organic EL device has many advantages such as self-emitting, wider viewing angles, faster response speeds and highly luminescence. Their simpler fabrication and capable of giving clear display comparable with LCD can make organic EL device an industry display of choice. Organic EL device contains emitting materials which are arranged between a cathode and an anode, when an applied driving voltage to be added, an electron and a hole were injected into the emitting layer and recombined to form an exciton. The exciton which results from an electron and a hole of recombination have a singlet spin state or triplet spin state. Luminescence from a singlet spin state emits fluorescence and luminescence from triplet spin state emits phosphorescence.

Organic EL device are generally composed of functionally divided organic multi-layers, e.g. hole injection layer (HIL), hole transporting layer (HTL), emitting layer (EML), electron transporting layer (ETL) and electron injection layer (EIL) and so on. For full-colored flat panel displays in AMOLED, the organic compounds used for the organic multi-layer are still unsatisfactory in half-life time, power consumption and emitting colour. Especially for AMOLED, except prolong half-life time, deep blue emission (CIE y coordinates under 0.15) is necessary for improvement.

The triphenylene skeleton based derivatives disclosed in U.S. Patent No. 20040076852A1, WO2006130598A3, EP2143775A1, U.S. Patent No. 20110266526A1, WO2011137157A1, WO2012005362A1 and WO2012035962A1 used for organic EL device are described. The present invention disclose a novel ditriphenylene skeleton based derivative having general formula (I), used as host material or dopant material of emitting layer have good charge carrier mobility and excellent operational durability can lower driving voltage and power consumption, increasing efficiency and half-life time of organic EL device.

SUMMARY OF THE INVENTION

In accordance with the present invention, the ditriphenylene derivative and their use for host material or dopant material of emitting layer for organic EL device are provided. The ditriphenylene derivative can overcome the drawbacks of the conventional materials like as shorter half-life time, lower efficiency and higher power consumption An object of the present invention is to provide the ditriphenylene derivative which can be used as fluorescent host material or dopant material of emitting layer for organic EL device.

An object of the present invention is to provide the ditriphenylene derivative which can be used as phosphorescent host material of emitting layer for organic EL device.

Another object of the present invention is to apply the ditriphenylene derivative for organic EL device and improve the half-life time, lower driving voltage, lower power consumption and increase the efficiency.

The present invention has the economic advantages for industrial practice. Accordingly the present invention, the ditriphenylene derivative which can be used for organic EL device is disclosed. The mentioned the ditriphenylene derivative is represented by the following formula (I):

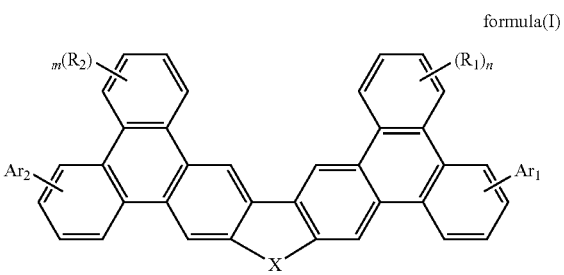

formula(I)

Wherein m, n represent an integer of 0 to 10. X is a divalent bridge selected from the atom or group consisting from O, S, $C(R_3)(R_4)$, $NR_5$, $Si(R_6)(R_7)$. $Ar_1$, $Ar_2$ are the same or different. $Ar_1$, $Ar_2$ represent a hydrogen atom, a halide, a substituted or unsubstituted arylamine group, a substituted or unsubstituted aryl group system having 5 to 60 aromatic ring atoms and each aromatic ring to form a mono or polycyclic ring system, a substituted or unsubstituted heteroaryl group system having 5 to 60 aromatic ring atoms and each aromatic ring to form a mono or polycyclic ring system. $R_1$ to $R_7$ are identical or different. $R_1$ to $R_7$ are independently selected from the group consisting of a hydrogen atom, alkyl group having 1 to 20 carbon atoms, a substituted or unsubstituted aryl group having 6 to 50 carbon atoms, a substituted or unsubstituted aralkyl group having 6 to 50 carbon atoms, a substituted or unsubstituted heteroaryl group having 6 to 50 carbon atoms.

According to the present invention, the ditriphenylene derivative formula (I) preferably used as fluorescent host material or dopant material of emitting layer for organic EL device is represented by the following formula (II):

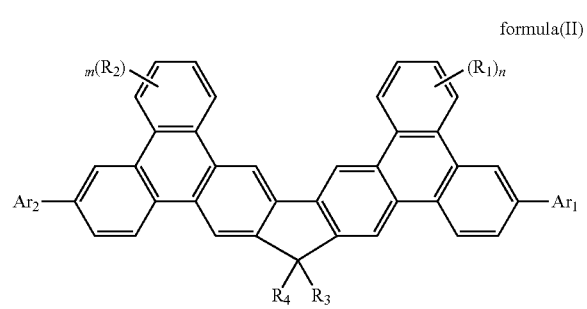

formula(II)

Wherein m, n represent an integer of 0 to 10. $Ar_1$, $Ar_2$ are the same or different. $Ar_1$, $Ar_2$ represent a hydrogen atom, a halide, a substituted or unsubstituted arylamine group, a substituted or unsubstituted aryl group system having 5 to 60 aromatic ring atoms and each aromatic ring to form a mono or polycyclic ring system, a substituted or unsubstituted heteroaryl group system having 5 to 60 aromatic ring atoms and each aromatic ring to form a mono or polycyclic ring system. $R_1$ to $R_4$ are identical or different. $R_1$ to $R_4$ are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms.

According to the present invention, the ditriphenylene derivative formula (I) preferably used as phosphorescent host material for organic EL device is represented by the following formula (III):

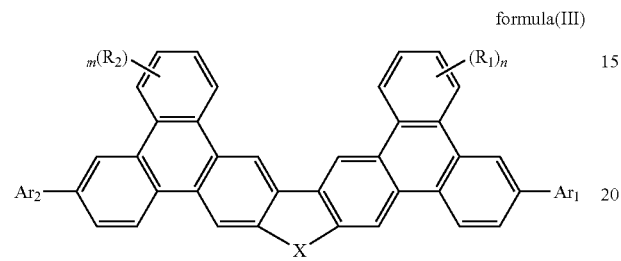

formula(III)

Wherein m, n represent an integer of 0 to 10. X is a divalent bridge selected from the atom or group consisting from O, S, $NR_5$. $Ar_1$, $Ar_2$, $R_5$ are the same or different. $Ar_1$, $Ar_2$, $R_5$ represent a hydrogen atom, a halide, a substituted or unsubstituted arylamine group, a substituted or unsubstituted aryl group system having 5 to 60 aromatic ring atoms and each aromatic ring to form a mono or polycyclic ring system, a substituted or unsubstituted heteroaryl group system having 5 to 60 aromatic ring atoms and each aromatic ring to form a mono or polycyclic ring system. $R_1$, $R_2$ are identical or different. $R_1$, $R_2$ are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms.

BRIEF DESCRIPTION OF THE DRAWINGS

FIG. 3 show the NMR and Photoluminescence spectrogram of intermediate III-a which is important synthetic intermediate of ditriphenylene skeleton for the present invention formula (III).

DESCRIPTION OF THE PREFERRED EMBODIMENTS

Figure 1:
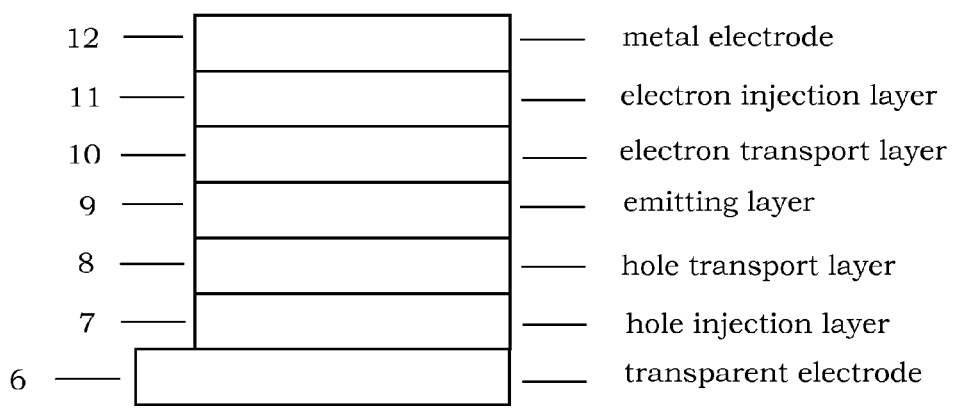
FIG. 1 show one example of organic EL device in the present invention. 6 is transparent electrode, 12 is metal electrode, 7 is hole injection layer which is deposited onto 6, 8 is hole transporting layer which is deposited onto 7, 9 is fluorescent or phosphorescent emitting layer which is deposited onto 8, 10 is electron transporting layer which is deposited onto 9, 11 is electron injection layer which is deposited onto 10.
Figure 2:
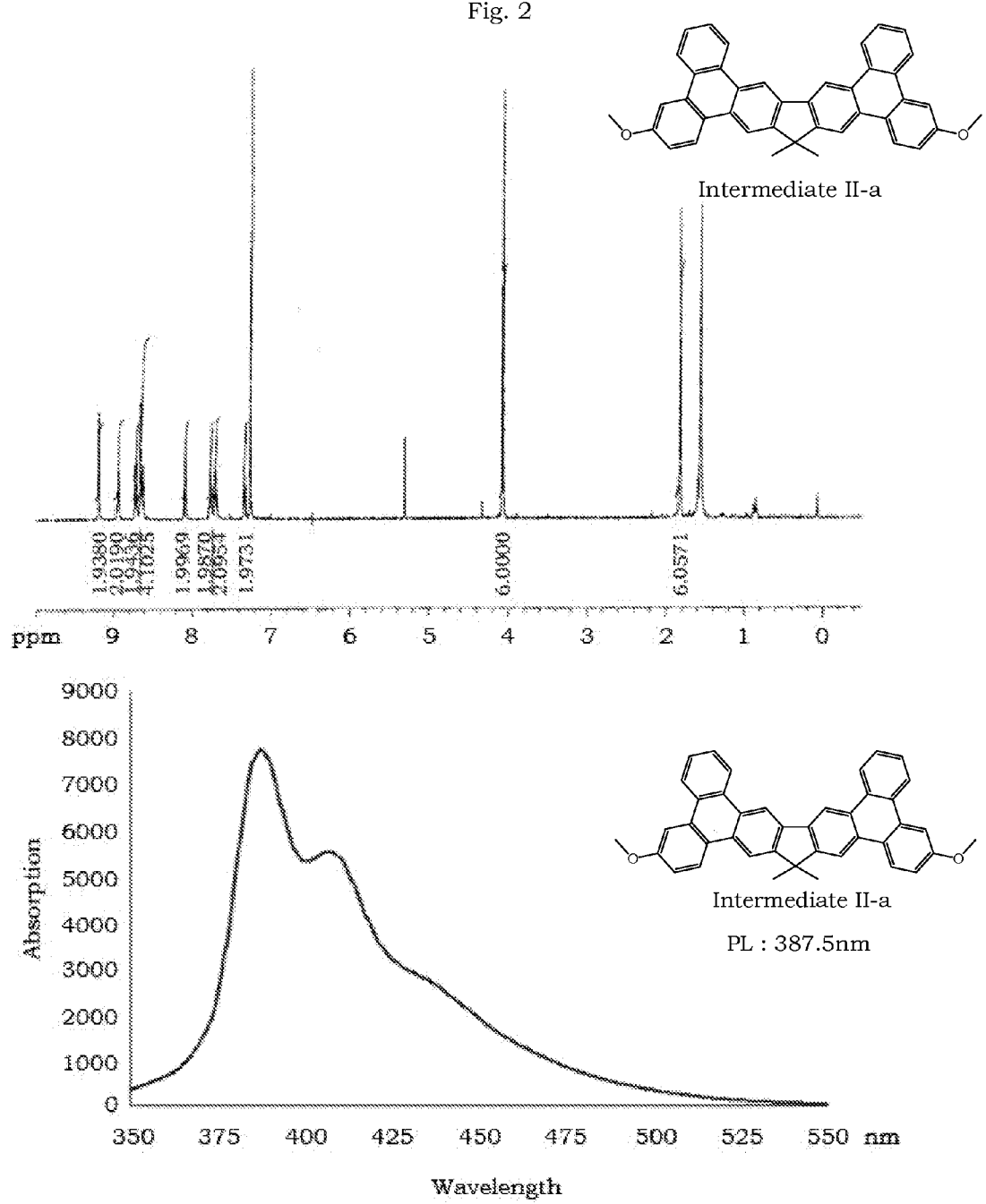
FIG. 2 show the NMR and Photoluminescence spectrogram of Intermediate II-a which is important synthetic intermediate of ditriphenylene skeleton for the present invention formula (II).

What probed into the invention is the ditriphenylene derivative and organic EL device using the ditriphenylene derivative. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

DEFINITION

In a first embodiment of the present invention, the ditriphenylene derivative which can be used as host material or dopant material of emitting layer for organic EL device are disclosed. The mentioned material are represented by the following formula (I):

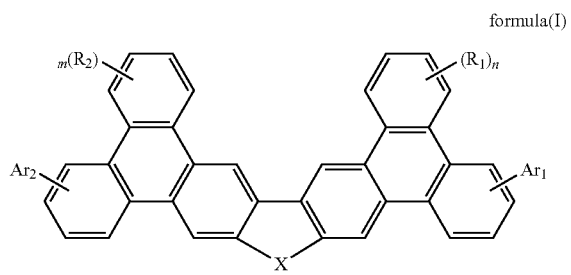

formula(I)

Wherein m, n represent an integer of 0 to 10. X is a divalent bridge selected from the atom or group consisting from O, S, $C(R_3)(R_4)$, $NR_5$, $Si(R_6)(R_7)$. $Ar_1$, $Ar_2$ are the same or different. $Ar_1$, $Ar_2$ represent a hydrogen atom, a halide, a substituted or unsubstituted arylamine group, a substituted or unsubstituted aryl group system having 5 to 60 aromatic ring atoms and each aromatic ring to form a mono or polycyclic ring system, a substituted or unsubstituted heteroaryl group system having 5 to 60 aromatic ring atoms and each aromatic ring to form a mono or polycyclic ring system. $R_1$ to $R_7$ are identical or different. $R_1$ to $R_7$ are independently selected from the group consisting of a hydrogen atom, alkyl group having 1 to 20 carbon atoms, a substituted or unsubstituted aryl group having 6 to 50 carbon atoms, a substituted or unsubstituted aralkyl group having 6 to 50 carbon atoms, a substituted or unsubstituted heteroaryl group having 6 to 50 carbon atoms.

According to the present invention, the ditriphenylene derivative formula (I) preferably used as fluorescent host material or dopant material of emitting layer for organic EL device is represented by the following formula (II):

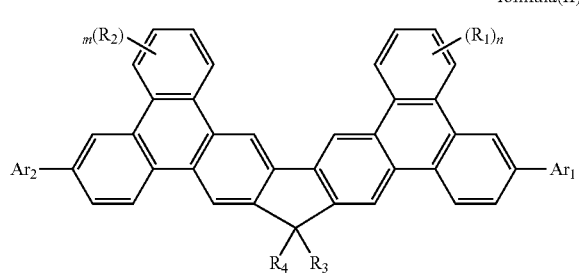

formula(II)

Wherein m, n represent an integer of 0 to 10. $Ar_1$, $Ar_2$ are the same or different. $Ar_1$, $Ar_2$ represent a hydrogen atom, a halide, a substituted or unsubstituted arylamine group, a substituted or unsubstituted aryl group system having 5 to 60 aromatic ring atoms and each aromatic ring to form a mono or polycyclic ring system, a substituted or unsubstituted heteroaryl group system having 5 to 60 aromatic ring atoms and each aromatic ring to form a mono or polycyclic ring system. $R_1$ to $R_4$ are identical or different. $R_1$ to $R_4$ are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms. Wherein preferably $Ar_1$, $Ar_2$ are substituted or unsubstituted arylamine group or aryl group consisted of one substituted or unsubstituted fused ring hydrocarbon units with one to five rings or two substituted or unsubstituted fused ring hydrocarbon units with one to five rings and represented by the following:

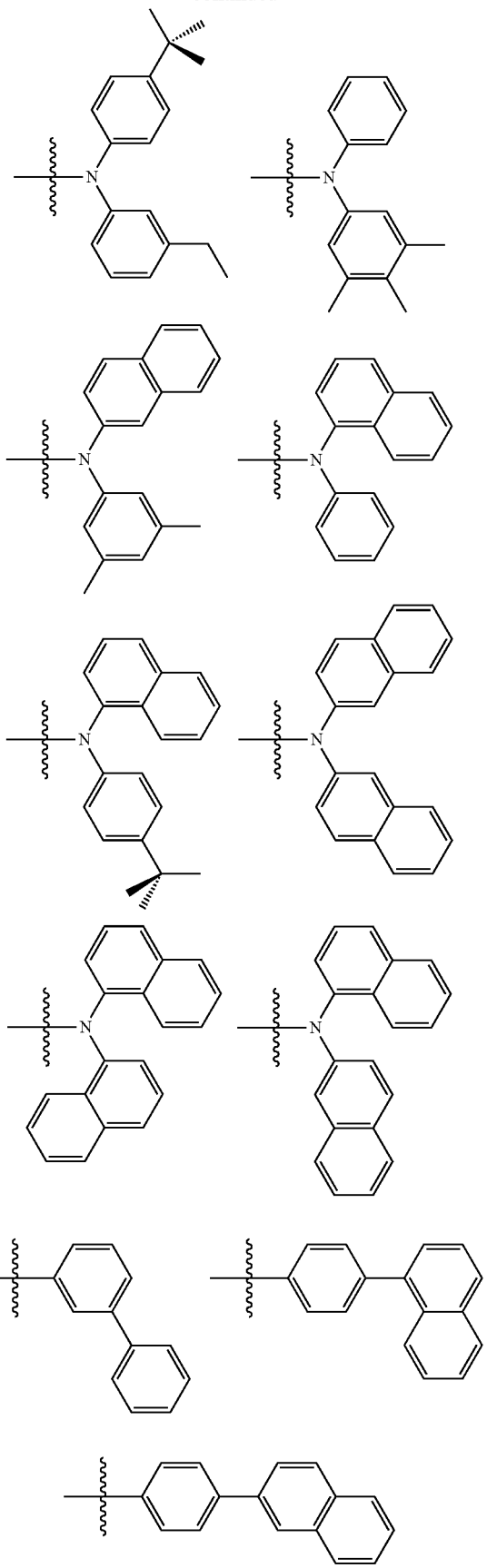

-continued
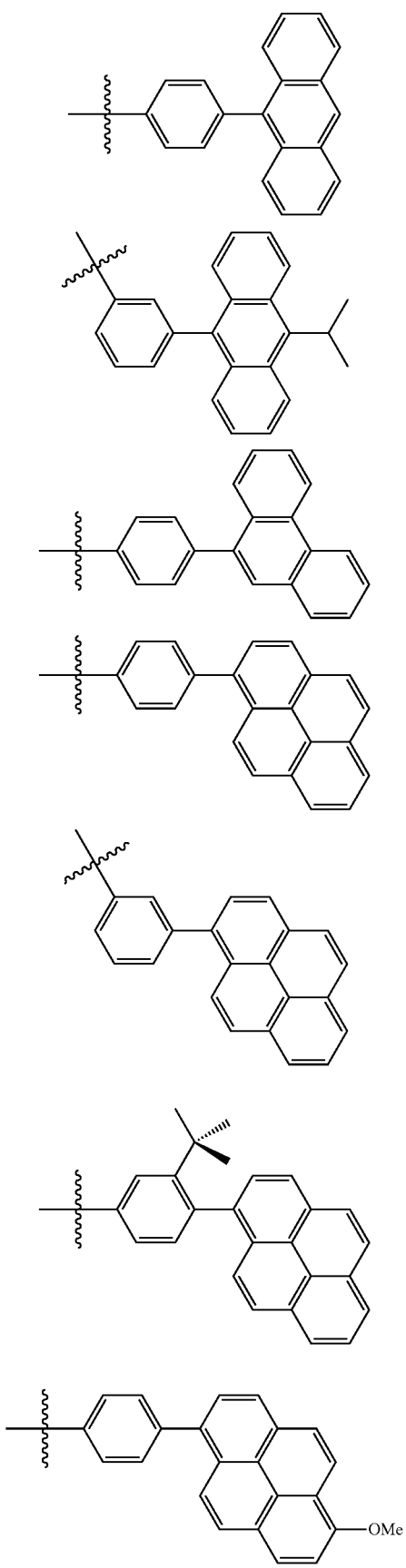
-continued
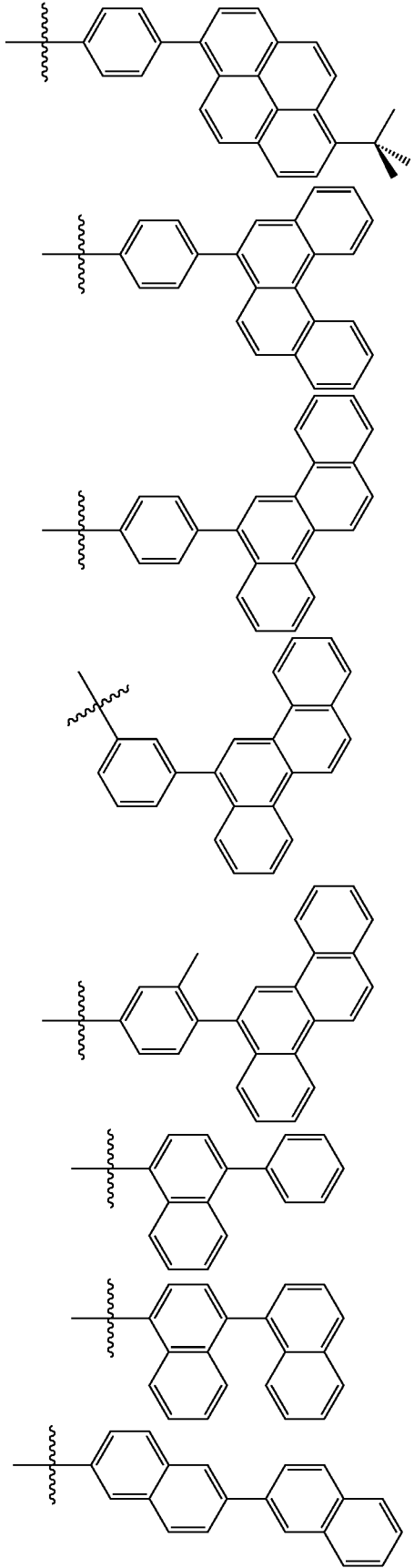

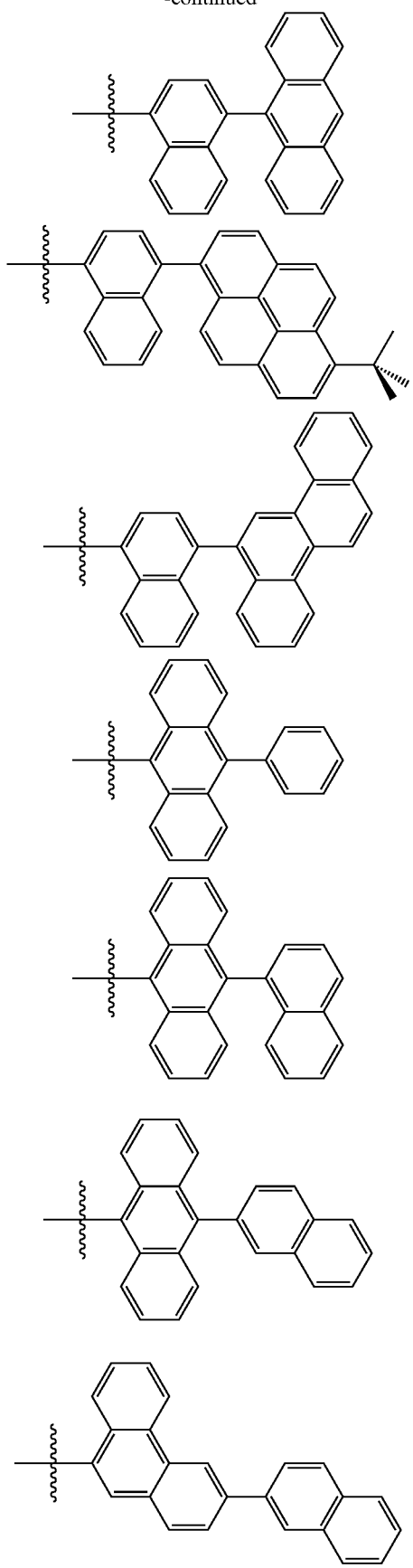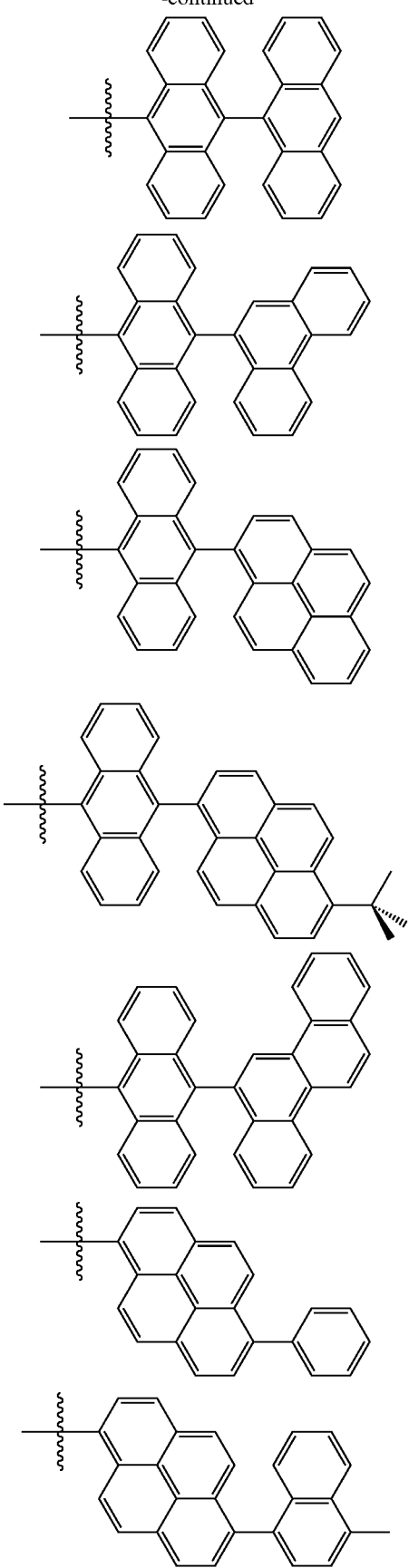

-continued

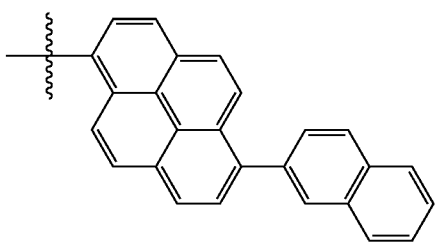

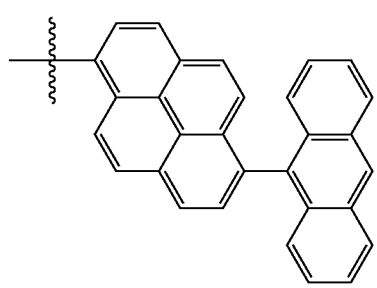

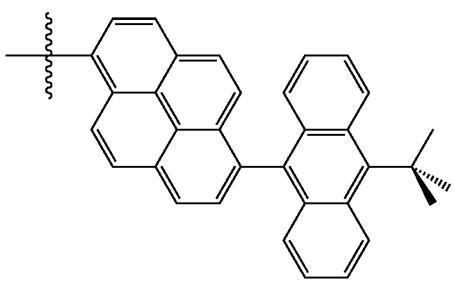

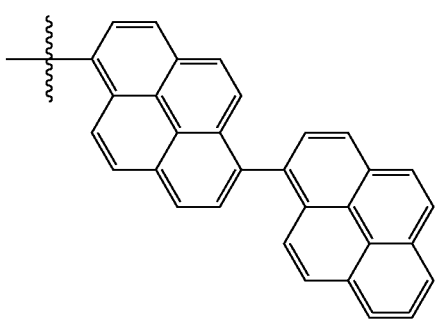

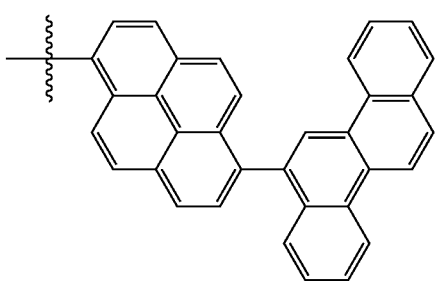

According to the present invention, the ditriphenylene derivative formula (I) preferably used as phosphorescent host material of emitting layer for organic EL device is represented by the following formula (III)

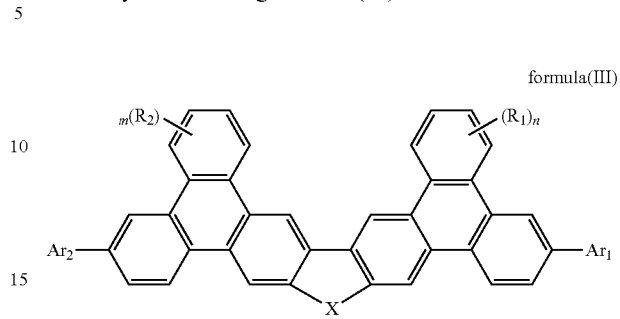

formula(III)

Wherein m, n represent an integer of 0 to 10. X is a divalent bridge selected from the atom or group consisting from O, S, $NR_5$. $Ar_1$, $Ar_2$, $R_5$ are the same or different. $Ar_1$, $Ar_2$, $R_5$ represent a hydrogen atom, a halide, a substituted or unsubstituted arylamine group, a substituted or unsubstituted aryl group system having 5 to 60 aromatic ring atoms and each aromatic ring to form a mono or polycyclic ring system, a substituted or unsubstituted heteroaryl group system having 5 to 60 aromatic ring atoms and each aromatic ring to form a mono or polycyclic ring system. $R_1$, $R_2$ are identical or different. $R_1$, $R_2$ are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms. Wherein preferably $Ar_1$, $Ar_2$, $R_5$ are heteroaryl group or aryl group and represented by the following:

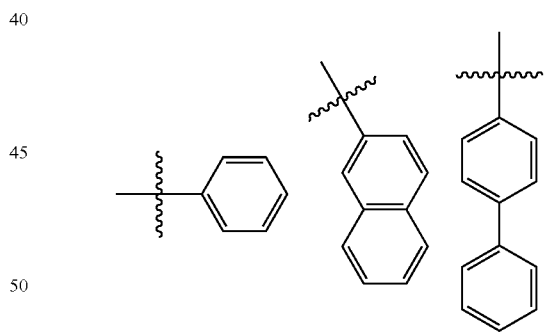

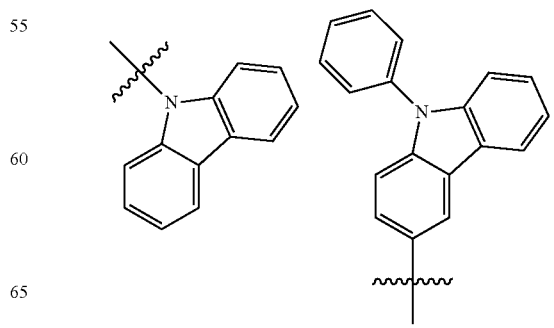

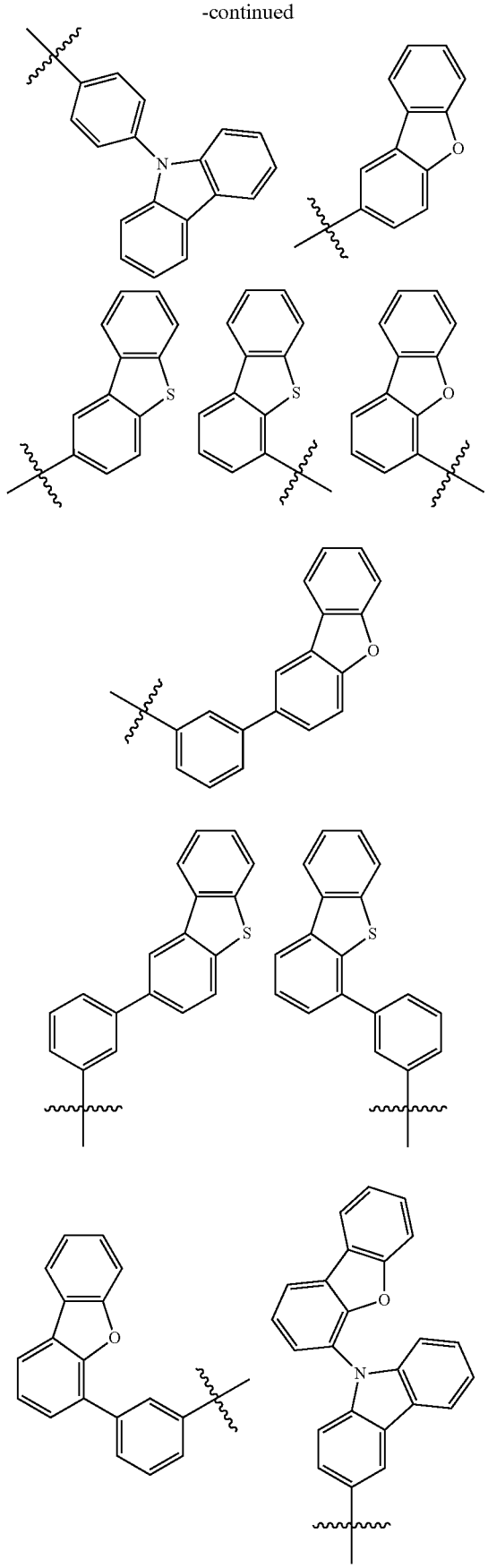

15
-continued
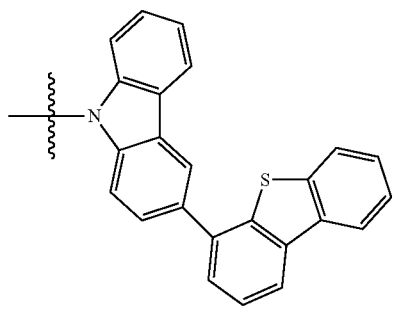
16
-continued
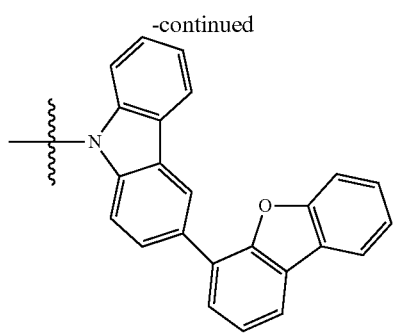
In this embodiment, some preferable ditriphenylene derivatives are shown below:
II-1
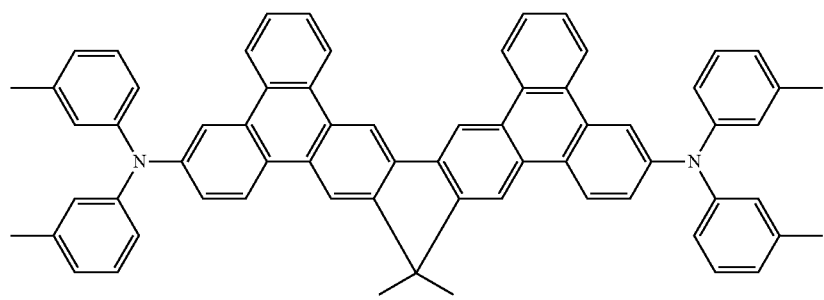
II-2
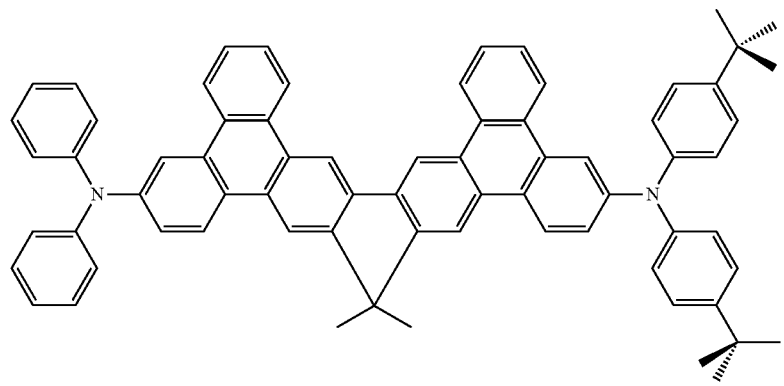
II-3
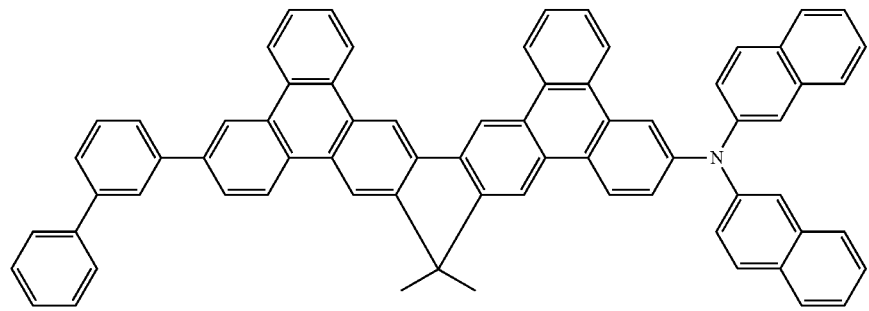

-continued
II-4
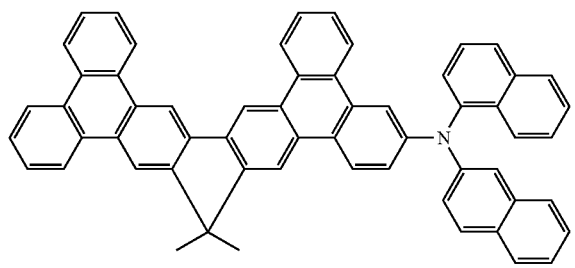
II-5
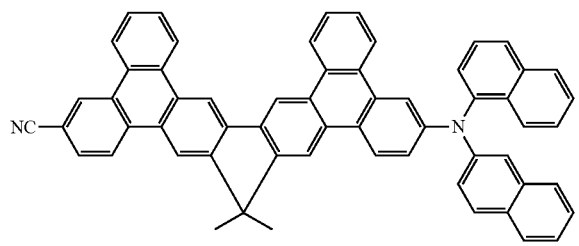
II-6
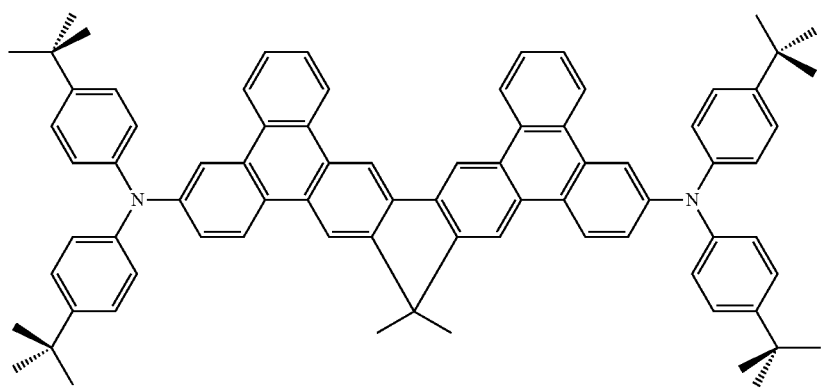
II-7
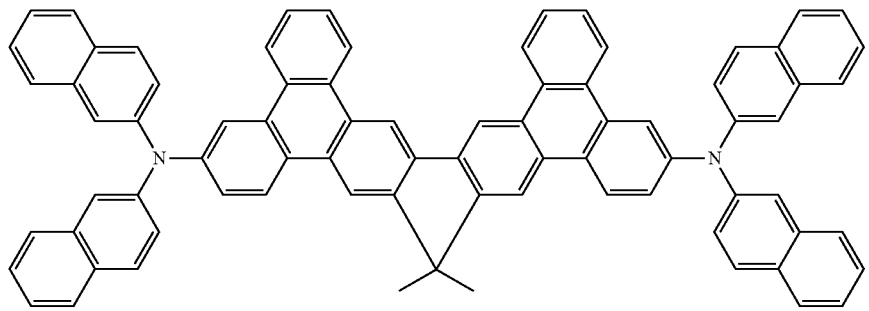
II-8
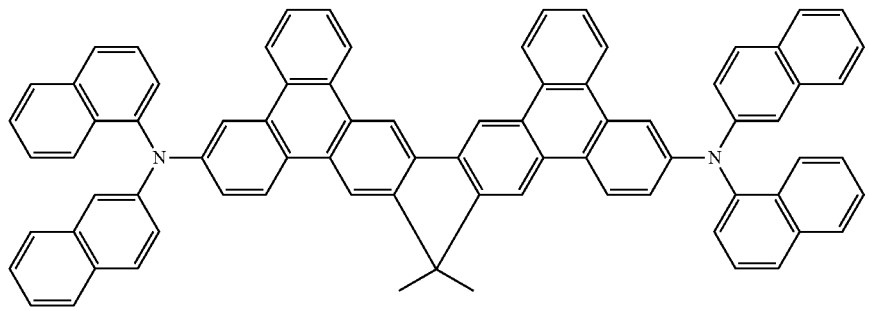
II-9
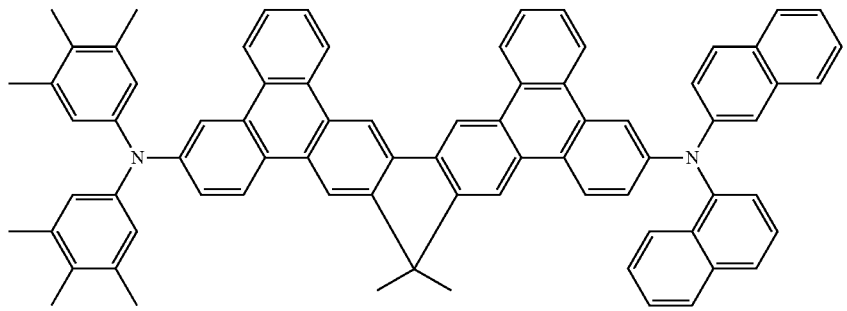

-continued
II-10
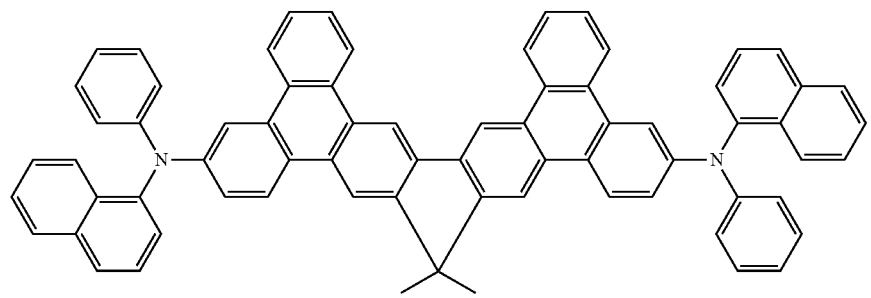
II-11
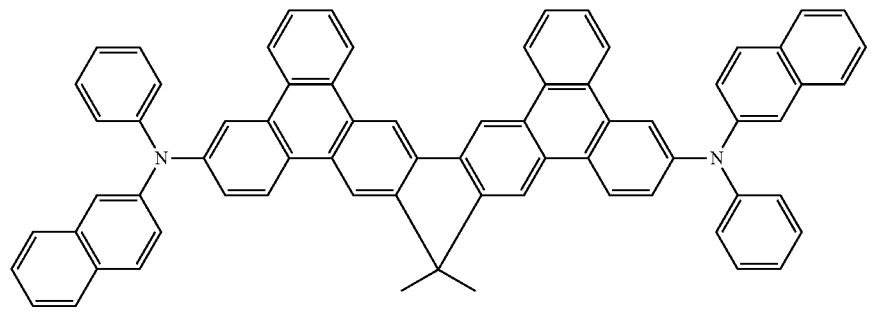
II-12
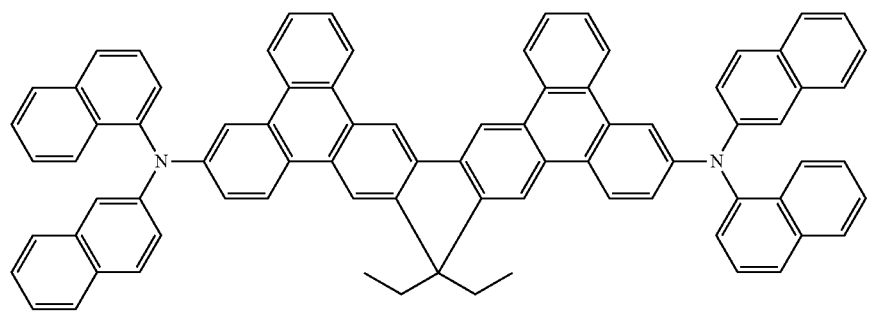
II-13
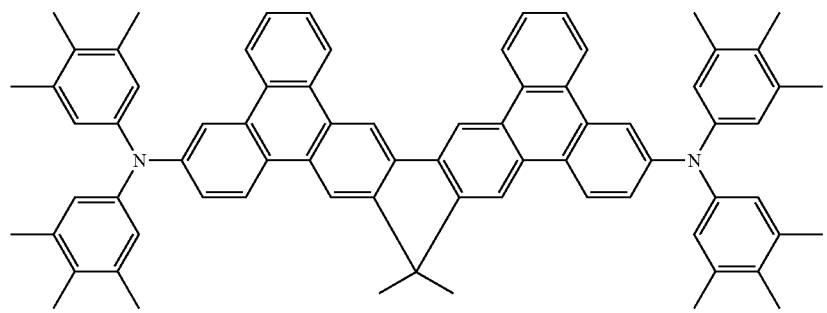
II-14
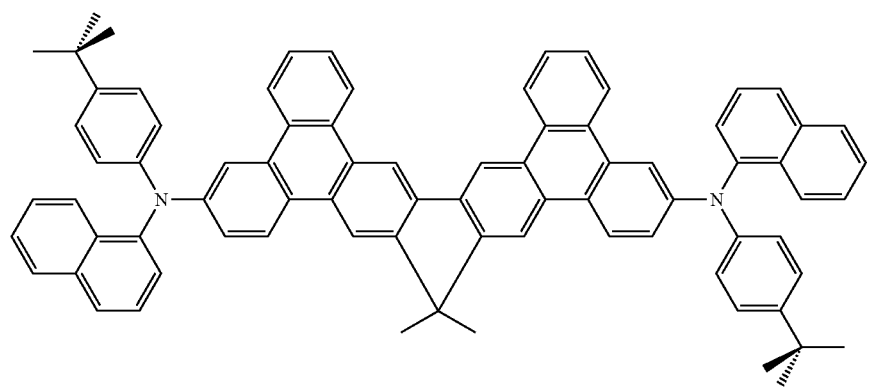

II-15
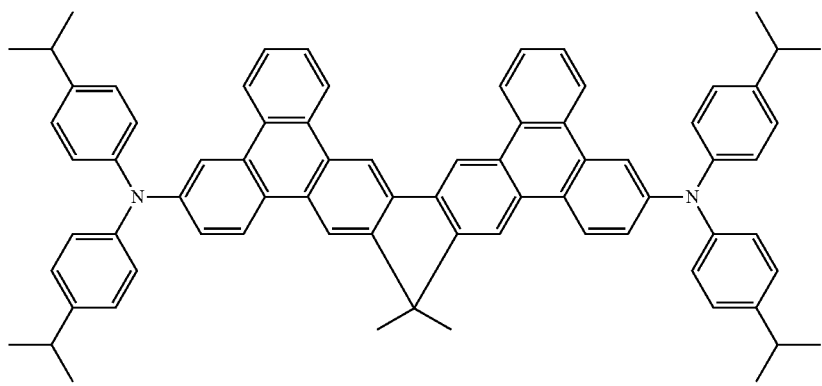
II-16
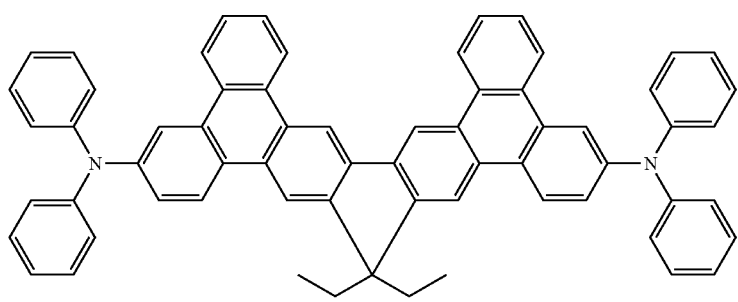
II-17
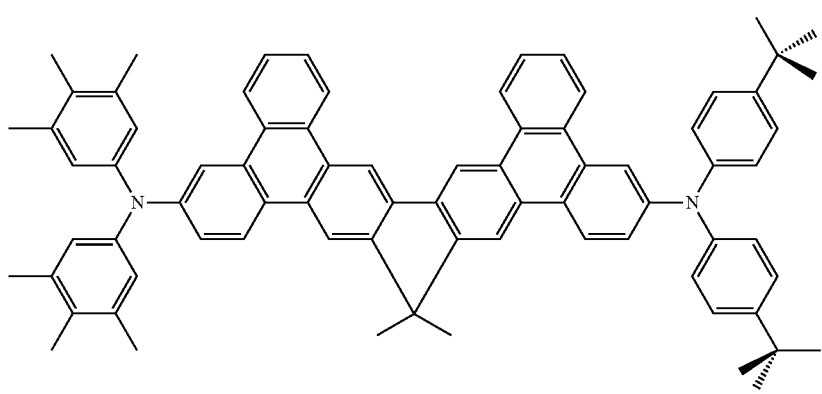
II-18
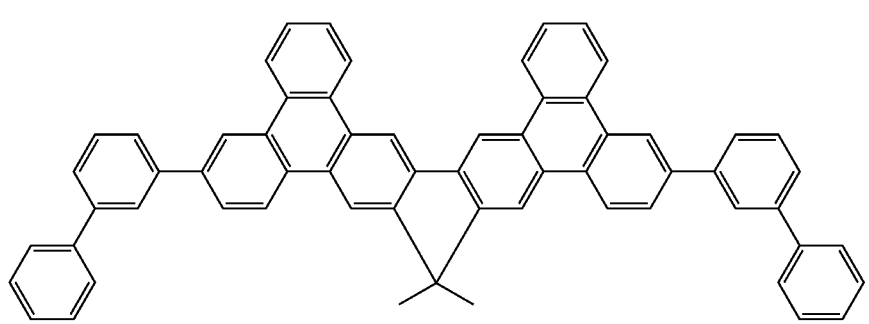

-continued
II-19
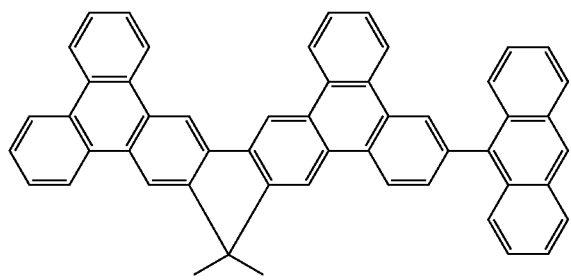
II-20
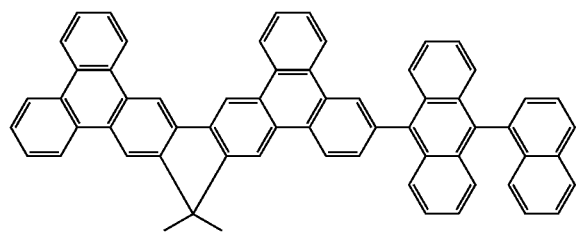
II-21
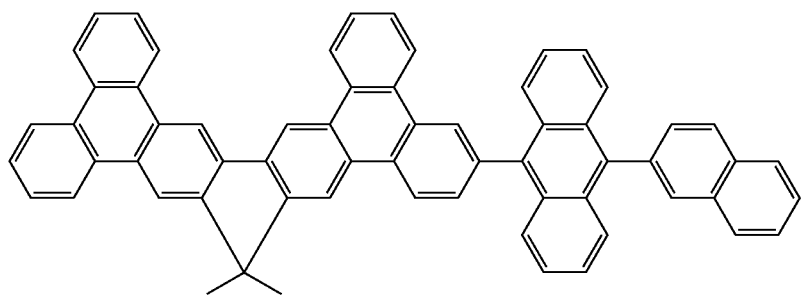
II-22
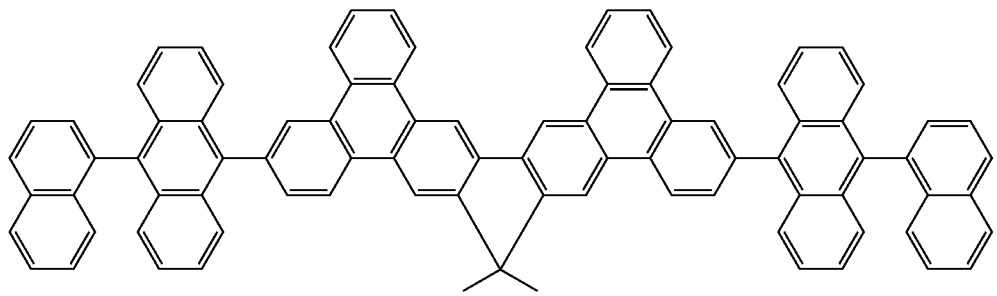
II-23
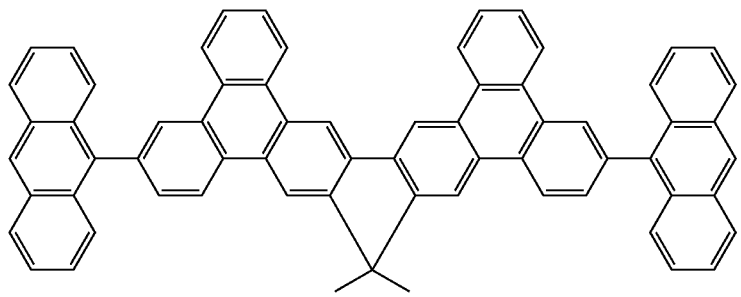
II-24
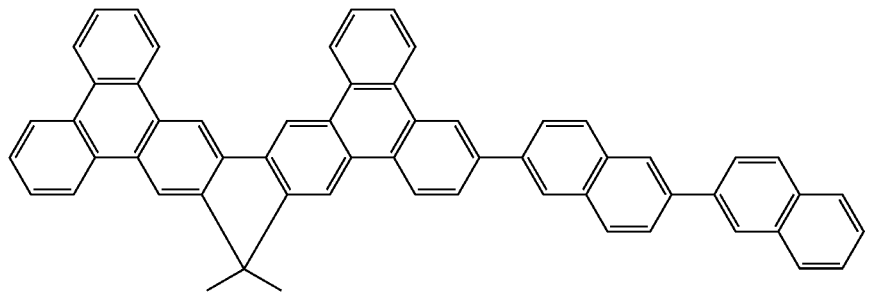

-continued

II-31
II-32
II-33
II-34
II-35
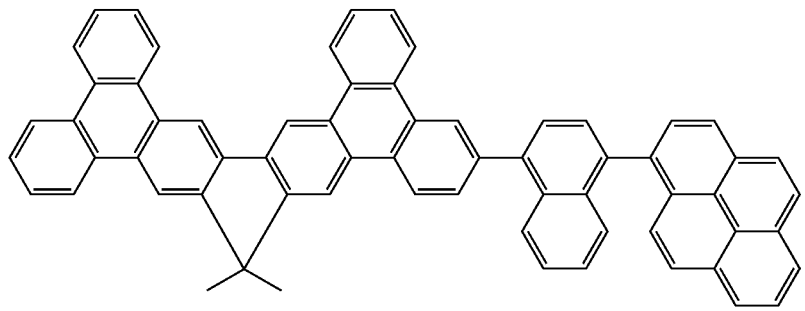

-continued
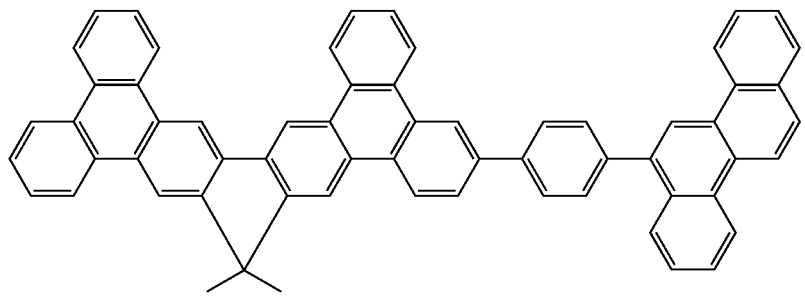
II-36
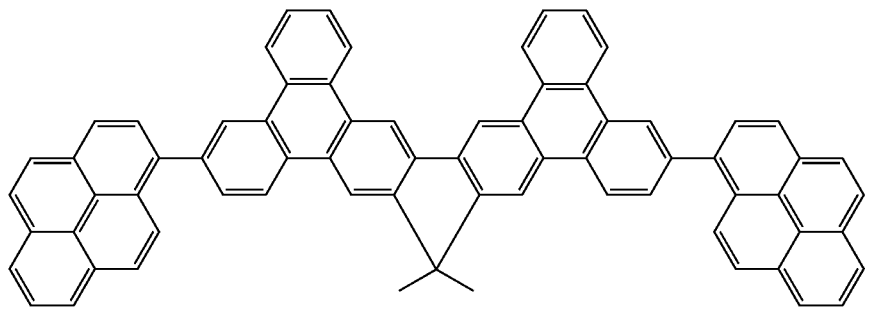
II-37
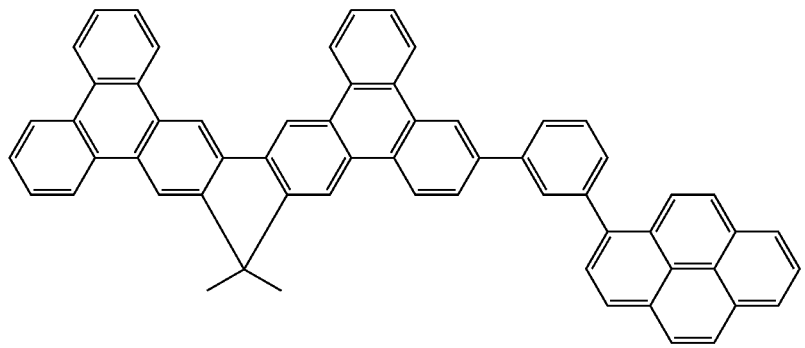
II-38
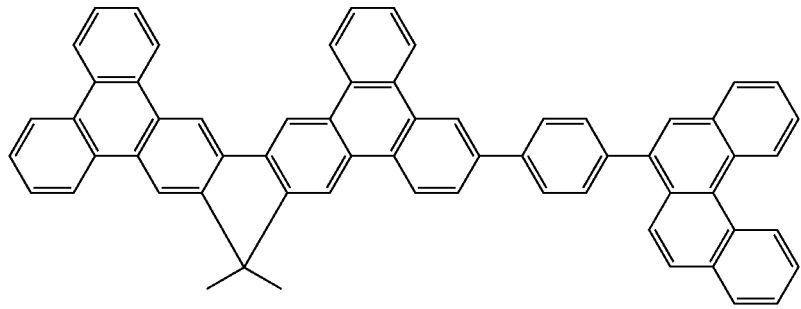
II-39
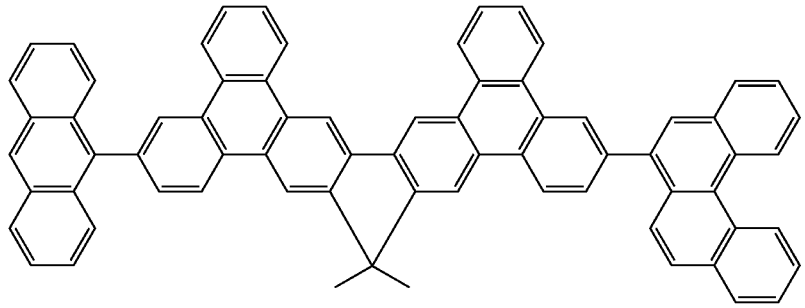
II-40

-continued
III-1
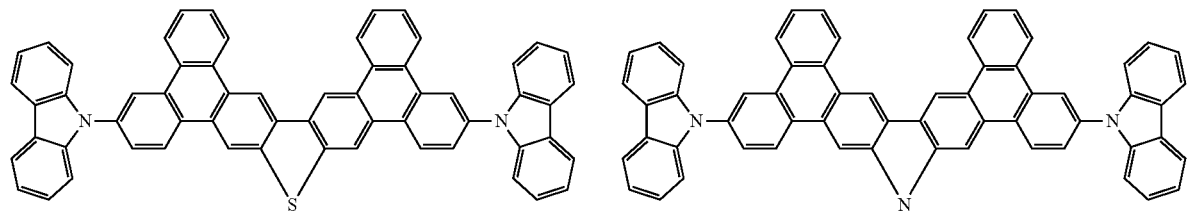
III-2
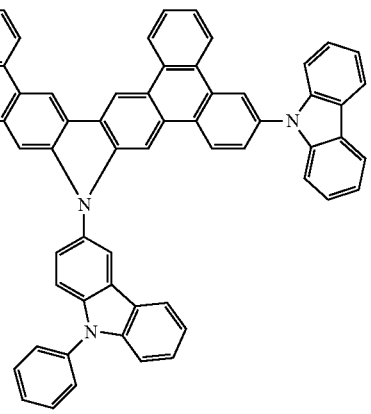
III-3
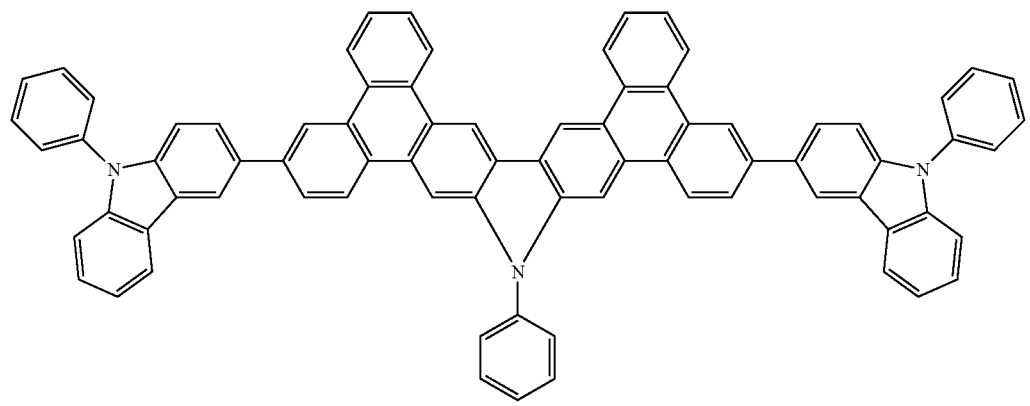
III-4
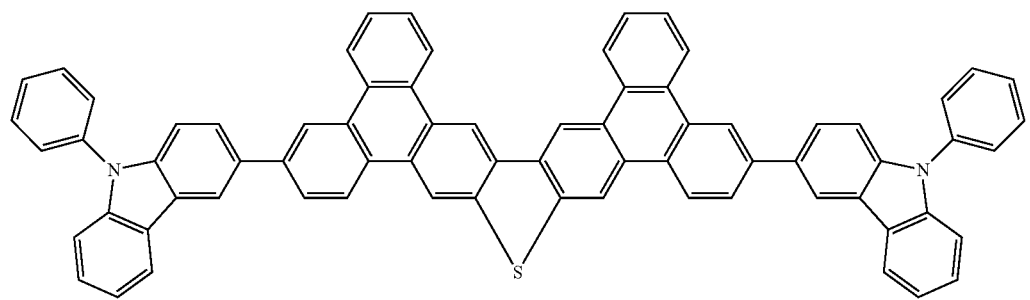
III-5
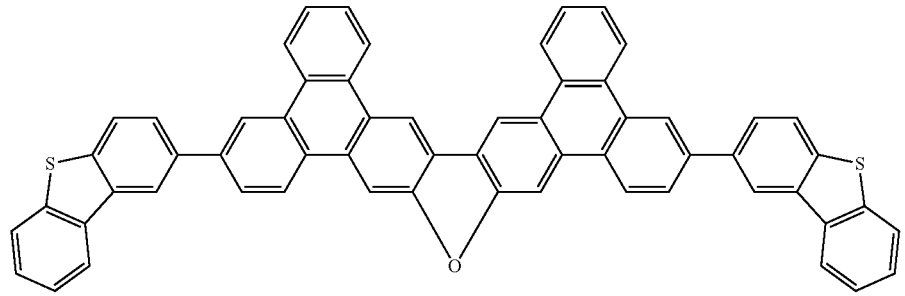

III-6
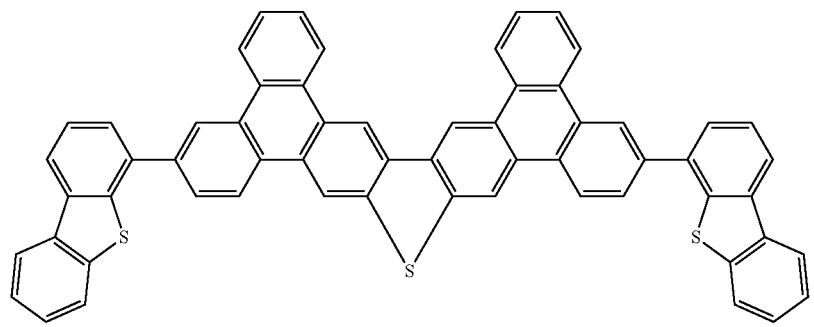
III-7
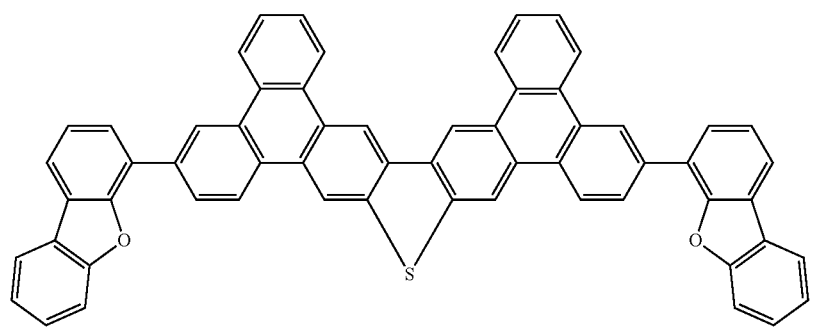
III-8
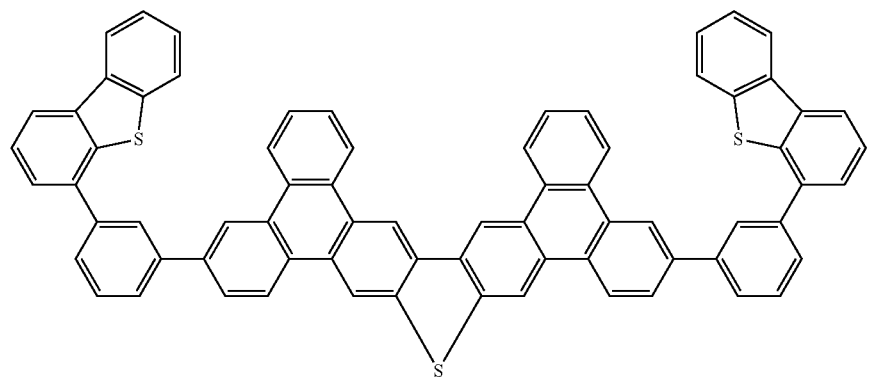
III-9
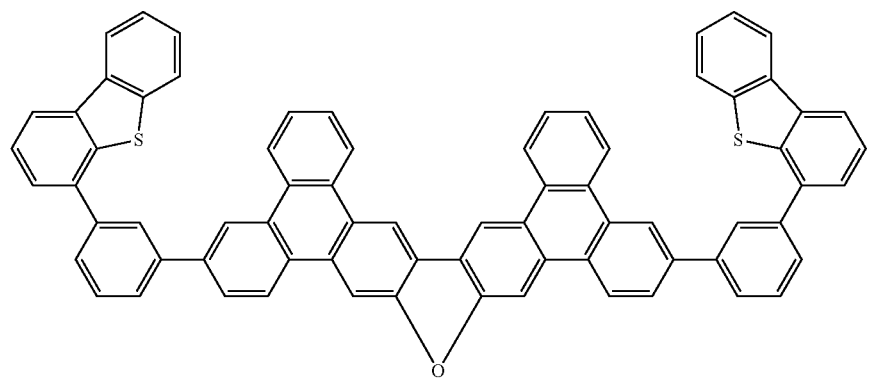

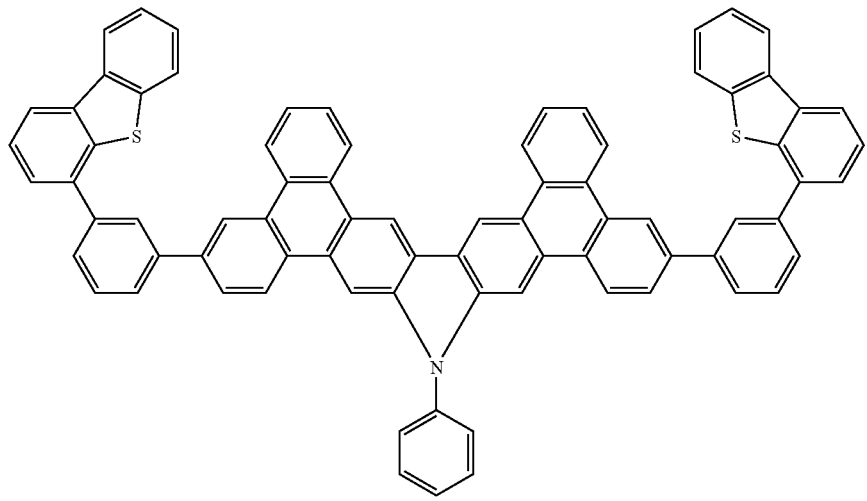
III-10
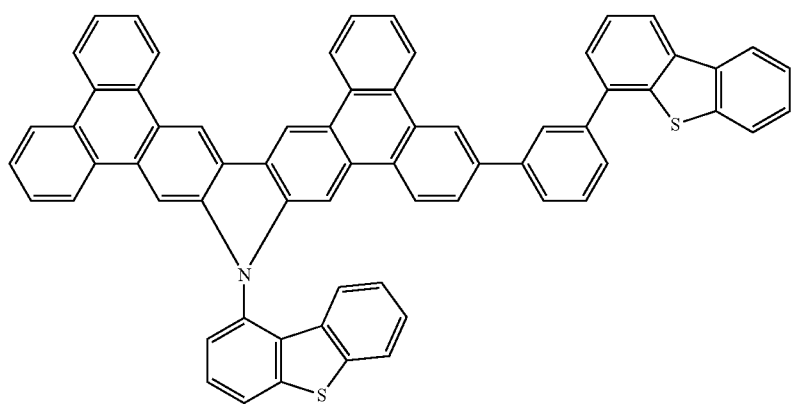
III-11
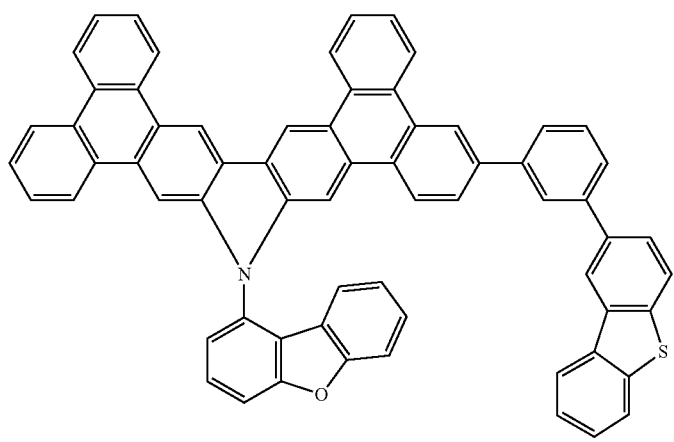
III-12

III-13
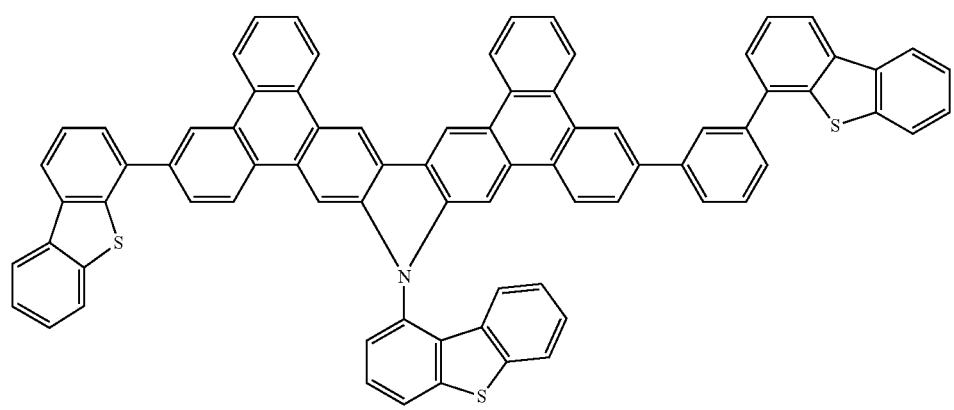
III-14
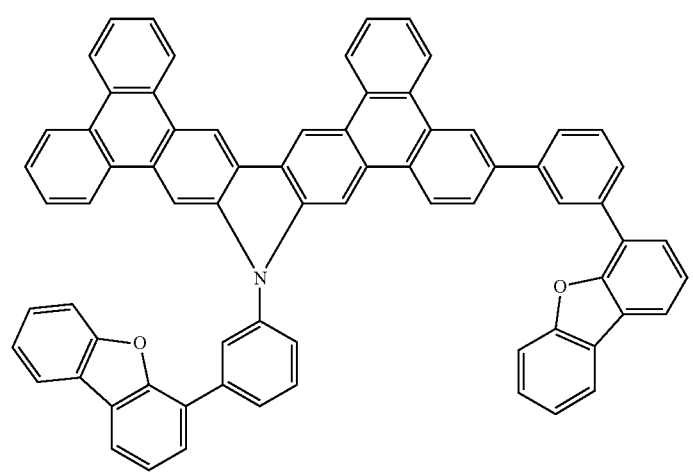
III-15
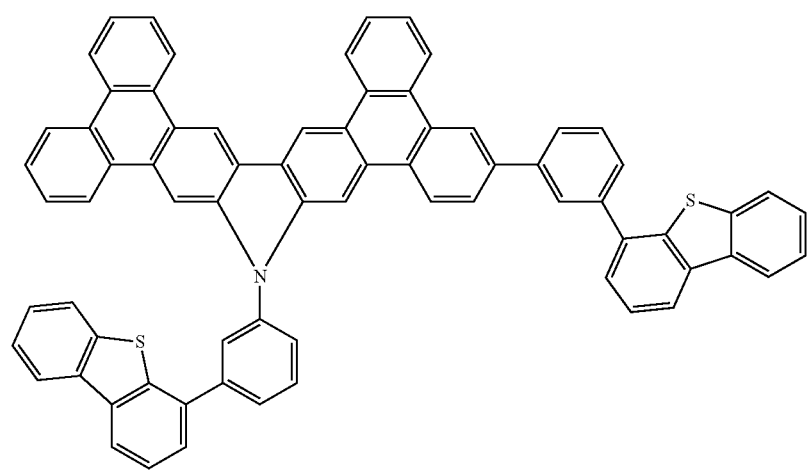

III-16
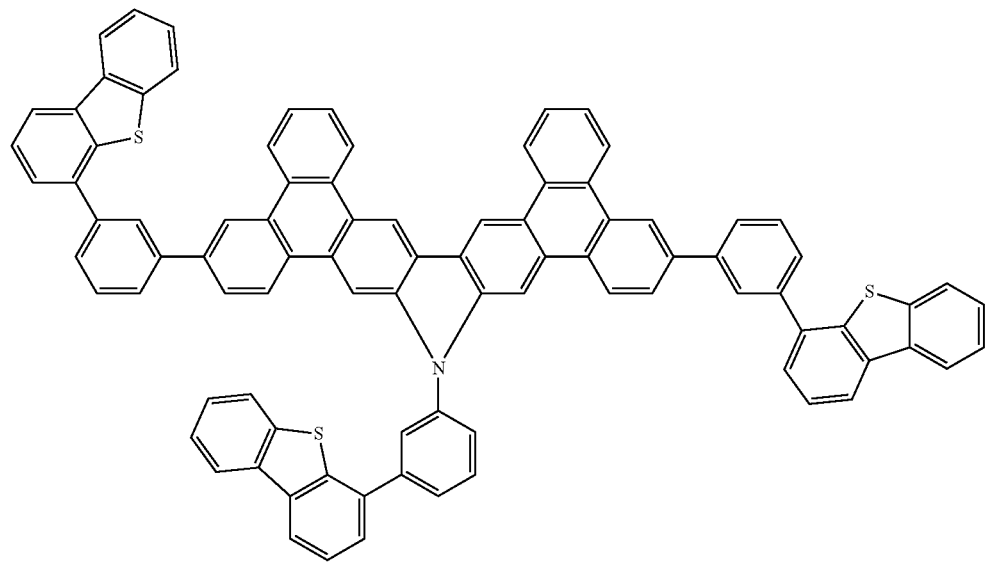
III-17
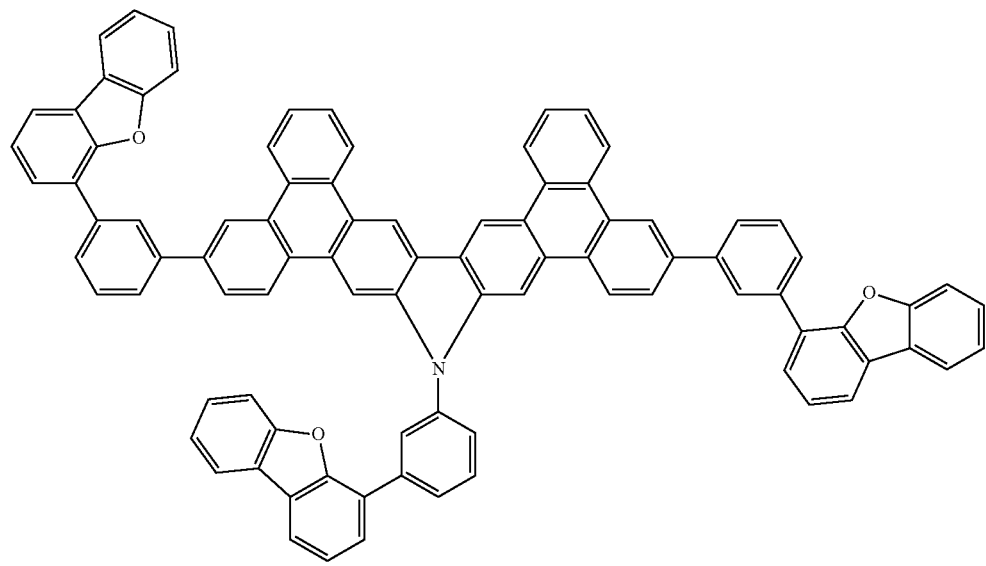
III-18
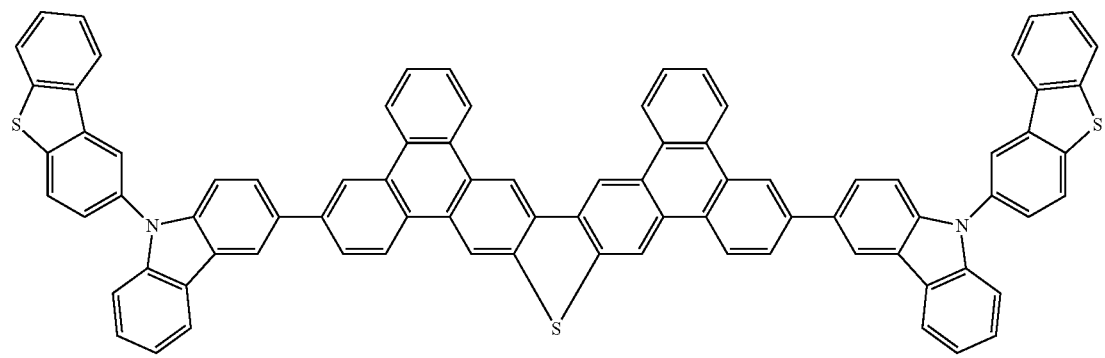

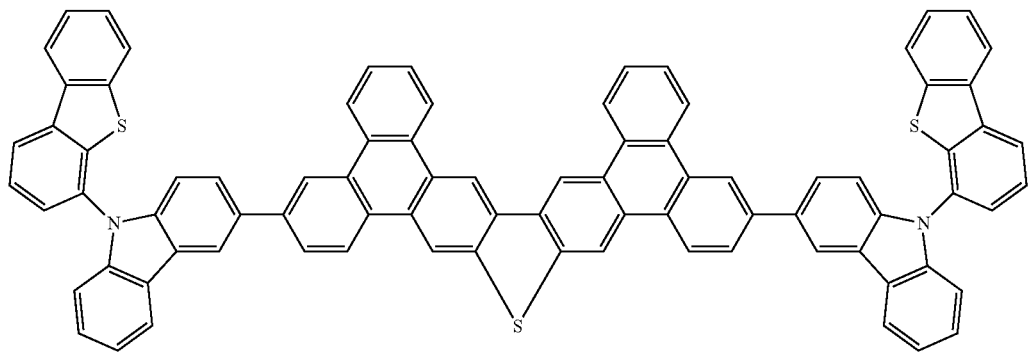
III-19
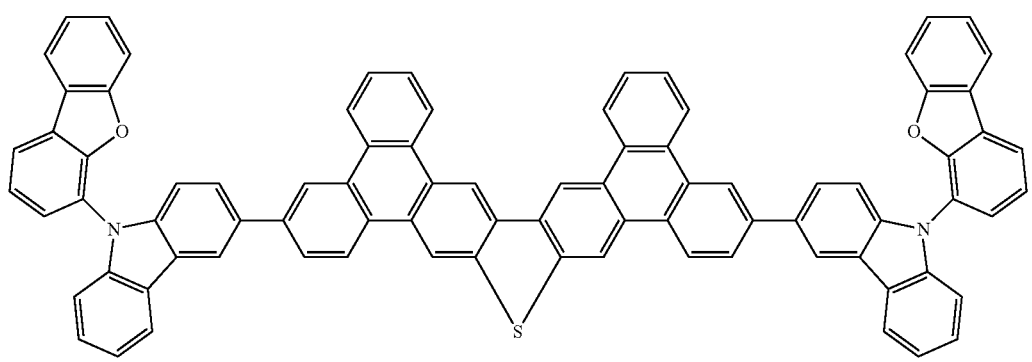
III-20
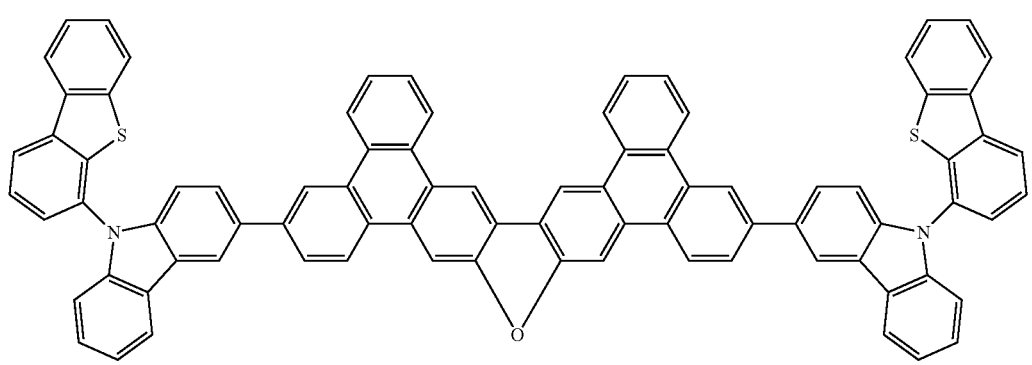
III-21
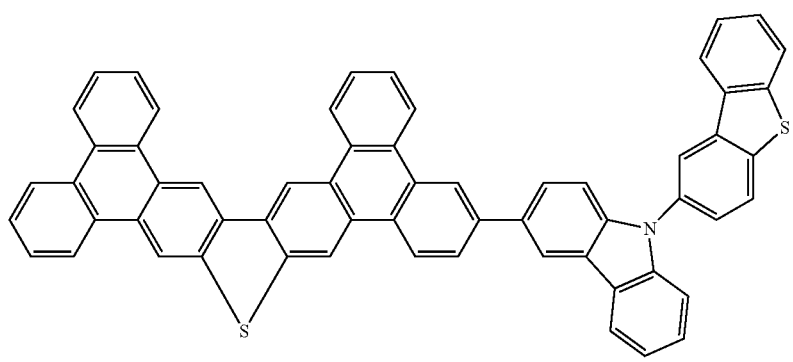
III-22

III-23
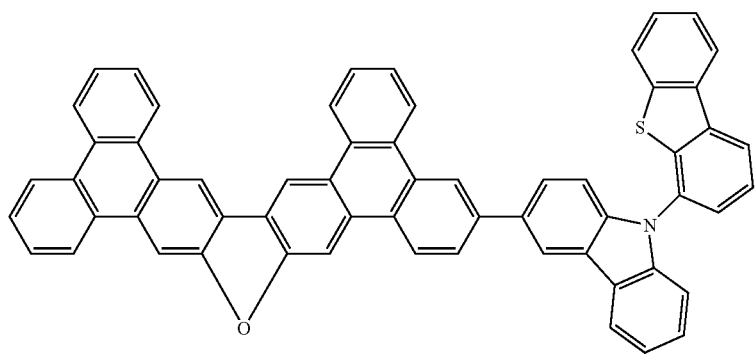
III-24
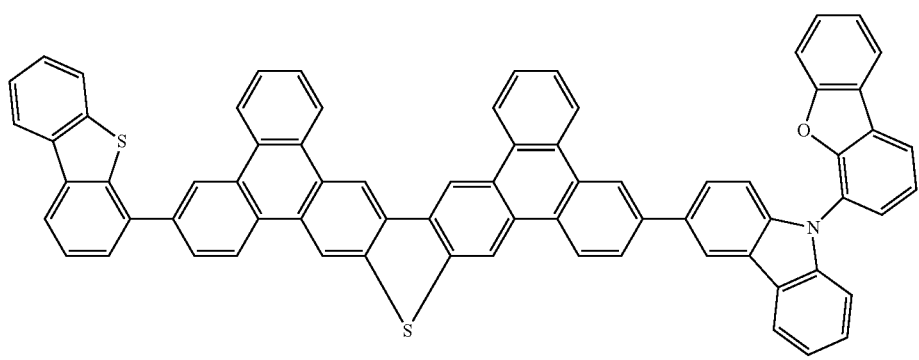
III-25
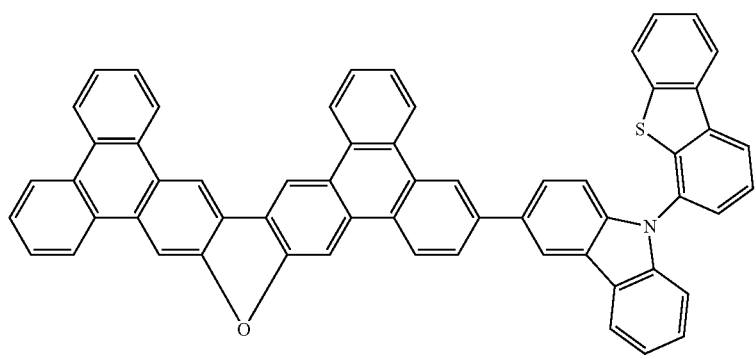
III-26
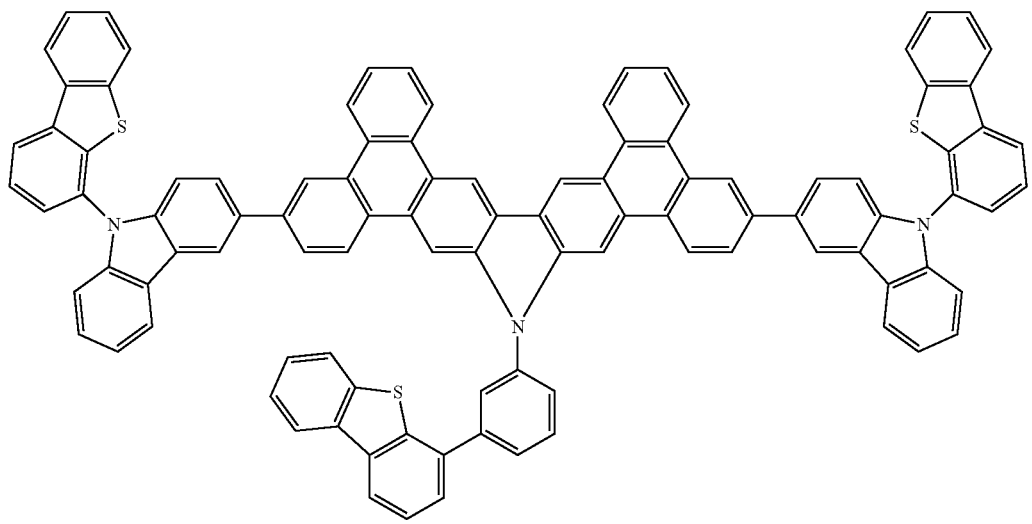

-continued
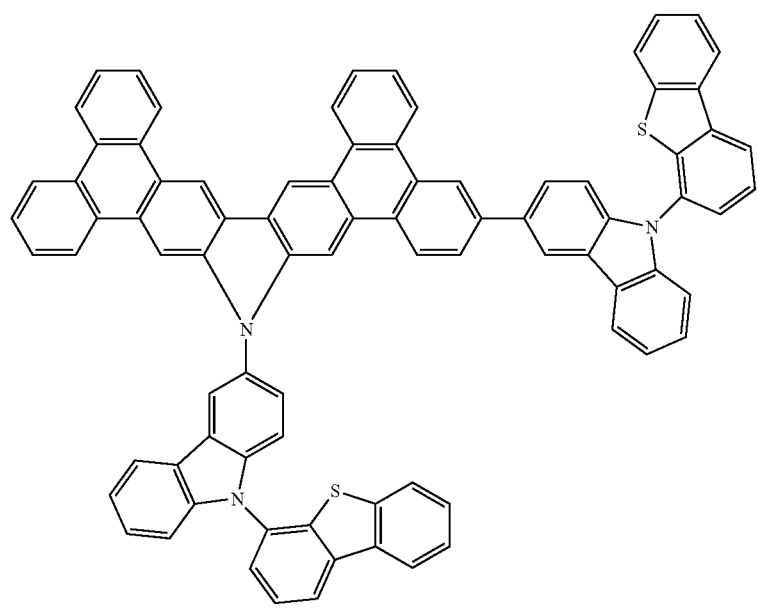
III-27
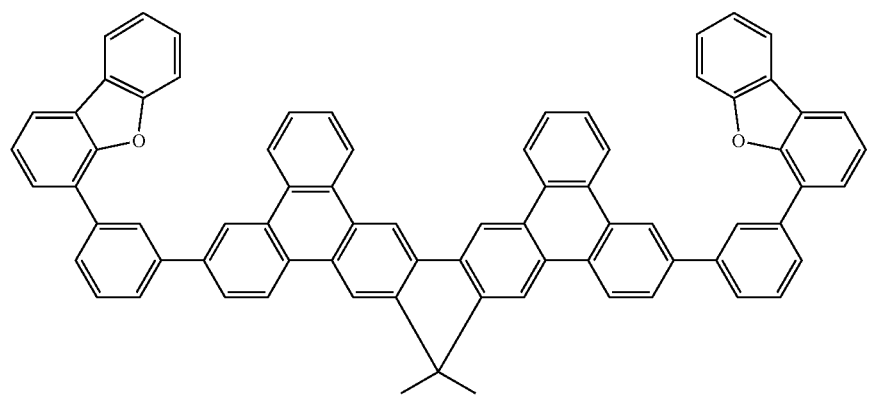
III-28
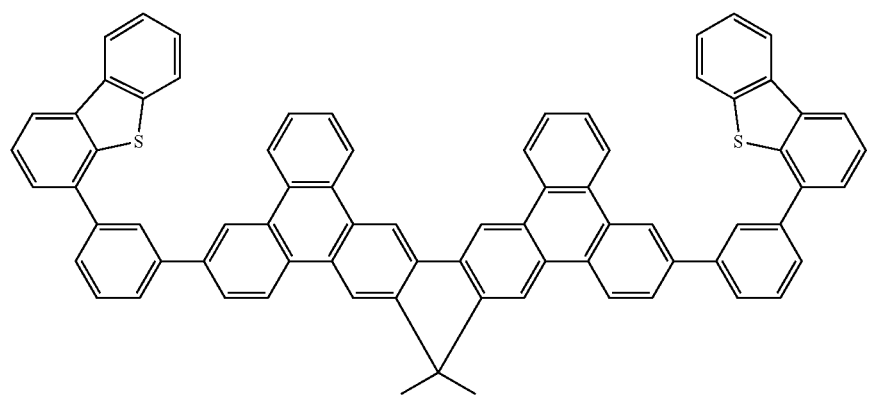
III-29

-continued
III-30
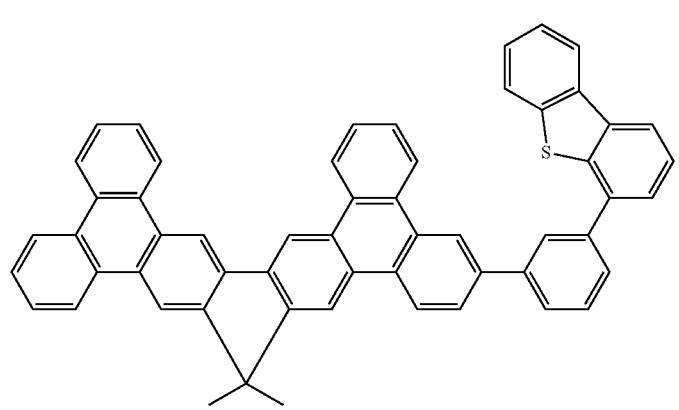
III-31
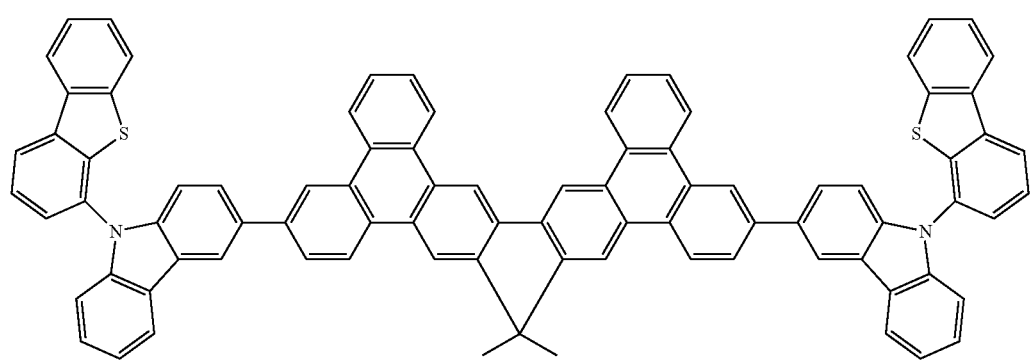
III-32
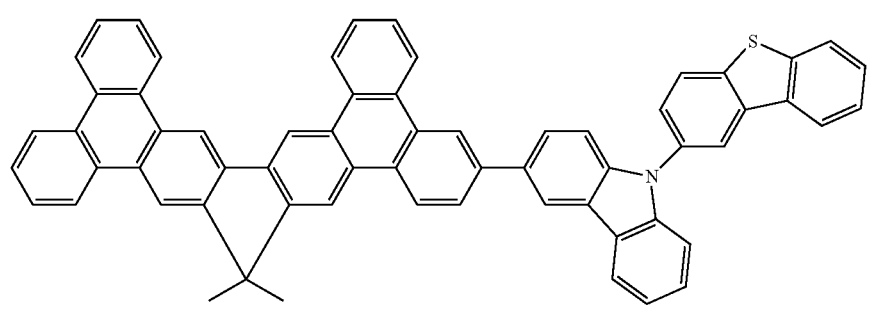
III-33
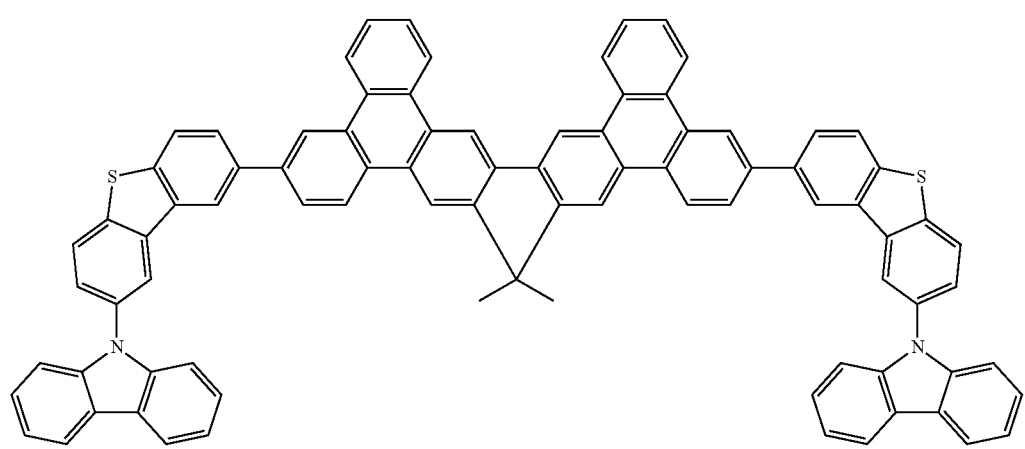

-continued
III-34
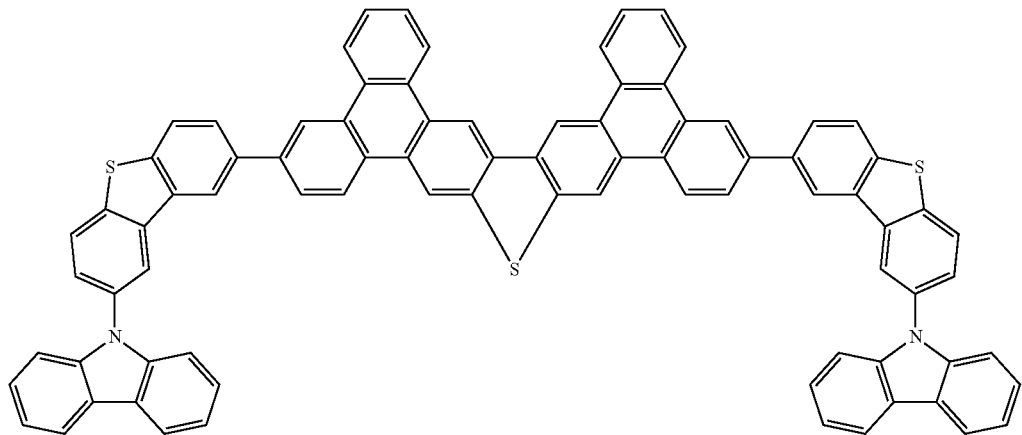
III-35
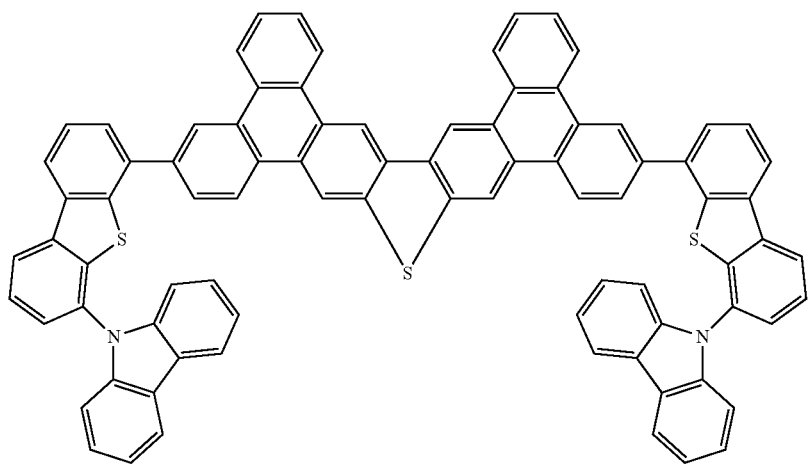
III-36
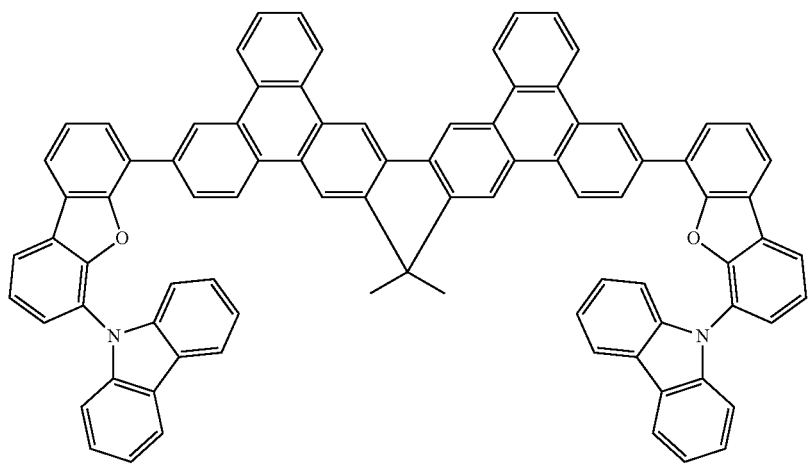

III-37
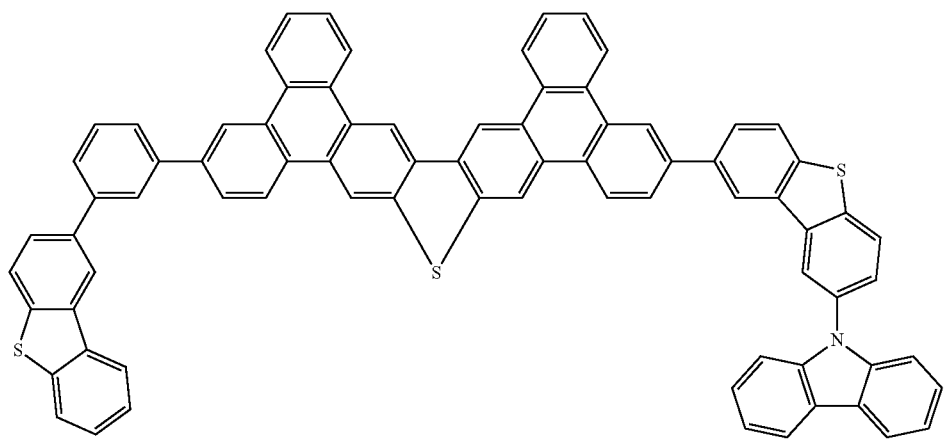
III-38
III-39
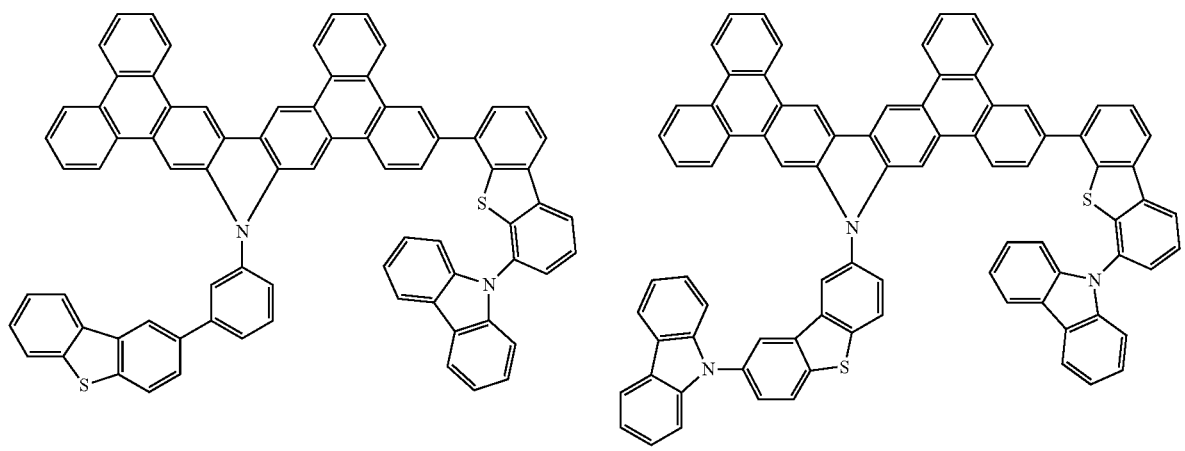
III-40
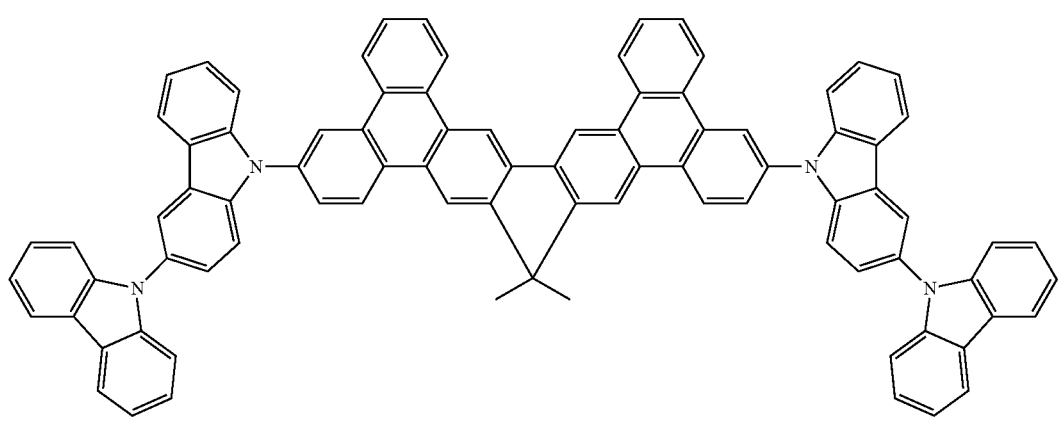

III-41
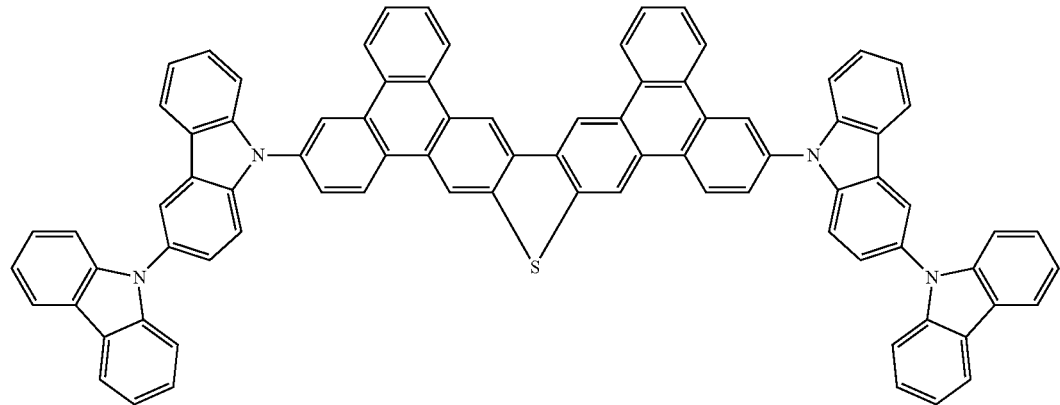
III-42
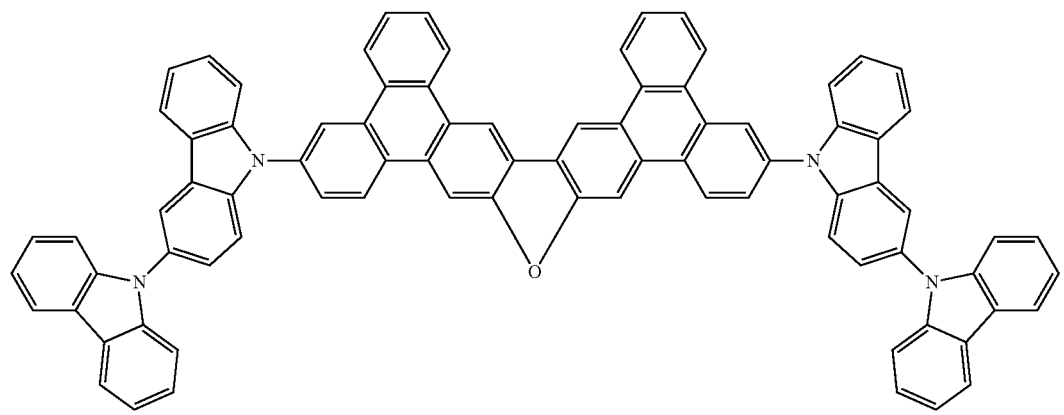
III-43
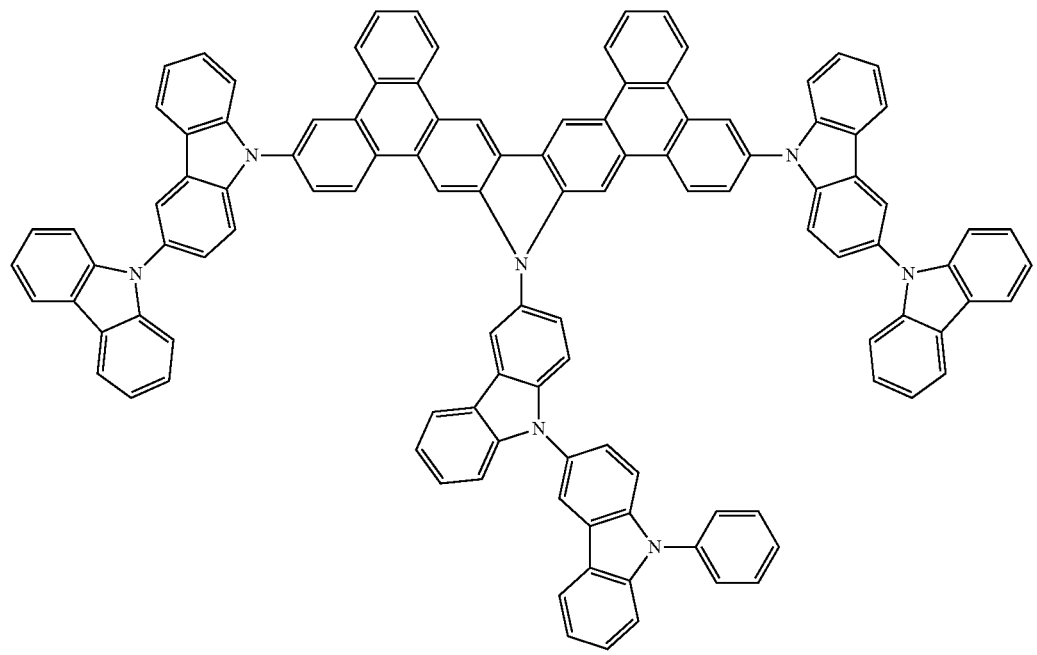

-continued
III-44
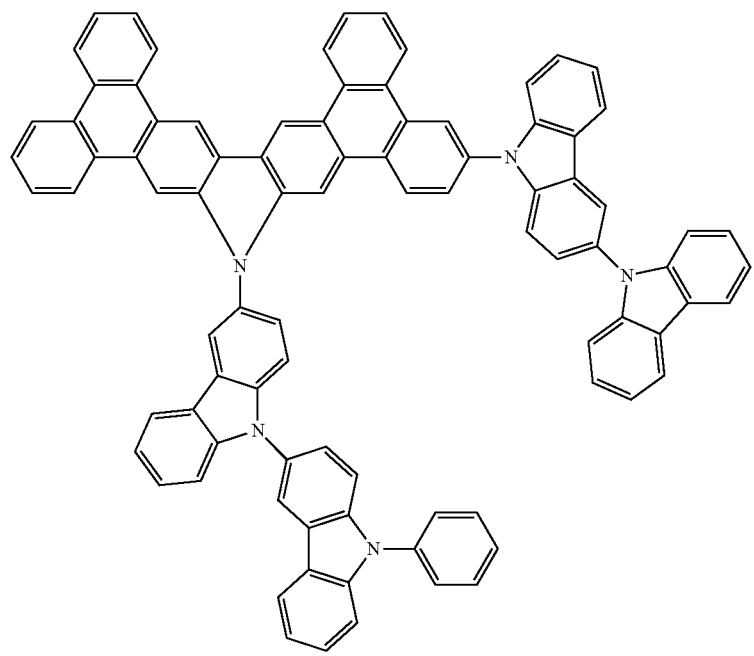
III-45
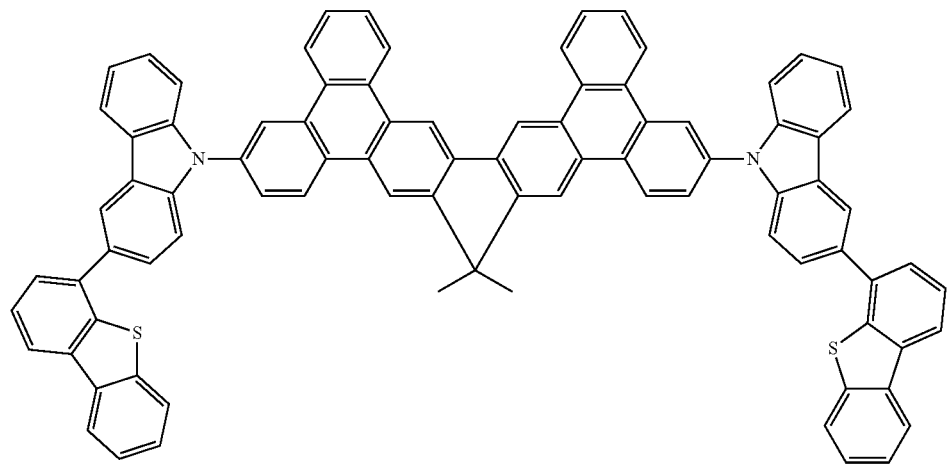
III-46
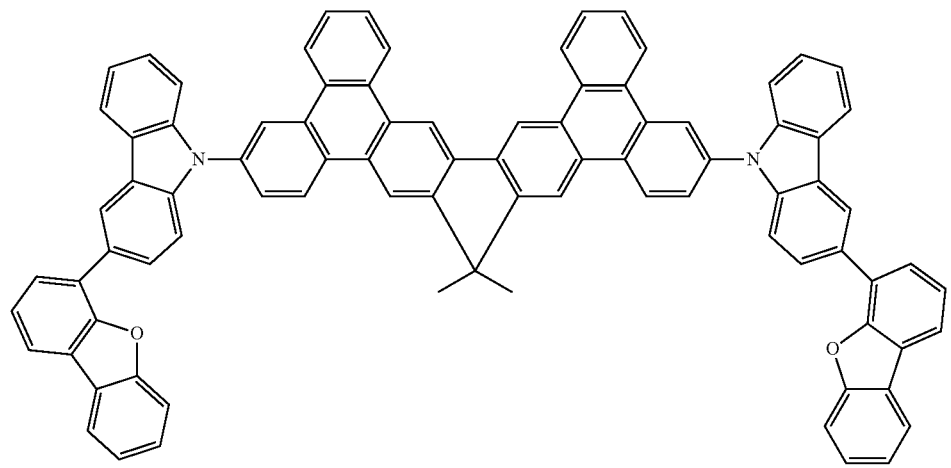

-continued
III-47
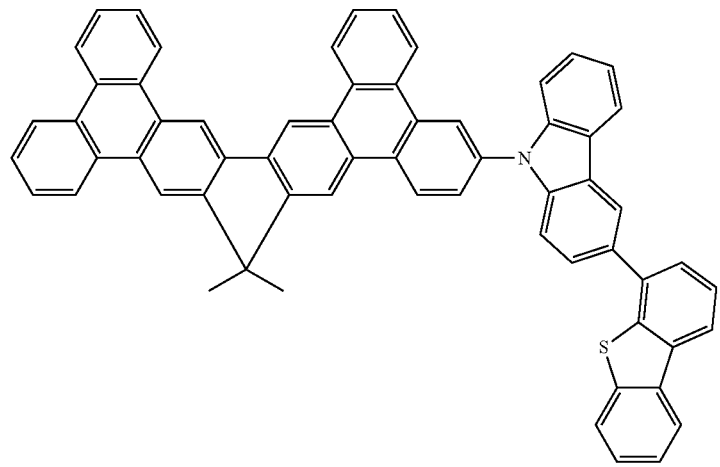
III-48
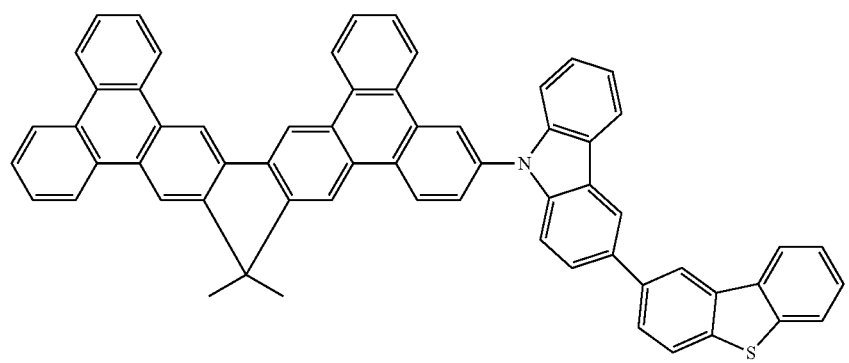
III-49
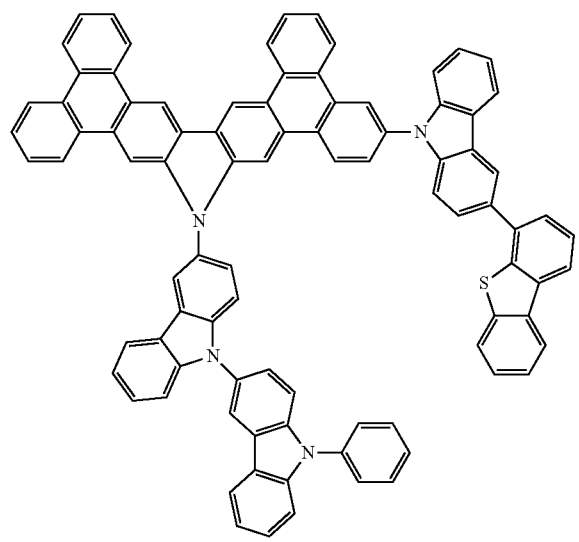
III-50
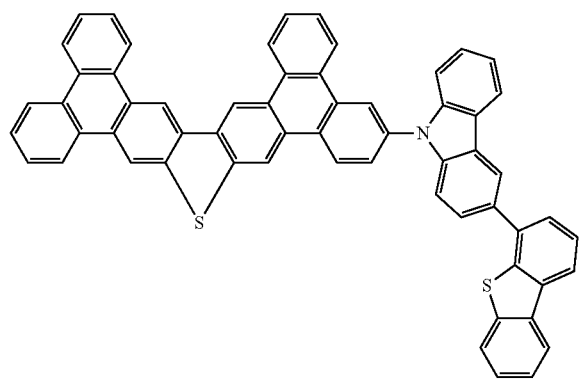

Detailed preparation for formula (I), formula (II) and formula (III) could be clarified by exemplary embodiments, but the present invention is not limited to exemplary embodiments. EXAMPLE 1~4 show the preparation of important intermediate of novel ditriphenylene skeleton for the present invention. EXAMPLE 5~13 show the detailed preparation for some EXAMPLES for formula (I), formula (II) and formula (III). EXAMPLE 14 and 15 show the fabrication of Organic EL device and I-V-B, half-life time of Organic EL device testing report.

Example 1

Synthesis of Intermediate II-a

Synthesis of 5-methoxybiphenyl-2-ylboronic acid

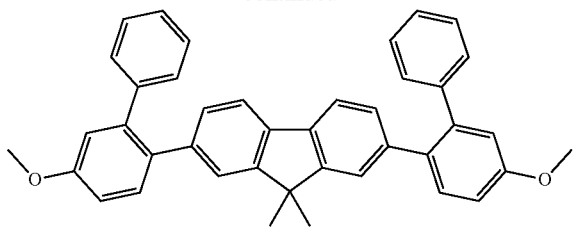

An excess of 1.6M n-BuLi in hexane (50 mL, 80 mmol) was added to a solution of 2-bromo-5-methoxybiphenyl (19.1 g, 72.7 mmol) in 350 ml dry tetrahydrofuran at −78° C. under N₂. The reaction mixture was then maintained at 0° C. for 1 h before cooling to −78° C., trimethylborate (10.4 g, 100 mmol) was added dropwise, the solution was then warmed slowly to room temperature and stirred for 24 h. 2N HCl (150 ml) was added and then the mixture was stirred for a further 1 h. The reaction mixture was extracted with ethyl acetate and water, dried with anhydrous magnesium sulfate, the solvent was evaporated in vacuum, and the residue was crystallized from n-hexane to give 9.5 g of the 5-methoxybiphenyl-2-ylboronic acid as a white solid (57%).

Synthesis of 2,7-bis(5-methoxybiphenyl-2-yl)-9,9-dimethyl-9H-fluorene

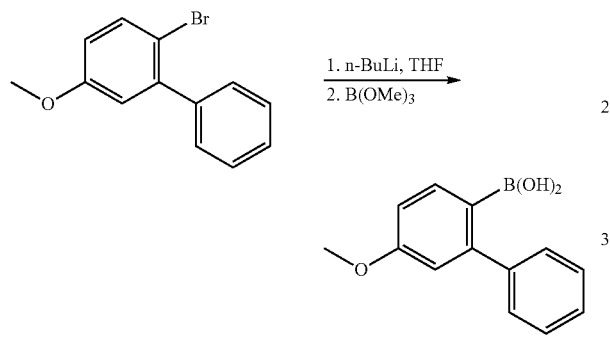

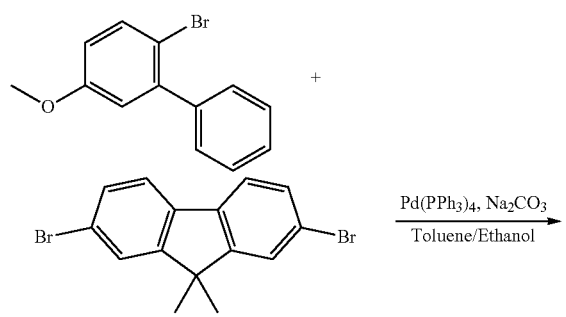

A mixture of 3.52 g (10 mmol) of 2,7-dibromo-9,9-dimethyl-9H-fluorene, 5.5 g (24 mmol) of 5-methoxybiphenyl-2-ylboronic acid, 0.12 g (0.1 mmol) of tetrakis(triphenylphosphine)palladium, 15 ml of 2M Na₂CO₃, 20 ml of EtOH and 60 ml toluene was degassed and placed under nitrogen, and then heated at 110° C. for 8 h. After finishing the reaction, the mixture was allowed to cool to room temperature. The reaction mixture was extracted with ethyl acetate and water, dried with anhydrous magnesium sulfate, the solvent was evaporated in vacuum. The residue was purified by column chromatography on silica(hexane-dichloromethane) afforded a white solid (3.7 g, 6.7 mmol, 67%); ¹H NMR (CDCl₃, 400 MHz): chemical shift (ppm) 7.57 (d, J=8.00 Hz, 2H), 7.45 (d, J=9.20 Hz, 2H), 7.21~7.14 (m, 12H), 7.00~6.98 (m, 4H), 6.88 (s, 2H), 3.89 (s, 6H), 0.89 (s, 6H).

Synthesis of Intermediate II-a

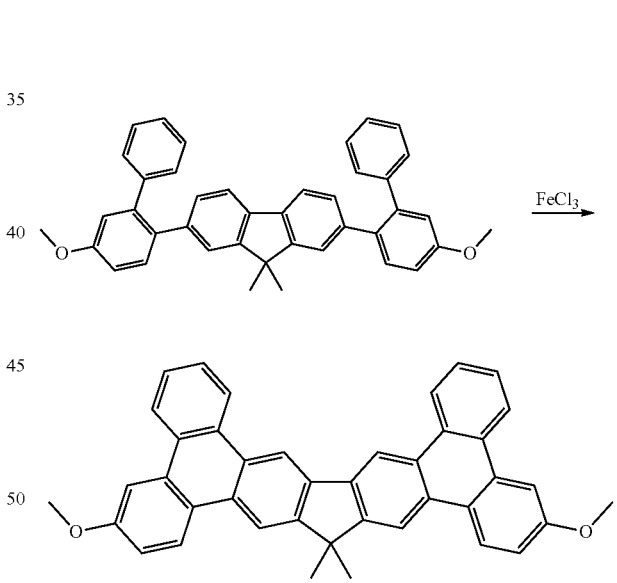

In a 1000 ml three-necked flask that had been deaerated and filled with nitrogen, 3.7 g (6.7 mmol) of 2,7-bis(5-methoxybiphenyl-2-yl)-9,9-dimethyl-9H-fluorene was dissolved in anhydrous dichloromethane (400 ml), 10.9 g (67 mmol) iron (III)chloride was then added, and the mixture was stirred one hour. Methanol 100 ml were added to the mixture and the organic layer was separated and the solvent removed in vacuum. The residue was purified by column chromatography on silica(hexane-dichloromethane) afforded a white solid (3.2 g, 5.8 mmol, 87%); ¹H NMR (CDCl₃, 400 MHz): chemical shift (ppm) 9.20 (s, 2H), 8.95 (d, J=8.00 Hz, 2H), 8.71 (d, J=9.20 Hz, 2H), 8.66 (s, 2H), 8.63 (d, J=8.00 Hz, 2H), 8.09 (s, 2H), 7.79~7.69 (m, 4H), 7.34 (d, J=8.00 Hz, 2H), 4.08 (s, 6H), 1.82 (s, 6H).

Example 2

Synthesis of Intermediate II-b

Synthesis of 2-bromo-7-(5-methoxybiphenyl-2-yl)-9,9-dimethyl-9H-fluorene

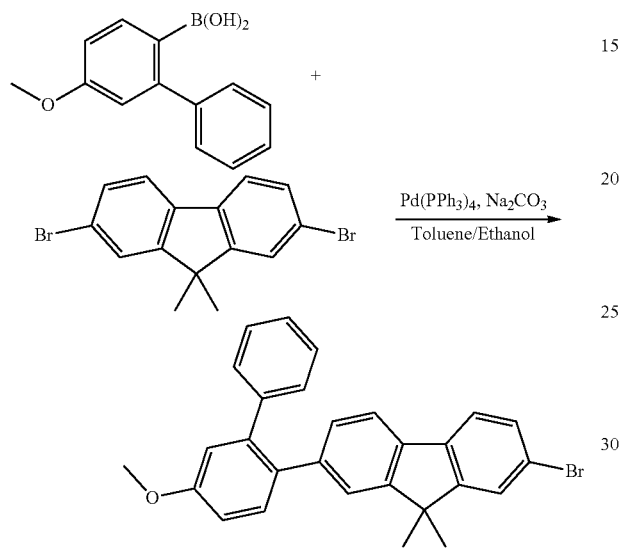

A mixture of 3.52 g (10 mmol) of 2,7-dibromo-9,9-dimethyl-9H-fluorene, 2.75 g (12 mmol) of 5-methoxybiphenyl-2-ylboronic acid, 0.12 g (0.1 mmol) of tetrakis(triphenylphosphine)palladium, 15 ml of 2M Na$_2$CO$_3$, 20 ml of EtOH and 60 ml toluene was degassed and placed under nitrogen, and then heated at 110° C. for 8 h. After finishing the reaction, the mixture was allowed to cool to room temperature. The reaction mixture was extracted with ethyl acetate and water, dried with anhydrous magnesium sulfate, the solvent was evaporated in vacuum. The residue was purified by column chromatography on silica(hexane-dichloromethane) afforded a white solid (3.4 g, 7.5 mmol, 75%).

Synthesis of 2-(biphenyl-2-yl)-7-(5-methoxybiphenyl-2-yl)-9,9-dimethyl-9H-fluorene

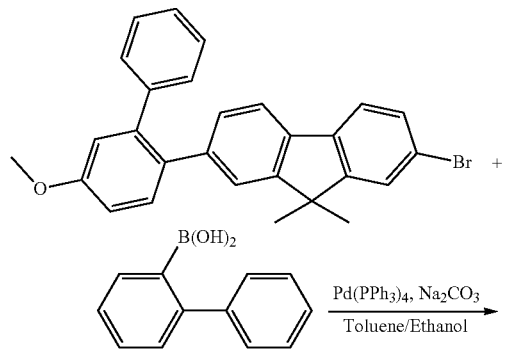

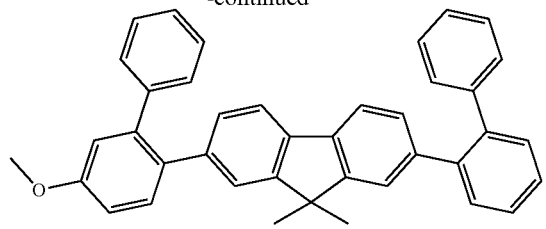

A mixture of 3.4 g (7.5 mmol) of 2-bromo-7-(5-methoxybiphenyl-2-yl)-9,9-dimethyl-9H-fluorene, 2 g (10 mmol) of biphenyl-2-ylboronic acid, 0.12 g (0.1 mmol) of tetrakis(triphenylphosphine)palladium, 15 ml of 2M Na$_2$CO$_3$, 20 ml of EtOH and 60 ml toluene was degassed and placed under nitrogen, and then heated at 110° C. for 8 h. After finishing the reaction, the mixture was allowed to cool to room temperature. The reaction mixture was extracted with ethyl acetate and water, dried with anhydrous magnesium sulfate, the solvent was evaporated in vacuum. The residue was purified by column chromatography on silica(hexane-dichloromethane) afforded a white solid (2.7 g, 5.1 mmol, 68%).

Synthesis of Intermediate II-b

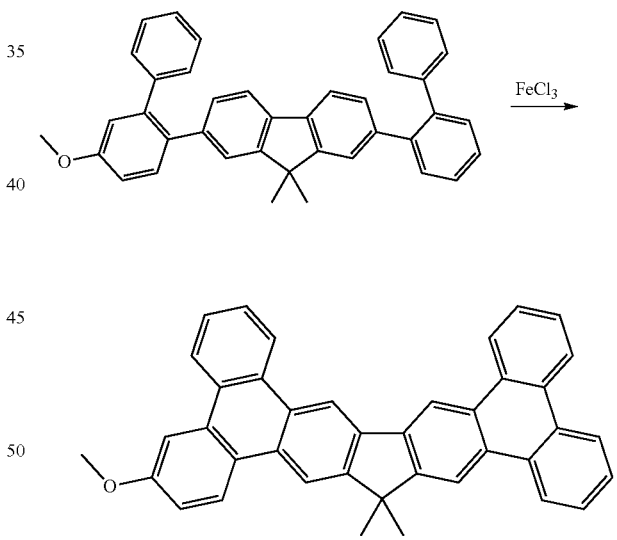

In a 1000 ml three-necked flask that had been deaerated and filled with nitrogen, 2.7 g (5.1 mmol) of 2-(biphenyl-2-yl)-7-(5-methoxybiphenyl-2-yl)-9,9-dimethyl-9H-fluorene was dissolved in anhydrous dichloromethane (300 ml), 8.3 g (51 mmol) iron(III)chloride was then added, and the mixture was stirred one hour. Methanol 100 ml were added to the mixture and the organic layer was separated and the solvent removed in vacuum. The residue was purified by column chromatography on silica(hexane-dichloromethane) afforded a white solid (2.5 g, 4.7 mmol, 93%); $^1$H NMR (CDCl$_3$, 400 MHz): chemical shift (ppm) 9.13 (s, 2H), 8.73~8.60 (m, 6H), 8.47 (d, J=8.00 Hz, 1H), 8.21 (d, J=8.00 Hz, 1H), 8.13 (d, J=8.00 Hz, 1H), 7.83-7.61 (m, 7H), 7.03 (d, J=8.00 Hz, 1H), 4.06 (s, 3H), 1.79 (s, 6H).

Example 3

Synthesis of Intermediate III-a

Synthesis of 2,7-dibromo-9-phenyl-9H-carbazole

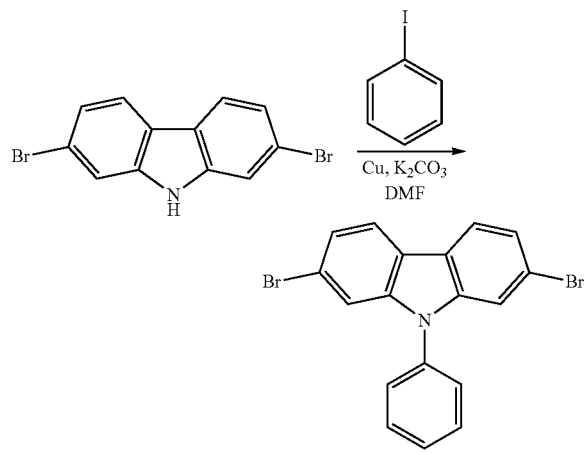

A mixture of 32.5 g (100 mmole) 2,7-dibromo-9H-carbazole, 20.4 g (100 mmole) iodobenzene, 9.5 g (150 mmole) of copper powder, 27.6 g (200 mmole) of potassium carbonate, and 600 ml dimethylformamide were heated at 130° C. under nitrogen overnight, then cooled to room temperature, the solution was filtered. The filtrate was extracted three times with dichloromethane and water, dried with anhydrous magnesium sulfate, the solvent was evaporated in vacuum. The residue was purified by column chromatography on silica (hexane-dichloromethane) afforded a white solid (31.3 g, 78 mmol, 78%).

Synthesis of 9-phenyl-2,7-bis(4,4,5,5-tetramethyl-1,3,2-dioxaborolan-2-yl)-9H-carbazole

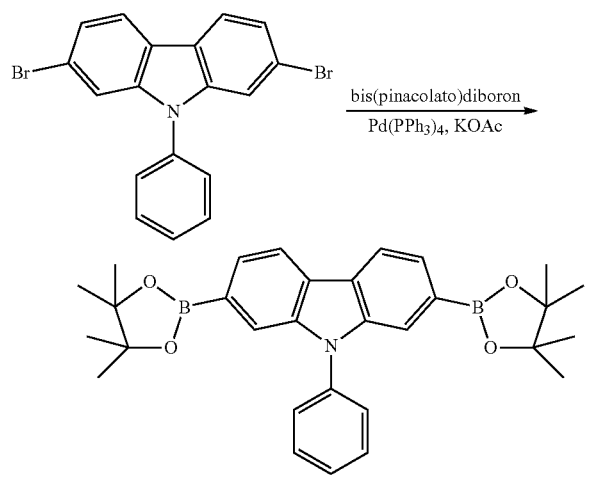

A mixture of 11.9 g (29.6 mmol) 2,7-dibromo-9-phenyl-9H-carbazole, 18.8 g (74 mmol) of bis(pinacolato)diboron, 0.7 g (0.6 mmol) of tetrakis(triphenylphosphine)palladium, 8.7 g (89 mmol) of potassium acetate, and 500 ml 1,4 dioxane was degassed and placed under nitrogen, and then heated at 90° C. for 24 h. After finishing the reaction, the mixture was allowed to cool to room temperature. The organic phase separated and washed with ethyl acetate and water. After drying over magnesium sulfate, the solvent was removed in vacuum. The residue was purified by column chromatography on silica (hexane-dichloromethane) to give product (8.6 g, 59%) as a white solid.

Synthesis of 2,7-bis(5-methoxybiphenyl-2-yl)-9-phenyl-9H-carbazole

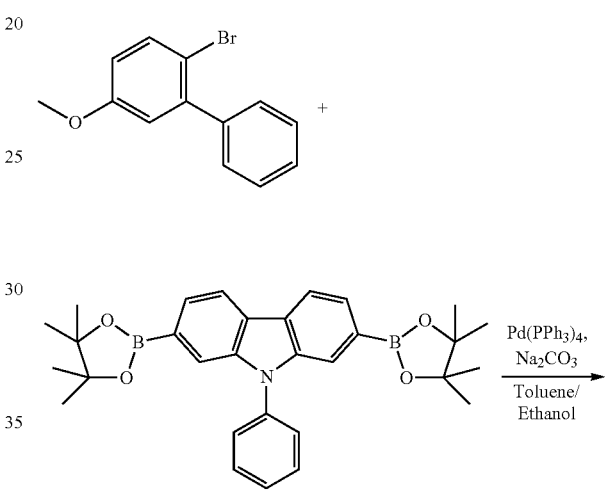

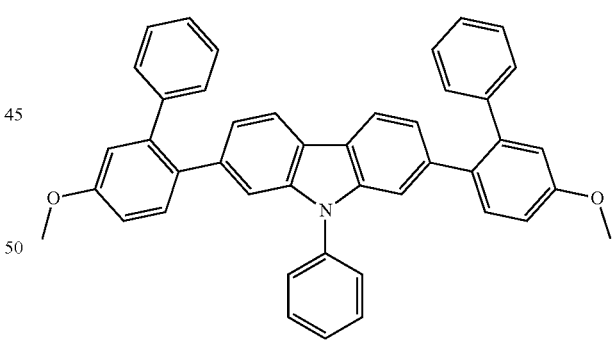

A mixture of 10 g (38.2 mmol) of 2-bromo-5-methoxybiphenyl, 8.6 g (17.4 mmol) of 9-phenyl-2,7-bis(4,4,5,5-tetramethyl-1,3,2-dioxaborolan-2-yl)-9H-carbazole, 0.4 g (0.35 mmol) of tetrakis(triphenylphosphine)palladium, 30 ml of 2M Na$_2$CO$_3$, 60 ml of EtOH and 150 ml toluene was degassed and placed under nitrogen, and then heated at 110° C. for 12 h. After finishing the reaction, the mixture was allowed to cool to room temperature. The reaction mixture was extracted with ethyl acetate and water, dried with anhydrous magnesium sulfate, the solvent was evaporated in vacuum. The residue was purified by column chromatography on silica(hexane-dichloromethane) afforded a white solid (7.1 g, 11.7 mmol, 67%).

Synthesis of Intermediate III-a

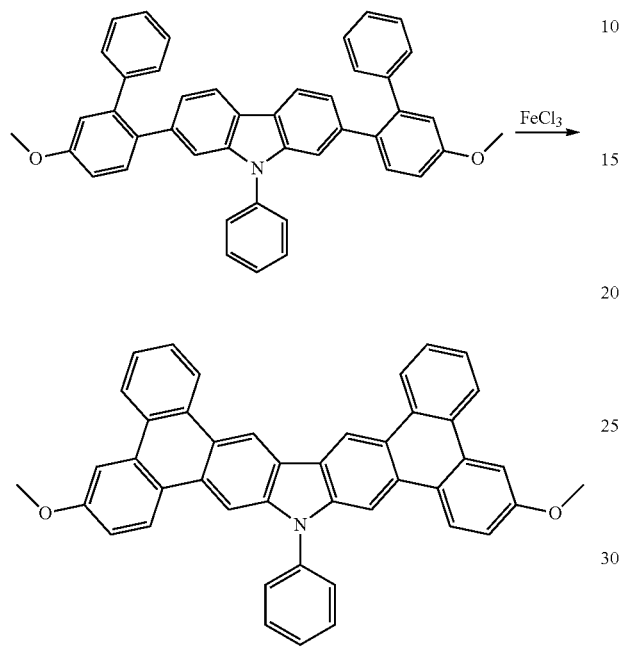

In a 2000 ml three-necked flask that had been deaerated and filled with nitrogen, 7.1 g (11.7 mmol) of 2,7-bis(5-methoxy-biphenyl-2-yl)-9-phenyl-9H-carbazole was dissolved in anhydrous dichloromethane (710 ml), 38 g (234 mmol) iron (III)chloride was then added, and the mixture was stirred one hour. Methanol 300 ml were added to the mixture and the organic layer was separated and the solvent removed in vacuum. The residue was purified by column chromatography on silica(hexane-dichloromethane) afforded a white solid (5.9 g, 84%); $^1$H NMR (CDCl$_3$, 400 MHz): chemical shift (ppm) 9.52 (s, 1H), 8.95 (d, J=8.00 Hz, 2H), 8.61~8.48 (m, 6H), 8.06 (s, 2H), 7.84~7.66 (m, 10H), 7.23 (d, J=8.00 Hz, 2H), 4.03 (s, 6H).

Example 4

Synthesis of Intermediate III-b

Synthesis of 2-bromo-7-(5-methoxybiphenyl-2-yl)-9-phenyl-9H-carbazole

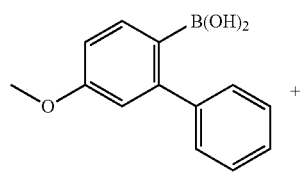

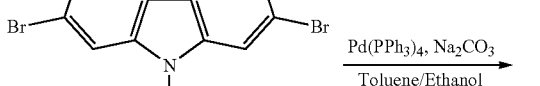

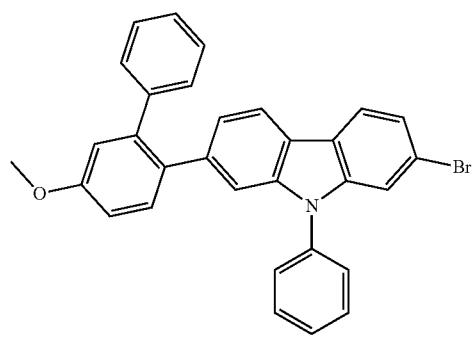

A mixture of 4 g (10 mmol) of 2,7-dibromo-9-phenyl-9H-carbazole, 75 g (12 mmol) of 5-methoxybiphenyl-2-ylboronic acid, 0.12 g (0.1 mmol) of tetrakis(triphenylphosphine)palladium, 15 ml of 2M Na$_2$CO$_3$, 20 ml of EtOH and 60 ml toluene was degassed and placed under nitrogen, and then heated at 110° C. for 8 h. After finishing the reaction, the mixture was allowed to cool to room temperature. The reaction mixture was extracted with ethyl acetate and water, dried with anhydrous magnesium sulfate, the solvent was evaporated in vacuum. The residue was purified by column chromatography on silica (hexane-dichloromethane) afforded a white solid (3 g, 5.9 mmol, 59%).

Synthesis of 2-(biphenyl-2-yl)-7-(5-methoxybiphenyl-2-yl)-9-phenyl-9H-carbazole

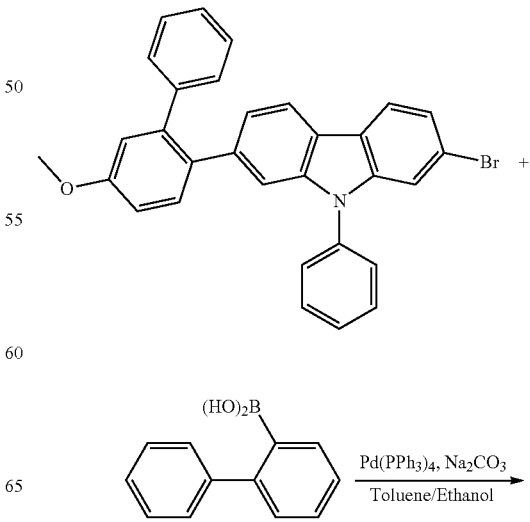

-continued

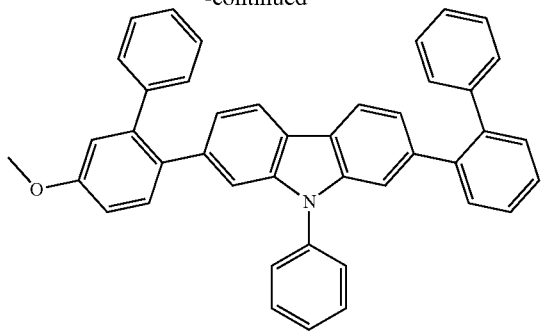

A mixture of 3 g (5.9 mmol) of 2-bromo-7-(5-methoxybiphenyl-2-yl)-9-phenyl-9H-carbazole, 1.5 g (7.7 mmol) of biphenyl-2-ylboronic acid, 0.12 g (0.1 mmol) of tetrakis(triphenylphosphine)palladium, 15 ml of 2M $Na_2CO_3$, 20 ml of EtOH and 60 ml toluene was degassed and placed under nitrogen, and then heated at 110° C. for 8 h. After finishing the reaction, the mixture was allowed to cool to room temperature. The reaction mixture was extracted with ethyl acetate and water, dried with anhydrous magnesium sulfate, the solvent was evaporated in vacuum. The residue was purified by column chromatography on silica(hexane-dichloromethane) afforded a white solid (2 g, 3.4 mmol, 58%).

Synthesis of intermediate III-b

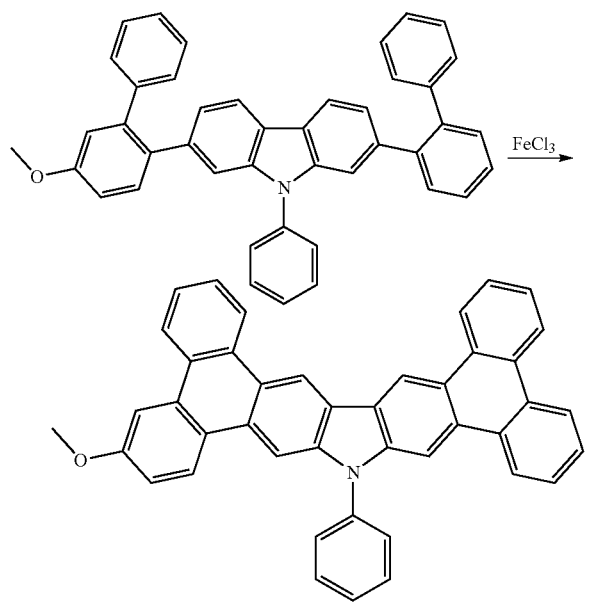

In a 1000 ml three-necked flask that had been deaerated and filled with nitrogen, 2 g (3.4 mmol) of 2-(biphenyl-2-yl)-7-(5-methoxybiphenyl-2-yl)-9-phenyl-9H-carbazole was dissolved in anhydrous dichloromethane (300 ml), 5.5 g (34 mmol) iron(III)chloride was then added, and the mixture was stirred one hour. Methanol 100 ml were added to the mixture and the organic layer was separated and the solvent removed in vacuum. The residue was purified by column chromatography on silica(hexane-dichloromethane) afforded a white solid (1.74 g, 3 mmol, 89%); $^1$H NMR (CDCl$_3$, 400 MHz): chemical shift (ppm) 8.76~8.67 (m, 5H), 8.60 (s, 2H), 8.55 (d, J=8.00 Hz, 1H), 8.23 (d, J=8.00 Hz, 1H), 7.9~7.79 (m, 4H), 7.72~7.63 (m, 4H), 7.5~7.48 (m, 2H), 7.42~7.37 (m, 1H), 7.22~7.18 (m, 3H), 7.08 (d, J=8.00 Hz, 1H), 4.07 (s, 3H).

Example 5

Synthesis of Compound II-7

Synthesis of Step 1

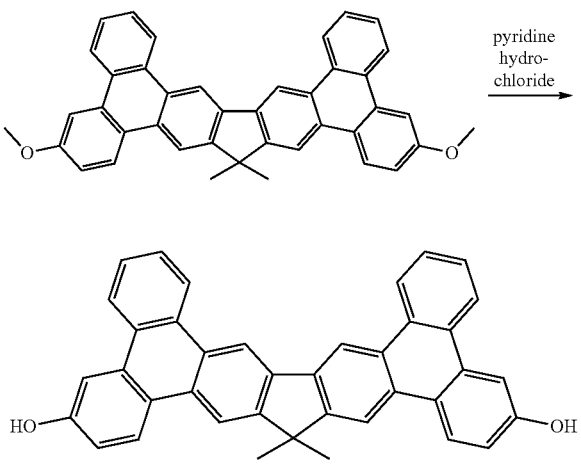

A mixture of 10 g (18 mmol) of Intermediate II-a, 31.2 g (270 mmol) of pyridine hydrochloride, was degassed and placed under nitrogen, and then heated at 220° C. for 6 h, the mixture was allowed to cool to room temperature and water was added. The resulting solid was filtered off, washed with water, and dried under high vacuum to give the product of Step 1 (8.6 g, 16.4 mmol, 91%)

Synthesis of Step 2

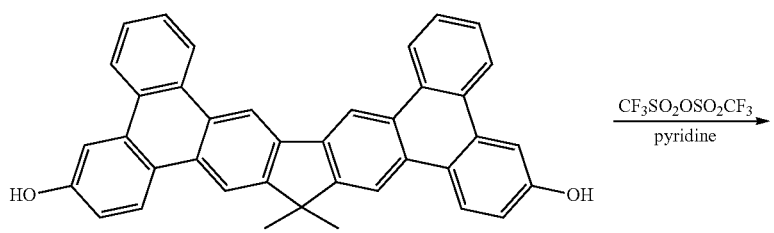

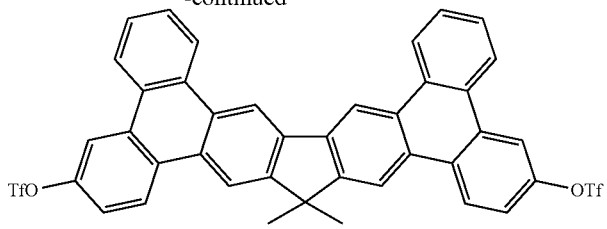

In a 1000 ml three-necked flask that had been degassed and filled with nitrogen, 8.6 g (16.4 mmol) of Step 1 product was dissolved in anhydrous dichloromethane (430 ml), 20 ml pyridine was then added, and the mixture was cooled in an ice salt bath, then 11 ml (65.6 mmol) of trifluoromethanesulfonic anhydride in 50 ml dichloromethane was added dropwise to the solution under nitrogen. The reaction was allowed to proceed for 6 hours and quenched by adding methanol and water. The resulting solid was filtered off, washed with water, methanol and dichloromethane, the residue product was recrystallized from toluene to get 7.4 g (9.3 mmol, 57%) of Step 2 product.

Synthesis of Compound II-7

A mixture of 7.4 g (9.3 mmole) product of Step 2, 7.5 g (28 mmole) of dinaphthalen-2-ylamine, 0.18 g (0.2 mmole) of $pd_2(dba)_3$, 0.08 g (0.4 mmole) of tri-tert-butylphosphine, 2.7 g (27.9 mmole) of sodium tert-butoxide and o-xylene 100 ml were refluxed under nitrogen for 48 hours. Then, the solution was filtered at 130° C. To receive the filtrate, the o-xylene was removed under reduced pressure from the filtrate. The organic layer was extracted with dichloromethane and water, dried with anhydrous magnesium sulfate, the solvent was removed and the residue was purified by column chromatography on silica(hexane-dichloromethane) to give 4.3 g of compound II-7 (45%). MS (m/z, FAB$^+$): 1028.1; $^1$H NMR (CDCl$_3$, 400 MHz): chemical shift (ppm) 9.14 (s, 2H), 8.94 (d, J=8.00 Hz, 2H), 8.82 (s, 2H), 8.67 (d, J=9.20 Hz, 2H), 8.47 (d, J=8.00 Hz,

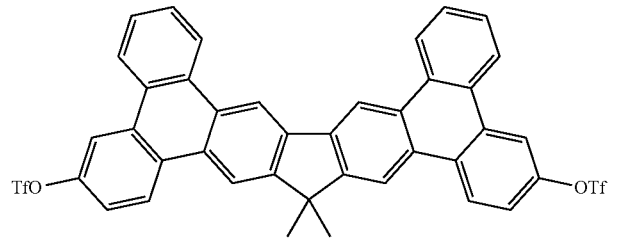

+

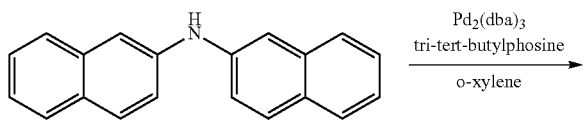

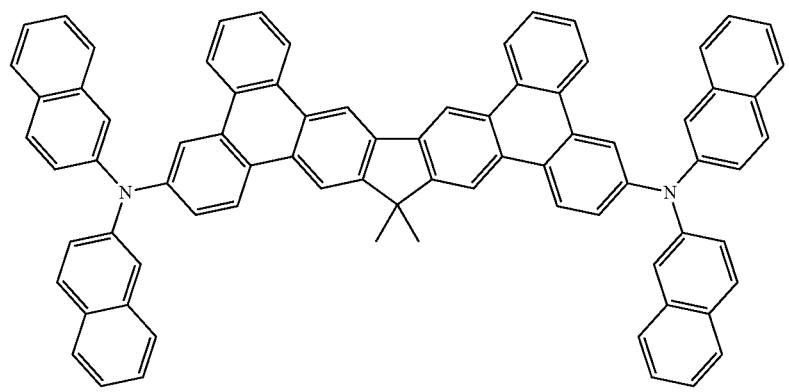

2H), 8.21 (d, J=8.00 Hz, 4H), 7.98~7.91 (m, 2H), 7.77~7.48 (m, 20H), 7.29~7.14 (m, 4H), 7.08~7.00 (m, 6H), 1.82 (s, 6H).

Example 6

Synthesis of Compound II-8

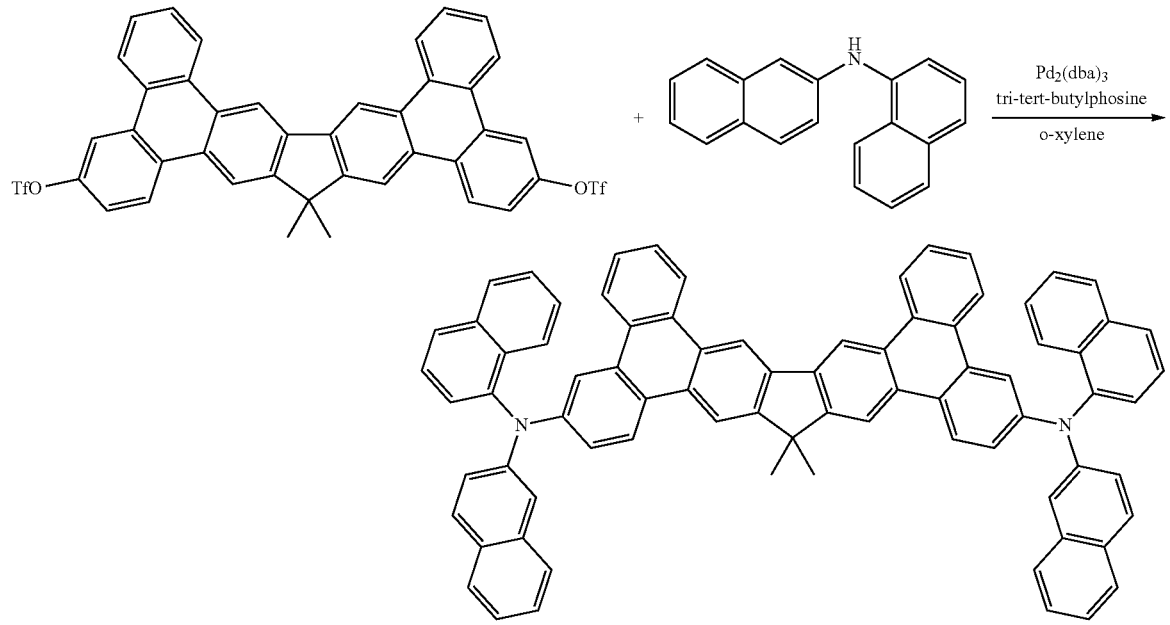

A mixture of 7.4 g (9.3 mmole) EXAMPLE 5 intermediate (from Step 2 product), 7.5 g (28 mmole) of N-(naphthalen-2-yl)naphthalene-1-amine, 0.18 g (0.2 mmole) of pd₂(dba)₃, 0.08 g (0.4 mmole) of tri-tert-butylphosphine, 2.7 g (27.9 mmole) of sodium tert-butoxide and o-xylene 100 ml were refluxed under nitrogen for 48 hours. Then, the solution was filtered at 130° C. To receive the filtrate, the o-xylene was removed under reduced pressure from the filtrate. The organic layer was extracted with dichloromethane and water, dried with anhydrous magnesium sulfate, the solvent was removed and the residue was purified by column chromatography on silica(hexane-dichloromethane) to give 5 g (45%) of the compound II-8. MS (m/z, FAB⁺): 1028.3; ¹H NMR (CDCl₃, 400 MHz): ¹H NMR (CDCl₃, 400 MHz): chemical shift (ppm) 9.14 (s, 2H), 8.94 (d, J=8.00 Hz, 2H), 8.82 (s, 2H), 8.67 (d, J=9.20 Hz, 2H), 8.47 (d, J=8.00 Hz, 2H), 8.21 (d, J=8.00 Hz, 4H), 7.91~7.48 (m, 22H), 7.29~7.14 (m, 4H), 7.08~7.00 (m, 6H), 1.82 (s, 6H).

Example 7

Synthesis of Compound II-27

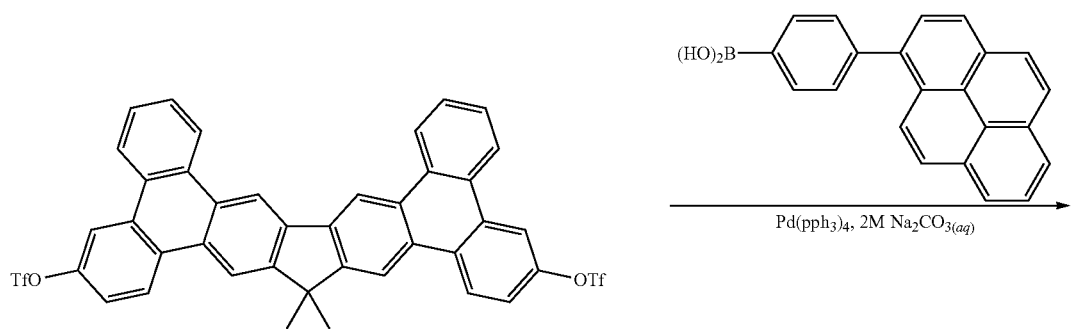

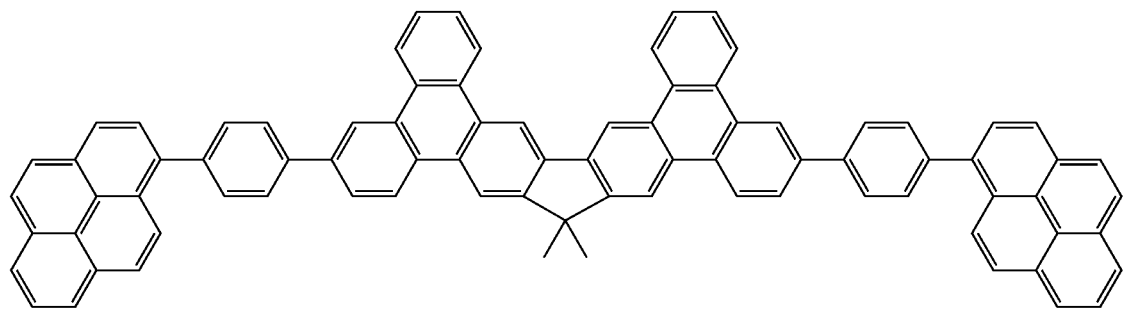

A mixture of 11 g (14 mmole) EXAMPLE 5 intermediate (from Step 2 product), 11.3 g (35 mmol) of 4-(pyren-1-yl) phenylboronic acid, 0.32 g (0.28 mmol) of tetrakis(triphenylphosphine)palladium, 25 ml of 2M $Na_2CO_3$, 50 ml of EtOH and 150 ml toluene was degassed and placed under nitrogen, and then heated at 100° C. for 12 h. After finishing the reaction, the mixture was allowed to cool to room temperature. Then 500 ml MeOH was added, while stirring and the precipitated product was filtered off with suction. To give 6.3 g (yield 43%) of yellow compound II-27 which was recrystallized from toluene. MS (m/z, FAB+): 1046.7; $^1$H NMR ($CDCl_3$, 400 MHz): chemical shift (ppm) 9.17 (s, 2H), 8.96 (s, 2H), 8.76~8.68 (m, 4H), 8.50 (s, 2H), 8.35 (d, J=8.00 Hz, 2H), 8.14~7.85 (m, 16H), 7.74~7.51 (m, 10H), 7.41~7.28 (m, 6H), 1.80 (s, 6H).

Example 8

Synthesis of Compound II-29

Synthesis of Step 1

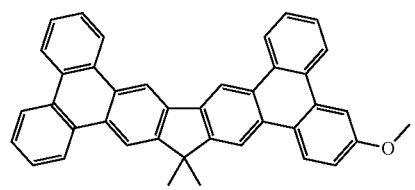

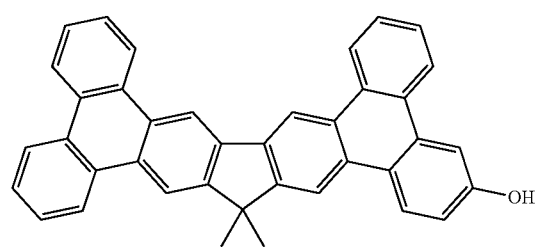

A mixture of 9.4 g (18 mmol) of Intermediate II-b, 31.2 g (270 mmol) of pyridine hydrochloride, was degassed and placed under nitrogen, and then heated at 220° C. for 6 h, the mixture was allowed to cool to room temperature and water was added. The resulting solid was filtered off, washed with water and dried under high vacuum to give the product of Step 1 (8 g, 15.7 mmol, 87%).

Synthesis of Step 2

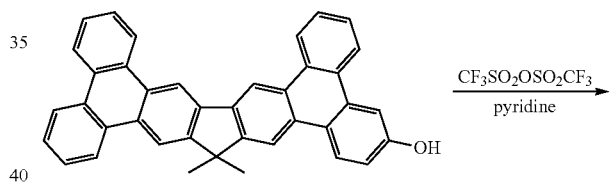

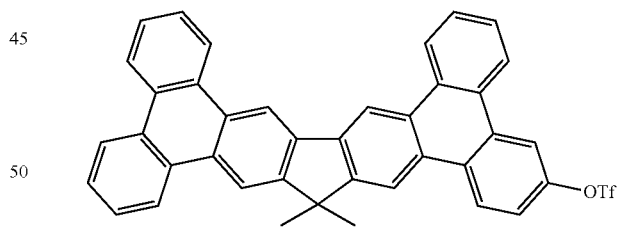

In a 1000 ml three-necked flask that had been degassed and filled with nitrogen, 8 g (15.7 mmol) of Step 1 product was dissolved in anhydrous dichloromethane (400 ml), 8 ml pyridine was then added, and the mixture was cooled in an ice salt bath. 5.3 ml (31.4 mmol) trifluoromethane sulfonic anhydride in 43 ml dichloromethane was added dropwise to the solution under nitrogen. The reaction was allowed to proceed for 6 hours and quenched by adding methanol and water. The resulting solid was filtered off, washed with water, methanol and dichloromethane, the residue product was recrystallized from toluene to obtain 7.4 g (11.5 mmol, 73%) of Step 2 product.

Synthesis of Compound II-29

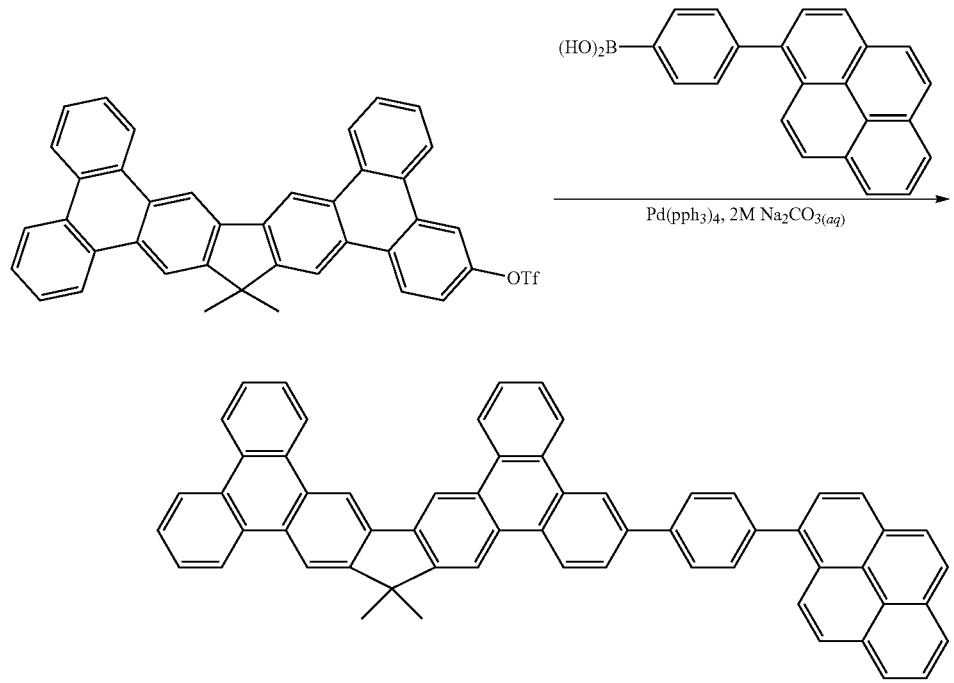

A mixture of 7.4 g (11.5 mmol) of Step 2 product, 4.4 g (13.8 mmol) of 4-(pyren-1-yl)phenylboronic acid, 0.27 g (0.24 mmol) of tetrakis(triphenyl phosphine)palladium, 24 ml of 2M Na$_2$CO$_3$, 40 ml of EtOH and 100 ml toluene was degassed and placed under nitrogen, and then heated at 100° C. for 24 h. After finishing the reaction, the mixture was allowed to cool to room temperature. The crystalline precipitates was filtrated and rinsed with 50 ml of hexane and 50 ml of dichloromethane. The product was purified by sublimation to get 4.5 g (yield 51%) of Compound II-29. MS (m/z, FAB$^+$): 770.1; $^1$H NMR (CDCl$_3$, 400 MHz): chemical shift (ppm) 9.14 (s, 2H), 8.92 (s, 1H), 8.74~8.62 (m, 4H), 8.58 (s, 1H), 8.47 (d, J=8.00 Hz, 1H), 8.23 (d, J=8.00 Hz, 1H), 8.19 (d, J=8.00 Hz, 1H), 8.12-7.97 (m, 5H), 7.93 (d, J=2.40 Hz, 1H), 7.78~7.70 (m, 3H), 7.67 (d, J=8.00 Hz, 1H), 7.61~7.50 (m, 6H), 7.46~7.38 (m, 5H), 1.82 (s, 6H).

Example 9

Synthesis of Compound III-8

Synthesis of 3,7-bis(5-methoxybiphenyl-2-yl)dibenzo[b,d]thiophene

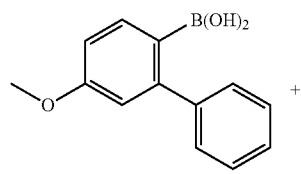

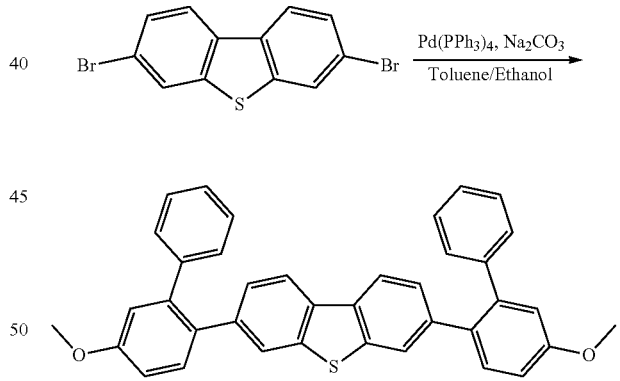

A mixture of 3.42 g (10 mmol) of 3,7-dibromodibenzo[b,d]thiophene, 5.5 g (24 mmol) of 5-methoxybiphenyl-2-ylboronic acid, 0.12 g (0.1 mmol) of tetrakis(triphenylphosphine)palladium, 15 ml of 2M Na$_2$CO$_3$, 20 ml of EtOH and 60 ml toluene was degassed and placed under nitrogen, then heated at 110° C. for 8 h. After finishing the reaction, the mixture was allowed to cool to room temperature. The reaction mixture was extracted with ethyl acetate and water, dried with anhydrous magnesium sulfate, the solvent was evaporated in vacuum. The residue was purified by column chromatography on silica(hexane-dichloromethane) to afford a white solid (4.4 g, 8.1 mmol, 81%).

77
Synthesis of 6,14-dimethoxyditriphenyleno[2,3-b:2',3'-d]thiophene

78
Synthesis of ditriphenyleno[2,3-b:2',3'-d]thiophene-6,14-diol

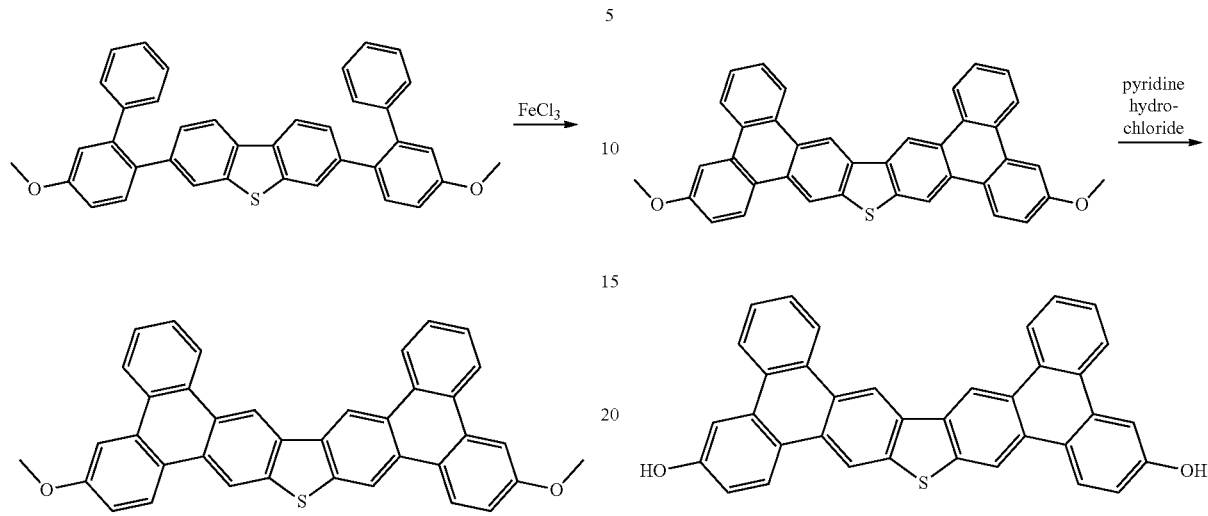

In a 1000 ml three-necked flask that had been deaerated and filled with nitrogen, 4.4 g (8.1 mmol) of 3,7-bis(5-methoxy-biphenyl-2-yl)dibenzo[b,d]thiophene was dissolved in anhydrous dichloromethane (400 ml), 13.2 g (81 mmol) iron(III) chloride was then added, and the mixture was stirred one hour. Methanol 200 ml were added to the mixture and the organic layer was separated and the solvent removed in vacuum. The residue was purified by column chromatography on silica(hexane-dichloromethane) afforded a white solid (4.1 g, 7.5 mmol, 93%).

A mixture of 9.8 g (18 mmol) of 6,14-dimethoxyditriphenyleno[2,3-b:2',3'-d]thiophene, 31.2 g (270 mmol) of pyridine hydrochloride, was degassed and placed under nitrogen, and then heated at 220° C. for 6 h, the mixture was allowed to cool to room temperature and water was added. The resulting solid was filtered off, washed with water, and dried under high vacuum to give the product (8.2 g, 15.8 mmol, 88%).

Synthesis of ditriphenyleno[2,3-b:2',3'-d]thiophene-6,14-diyl-bis(trifluoromethanesulfonate)

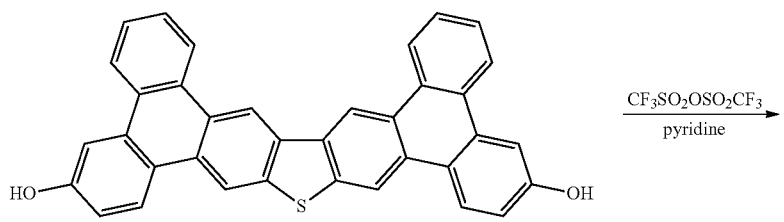

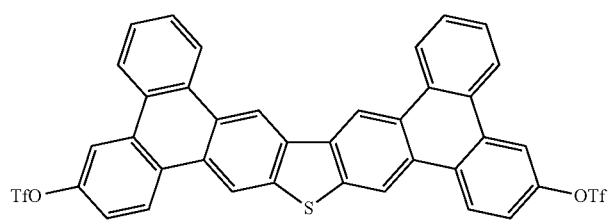

In a 1000 ml three-necked flask that had been degassed and filled with nitrogen, 8.2 g (15.8 mmol) of ditriphenyleno[2,3-b:2',3'-d]thiophene-6,14-diol was dissolved in anhydrous dichloromethane (420 ml), 20 ml pyridine was then added, and the mixture was cooled in an ice salt bath. 10.5 ml (63.2 mmol)trifluoromethanesulfonic anhydride in 30 ml dichloromethane was added dropwise to the solution under nitrogen. The reaction was allowed to proceed for 6 hours and quenched by adding methanol and water. The resulting solid was filtered off, washed with water, methanol and dichloromethane. The residue product was recrystallized from toluene to obtain 9.6 g (12.3 mmol, 78%) product.

Synthesis of 6,14-bis(3-(dibenzo[b,d]thiophen-4-yl)phenyl)ditriphenyleno[2,3-b:2',3'-d]thiophene A mixture of 11 g (14 mmol) of ditriphenyleno[2,3-b:2',3'-d]thiophene-6,14-diylbis(trifluoromethanesulfonate), 10.6 g (35 mmol) of 3-(dibenzo[b,d]thiophen-4-yl)phenylboronicacid, 0.32 g (0.28 mmol) of tetrakis(triphenylphosphine)palladium, 25 ml of 2M Na$_2$CO$_3$, 50 ml of EtOH and 150 ml toluene was degassed and placed under nitrogen, and then heated at 100° C. for 12 h. After finishing the reaction, the mixture was allowed to cool to room temperature. The crystalline precipitates was filtrated and rinsed with 50 ml of methanol and 50 ml of dichloromethane. The product was purified by sublimation to get 5.2 g of Compound III-8 (yield 37%). MS (m/z, FAB$^+$): 1000.1; $^1$H NMR (CDCl$_3$, 400 MHz): chemical shift (ppm) 9.03 (s, 2H), 8.91 (s, 2H), 8.85~8.77 (m, 6H), 8.45 (d, J=8.00 Hz, 2H), 8.40 (s, 2H), 8.33-8.22 (m, 4H), 8.05~7.96 (m, 2H), 7.87 (d, J=8.00 Hz, 2H), 7.74 (d, J=8.00 Hz, 2H), 7.68~7.46 (m, 14H), 7.35 (t, J=8.00 Hz, 2H).

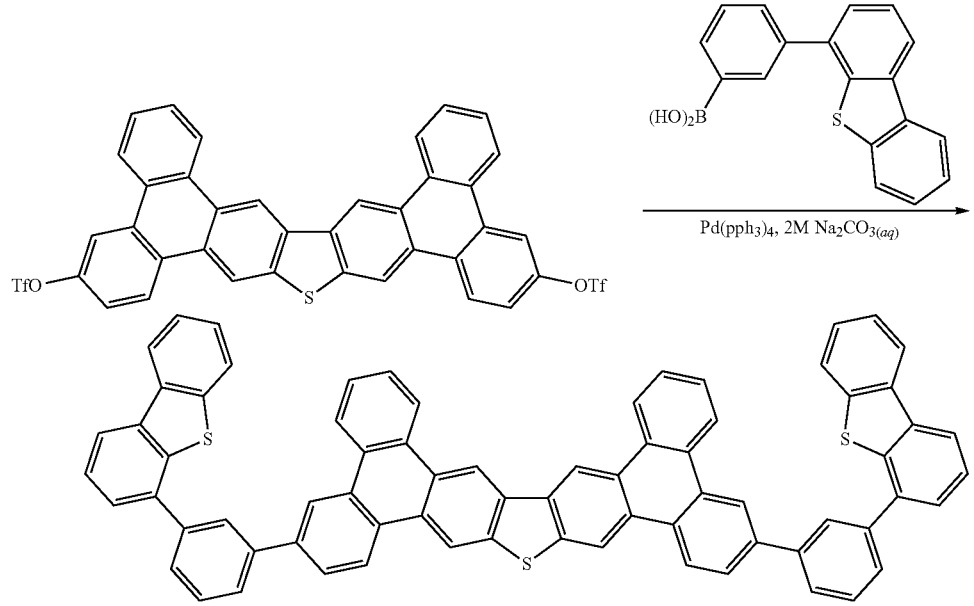

Example 10

Synthesis of Compound III-29

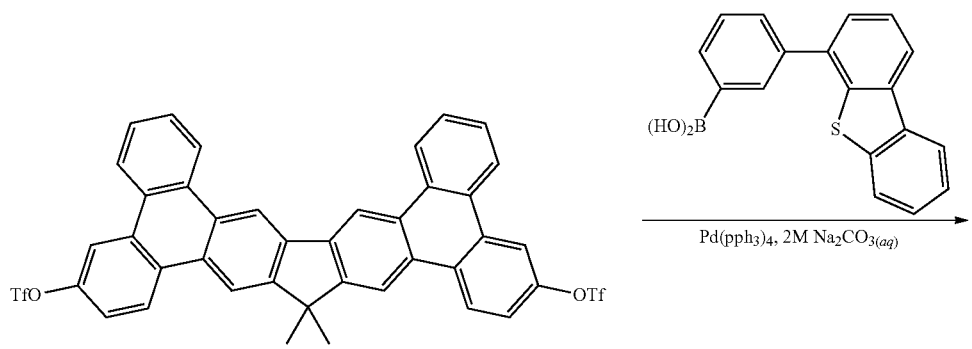

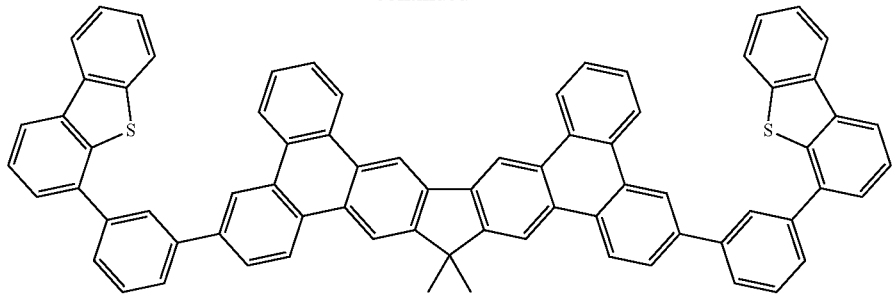

A mixture of 11 g (14 mmol) of EXAMPLES intermediate (from Step 2 product), 10.6 g (35 mmol) of 3-(dibenzo[b,d]thiophen-4-yl)phenylboronic acid, 0.32 g (0.28 mmol) of tetrakis(triphenylphosphine)palladium, 25 ml of 2M $Na_2CO_3$, 50 ml of EtOH and 150 ml toluene was degassed and placed under nitrogen, and then heated at 100° C. for 12 h. After finishing the reaction, the mixture was allowed to cool to room temperature. Then 200 ml MeOH was added, while stirring and the precipitated product was filtered off with suction to give 6.9 g (yield 49%) of yellow Compound III-29 which was recrystallized from toluene. MS (m/z, FAB+): 1011.5; $^1$H NMR (CDCl$_3$, 400 MHz): chemical shift (ppm) 9.09 (s, 2H), 8.78~8.66 (m, 6H), 8.56 (s, 2H), 8.43 (d, J=8.00 Hz, 2H), 8.38 (s, 2H), 8.31~8.17 (m, 4H), 8.04~7.92 (m, 2H), 7.83~7.73 (m, 4H), 7.65~7.47 (m, 14H), 7.35~7.3 (m, 2H), 1.80 (s, 6H).

Example 11

Synthesis of Compound III-30

A mixture of 7.4 g (11.5 mmol) of EXAMPLE 8 intermediate (product from Step 2), 4.2 g (13.8 mmol) of 3-(dibenzo[b,d]thiophen-4-yl)phenyl boronicacid, 0.27 g (0.24 mmol) of tetrakis(triphenylphosphine)palladium, 24 ml of 2M $Na_2CO_3$, 40 ml of EtOH and 100 ml toluene was degassed and placed under nitrogen, and then heated at 100° C. for 24 h. After finishing the reaction, the mixture was allowed to cool to room temperature. The crystalline precipitates was filtrated and rinsed with 50 ml of hexane and 50 ml of dichloromethane. The product was purified by sublimation to get 4 g of Compound III-30. (yield 47%). MS (m/z, FAB+): 752.3; $^1$H NMR (CDCl$_3$, 400 MHz): chemical shift (ppm) 9.15 (s, 2H), 8.76~8.62 (m, 6H), 8.57 (s, 1H), 8.45 (d, J=8.00 Hz, 1H), 8.39 (s, 1H), 8.33~8.27 (m, 2H), 8.23 (d, J=8.00 Hz, 1H), 8.13 (d, J=8.00 Hz, 1H), 7.99~7.96 (m, 1H), 7.82~7.71 (m, 4H), 7.68~7.61 (m, 2H), 7.57~7.44 (m, 7H), 7.35 (t, J=8.00 Hz, 1H), 1.81 (s, 6H).

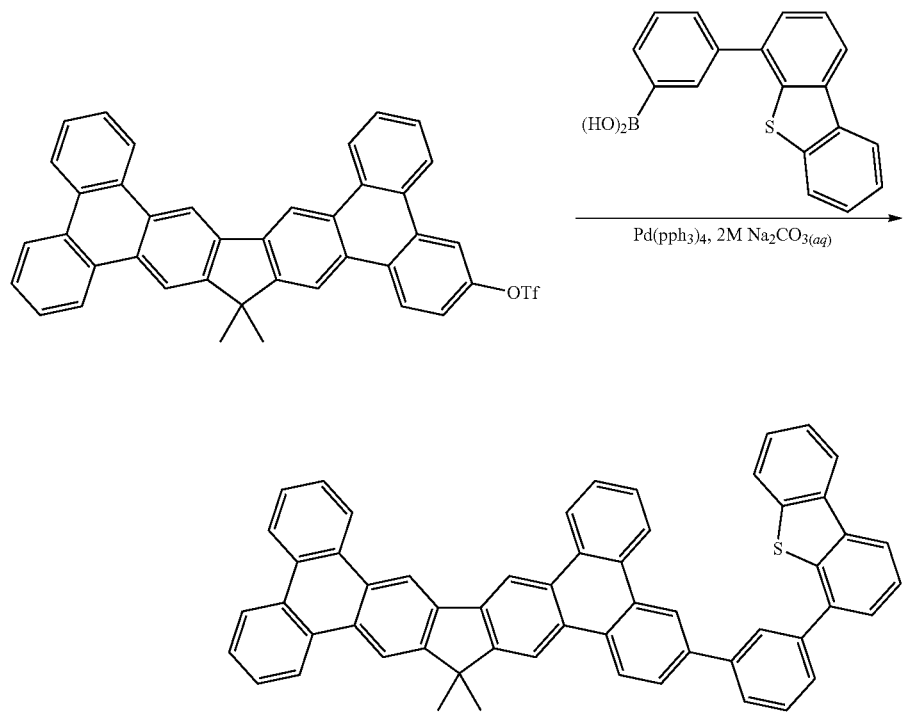 [SMILES: CC1(C)c2cc3c4ccccc4c4ccccc4c3cc2-c2cc3c4ccccc4c4cc(OS(=O)(=O)C(F)(F)F)ccc4c3cc21 ; OB(O)c1cccc(-c2cccc3c2sc2ccccc23)c1 ; CC1(C)c2cc3c4ccccc4c4ccccc4c3cc2-c2cc3c4ccccc4c4cc(-c5cccc(-c6cccc7c6sc6ccccc67)c5)ccc4c3cc21]

Example 12

Synthesis of Compound III-31

Synthesis of 3-bromo-9-(dibenzo[b,d]thiophen-4-yl)-9H-carbazole

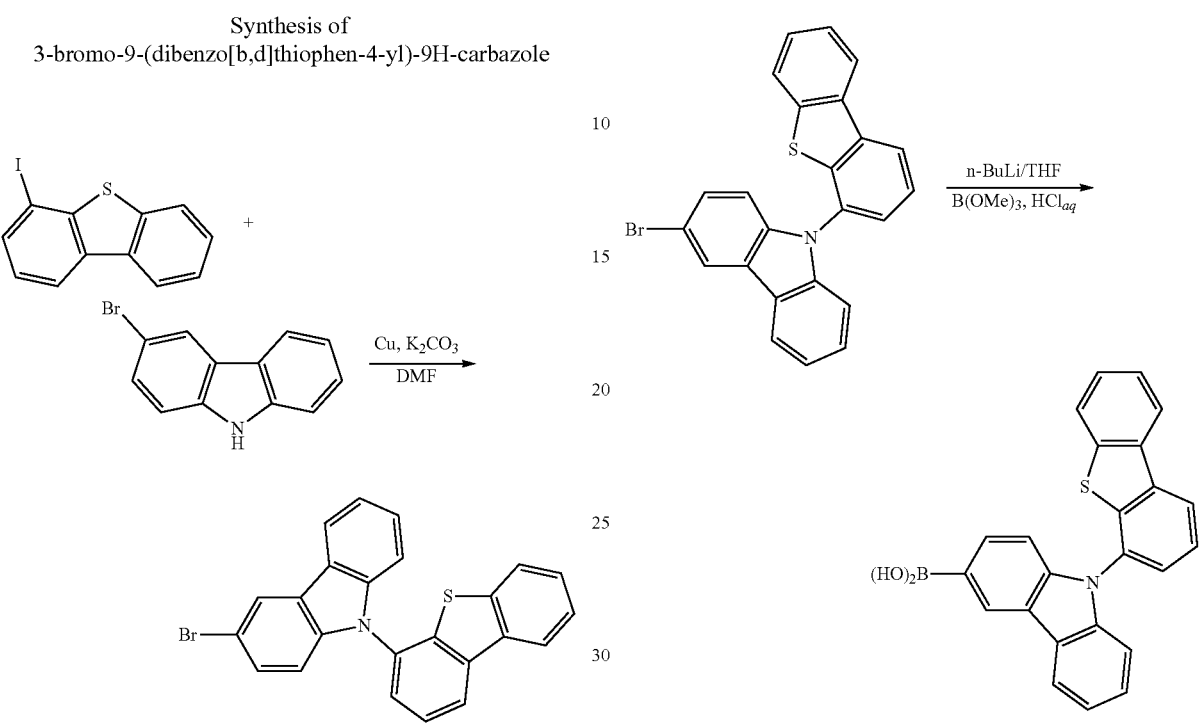

Synthesis of 9-(dibenzo[b,d]thiophen-4-yl)-9H-carbazol-3-yl boronic acid

A mixture of 10.9 g (35.1 mmol) 4-iododibenzo[b,d]thiophene, 8.6 g (35.1 mmol) of 3-bromo-9H-carbazole, 4.46 g (70.2 mmol) of Cu, 14.55 g (100.1 mmole) of $K_2CO_3$ was stirred in 100 ml dimethylformamide, the reaction mixture was then heat to 160° C. for about overnight under nitrogen. Then cooled to 100° C., the solution was filtered. To receive the filtrate, and most of the dimethylformamide was removed under reduced pressure from the filtrate. The distillation was extracted with ethyl acetate and water, dried with anhydrous magnesium sulfate, the solvent was removed and the residue was purified by column chromatography on silica(hexane-dichloromethane) to give product 8.7 g (58%).

An excess of 1.6M n-BuLi in hexane (14 mL, 22.3 mmol) was added to a solution of 3-bromo-9-(diberizo[b,d]thiophen-4-yl)-9H-carbazole (8.7 g, 20.3 mmol) in 100 ml dry tetrahydrofuran at −78° C. under $N_2$. The reaction mixture was then maintained at 0° C. for 1 h before cooling to −78° C. Trimethylborate (2.8 g, 26.4 mmol) was added dropwise; the solution was then warmed slowly to room temperature and stirred for 24 h. 2N HCl (50 ml) was added and then the mixture was stirred for a further 1 h. The reaction mixture was extracted with ethyl acetate and water, dried with anhydrous magnesium sulfate, the solvent was evaporated in vacuum, and the residue was crystallized from n-hexane to give the 9-(dibenzo[b,d]thiophen-4-yl)-9H-carbazol-3-ylboronic acid 4.7 g (59%)

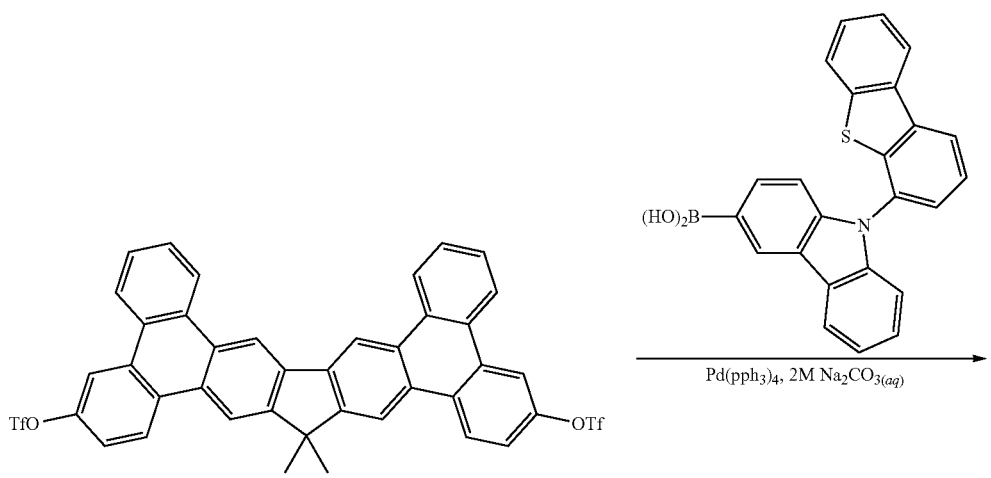

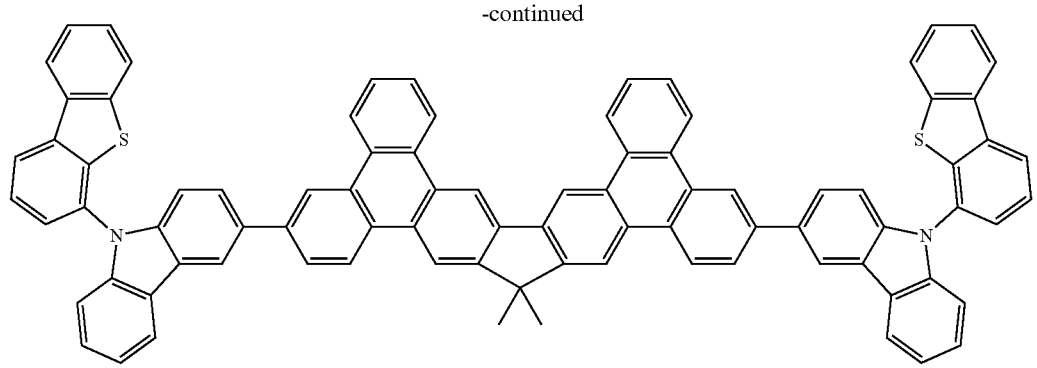

Synthesis of Compound III-31

A mixture of 6 g (7.6 mmol) EXAMPLES intermediate (from Step 2 product), 11.9 g (30.3 mmol) of 9-(dibenzo[b,d]thiophen-4-yl)-9H-carbazol-3-ylboronic acid, 0.18 g (0.15 mmol) of tetrakis(triphenylphosphine)palladium, 15 ml of 2M $Na_2CO_3$, 30 ml of EtOH and 100 ml toluene was degassed and placed under nitrogen, and then heated at 100° C. for 24 h. After finishing the reaction, the mixture was allowed to cool to room temperature. The crystalline precipitates was filtrated and rinsed with 50 ml of hexane and 50 ml of dichloromethane. The product was purified by sublimation to get 3.7 g of Compound III-31 (yield 41%). MS (m/z, $FAB^+$): 1188.1; $^1$H NMR ($CDCl_3$, 400 MHz): chemical shift 9.12 (s, 2H), 8.77-8.69 (m, 6H), 8.57 (s, 2H), 8.46 (d, J=8.00 Hz, 2H), 8.31-8.26 (m, 2H), 8.15 (d, J=9.20 Hz, 2H), 8.03~7.92 (m, 6H), 7.89~7.83 (m, 2H), 7.78~7.64 (m, 6H), 7.61~7.55 (m, 6H), 7.50~7.44 (m, 4H), 7.38 (d, J=8.00 Hz, 2H), 7.34 (d, J=8.00 Hz, 2H), 7.28 (t, J=8.00 Hz, 2H), 1.82 (s, 6H).

Example 13

Synthesis of Compound III-33

Synthesis of 9-(8-bromodibenzo[b,d]thiophen-2-yl)-9H-carbazole

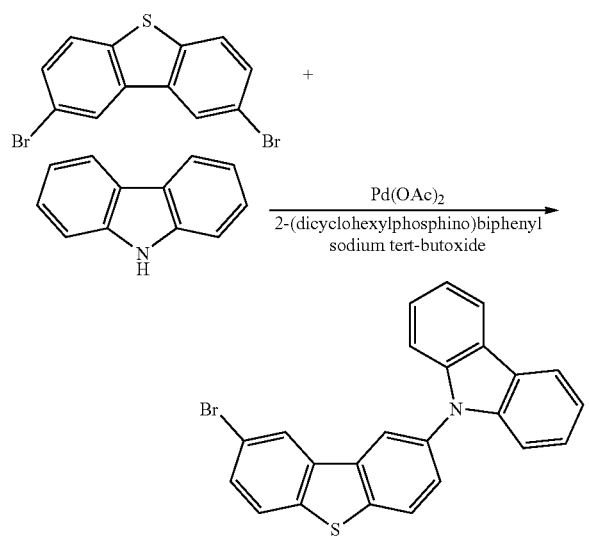

A mixture of 29.1 g (85.2 mmole) 2,8-dibromodibenzo[b,d]thiophene, 14.2 g (85.2 mmole) of carbazole, 0.12 g (0.54 mmole) of palladium(II) acetate, 0.4 g (1.14 mmol) of 2-(dicyclohexylphosphino)biphenyl, 10 g (104 mmole) sodium tert-butoxide and 300 ml toluene were refluxed under nitrogen for about overnight, then cooled to room temperature, the organic layer was extracted with ethyl acetate and water, dried with anhydrous magnesium sulfate, the solvent was removed and the residue was purified by column chromatography on silica(hexane-dichloromethane) to give product 18.6 g (51%).

Synthesis of 8-(9H-carbazol-9-yl)dibenzo[b,d]thiophen-2-yl boronic acid

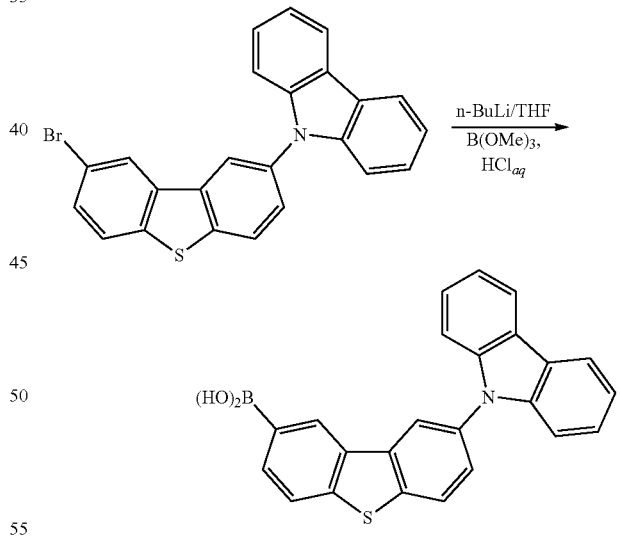

An excess of 1.6M n-BuLi in hexane (30 mL, 48 mmol) was added to a solution of 9-(8-bromodibenzo[b,d]thiophen-2-yl)-9H-carbazole (18.6 g, 43.4 mmol) in 500 ml dry tetrahydrofuran at −78° C. under $N_2$. The reaction mixture was then maintained at 0° C. for 1 h before cooling to −78° C. Trimethylborate (5.9 g, 56 mmol) was added dropwise, the solution was then warmed slowly to room temperature and stirred for 24 h. 2N HCl (100 ml) was added and then the mixture was stirred for a further 1 h. The reaction mixture was extracted with ethyl acetate and water, dried with anhydrous magnesium sulfate, the solvent was evaporated in vacuum, and the residue was crystallized from n-hexane to give 8-(9H-carbazol-9-yl)dibenzo[b,d]thiophen-2-ylboronic acid 11.9 g (63%).

Synthesis of Compound III-33

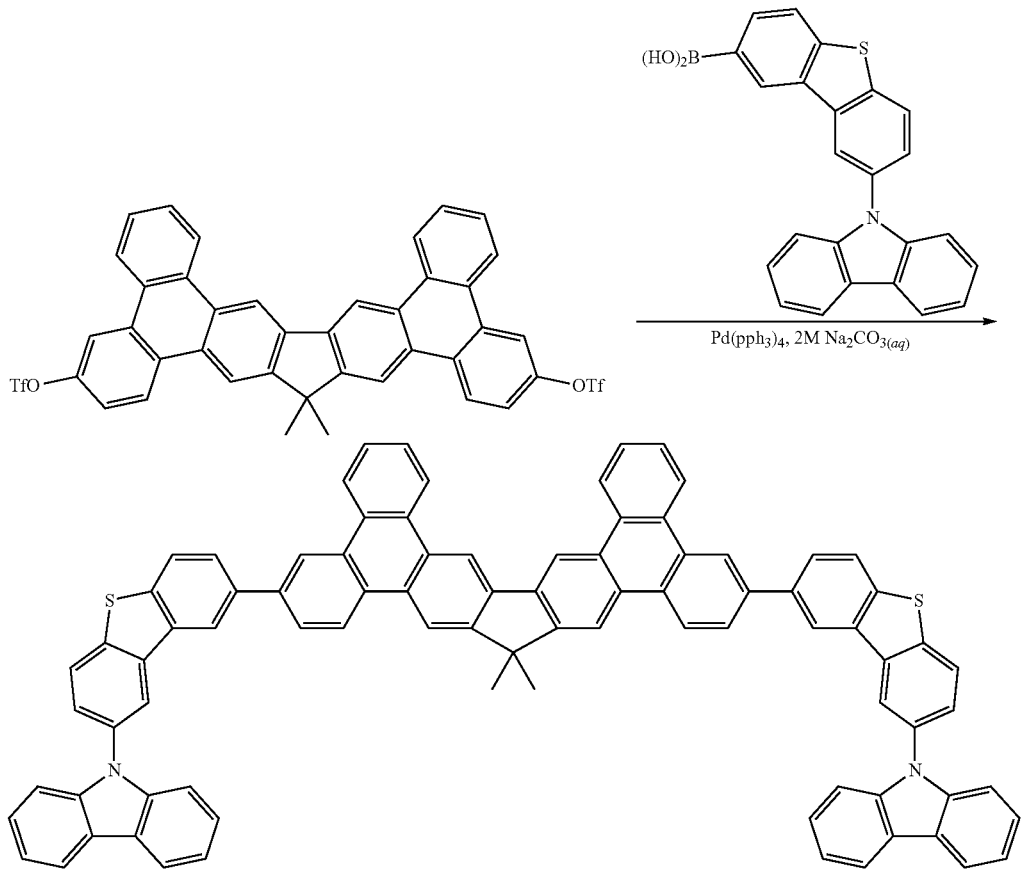

A mixture of 6 g (7.6 mmol) EXAMPLES intermediate (from Step 2 product), 11.9 g (30.3 mmol) of 8-(9H-carbazol-9-yl)dibenzo[b,d]thiophen-2-yl boronic acid, 0.18 g (0.15 mmol) of tetrakis(triphenylphosphine)palladium, 15 ml of 2M $Na_2CO_3$, 30 ml of EtOH and 100 ml toluene was degassed and placed under nitrogen, and then heated at 100° C. for 24 h. After finishing the reaction, the mixture was allowed to cool to room temperature. The crystalline precipitates was filtrated and rinsed with 50 ml of hexane and 50 ml of dichloromethane. The product was purified by sublimation to get 3.3 g of Compound III-33 (yield 37%). MS (m/z, FAB+): 1188.1; $^1$H NMR (CDCl$_3$, 400 MHz): chemical shift (ppm) 9.10 (s, 2H), 9.01-8.97 (m, 2H), 8.75-8.66 (m, 4H), 8.57 (s, 2H), 8.42 (d, J=8.00 Hz, 2H), 8.37 (s, 2H), 8.12 (s, 2H), 8.01 (d, J=9.20 Hz, 2H), 7.95 (d, J=9.20 Hz, 2H), 7.84 (d, J=8.00 Hz, 4H), 7.78 (d, J=8.00 Hz, 2H), 7.69 (d, J=8.00 Hz, 2H), 7.62 (d, J=8.00 Hz, 4H), 7.57~7.50 (m, 8H), 7.42 (d, J=8.00 Hz, 2H), 7.37-7.29 (m, 4H), 1.80 (s, 6H).

General Method of Producing Organic EL Device

ITO-coated glasses with 9~12 ohm/square in resistance and 120-160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2',3'-h]quinoxaline-2,3,6,7,10,1-hexacarbo nitrile(Hat-CN) is used as hole injection layer in this organic EL device. N,N'-Bis(naphthalene-1-yl)-N,N'-bis(phenyl)-benzidine(NPB) is most widely used as the hole transporting layer and 2,9-bis(naphthalene-2-yl)-4,7-diphenyl-1,10-phenanthroline(NBphen) is used as electron transporting material in organic EL device for its high thermal stability and long life-time than BPhen or BCP. For fluorescent emitting device, 1,1'-(9,9-dimethyl-9H-fluorene-2,7-diyl)dipyrene(DFDP) is used as emitting host and (E)-6-(4-(diphenylamin)styryl)-N,N-diphenylnaphthalen-2-amine (D1) is used as fluorescent emitting dopant. For phosphorescent emitting device, Bis(2-methyl-8-quinolinolate)-4-(phenylphenolato)aluminium(BAlq) is used as host of emitting layer and Tris(1-phenylisoquinoline)Iridium(III)Ir (piq)$_3$), Tris(2-phenylquinoline)iridium(III)(Ir(2-phq)$_3$) are used as phosphorescent dopant. The prior art of OLED materials for producing standard organic EL device and comparable material in this invention shown its chemical structure as following:

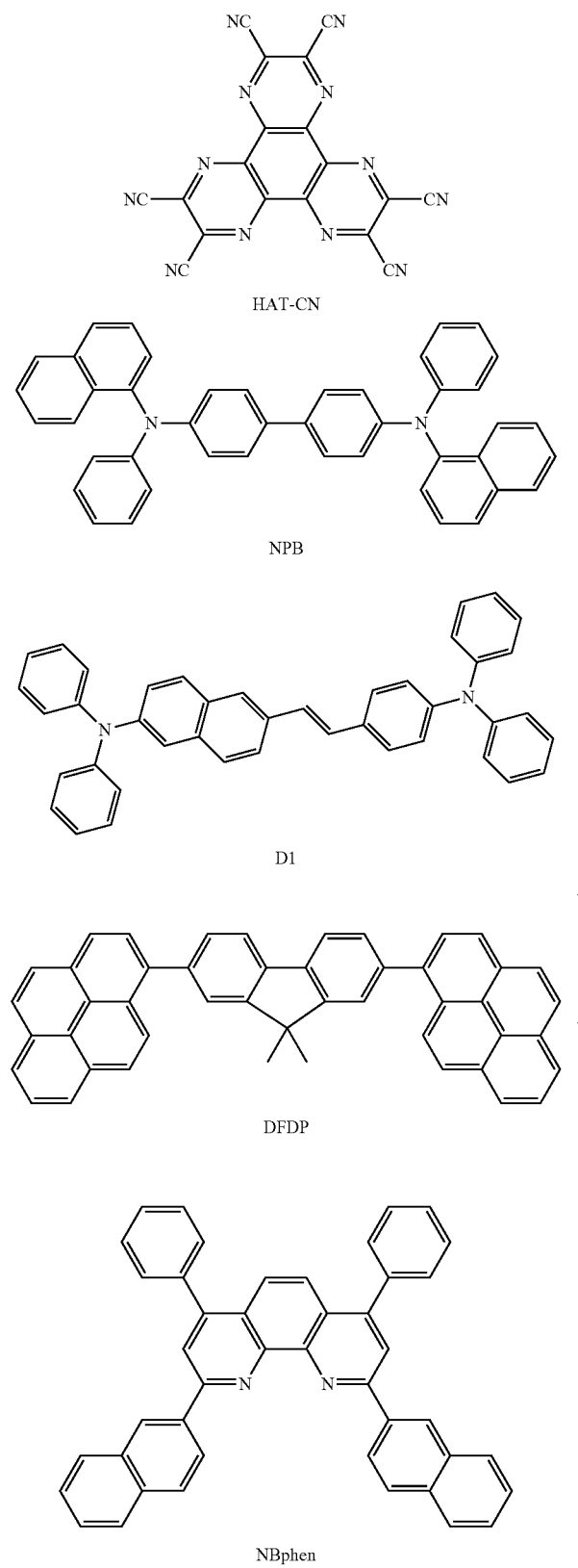

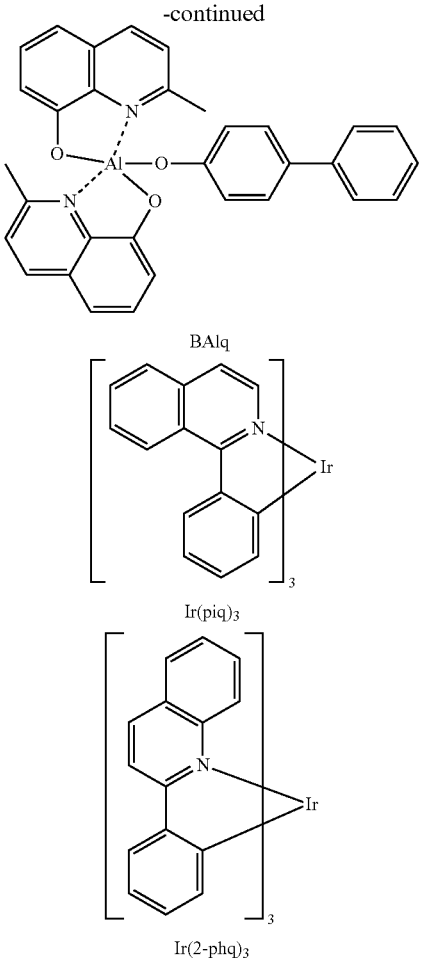

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, MgO, or $Li_2O$.

On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 14

Using a procedure analogous to the above mentioned general method, fluorescent blue-emitting organic EL device having the following device structure were produced (See FIG. 1): ITO/HAT-CN (20 nm)/NPB (60 nm)/fluorescent blue host doped 5% blue dopant (35 nm)/NPhen (30 nm)/LiF (0.5 nm/Al (160 nm). The I-V-B and half-life time of fluorescent blue-emitting Organic EL device testing report as Table 1, The half-life time is defined that the initial luminance of 1000 cd/m² has dropped to half.

TABLE 1

| Fluorescent blue host + 5% dopant | Voltage (V) | Luminance (cd/m²) | Yield (cd/A) | Device color | Half-lifetime (hour) Initial luminance = 1000 (cd/m²) |
|---|---|---|---|---|---|
| II-27 + 5% II-7 | 4.5 | 1000 | 4.8 | Sky Blue | 760 |
| II-29 + 5% II-7 | 4.3 | 1000 | 4.0 | Blue | 660 |
| II-27 + 5% II-8 | 4.8 | 1000 | 5.4 | Sky Blue | 780 |
| II-29 + 5% II-8 | 4.2 | 1000 | 5.1 | Blue | 600 |
| DFDP + 5% II-7 | 6.8 | 1000 | 5.1 | Blue | 320 |
| DFDP + 5% II-8 | 6.5 | 1000 | 5.3 | Blue | 300 |
| II-27 + 5% D1 | 5.0 | 1000 | 4.8 | Sky Blue | 450 |
| II-29 + 5% D1 | 4.8 | 1000 | 5.5 | Blue | 480 |

In the above preferred embodiments, we show that the material formula (II) used as fluorescent blue host or dopant than comparable example DFDP or D1 with higher half-life time and practical operation durability. Under the same Luminance (cd/m²), lower driving voltage than comparable example DFDP and D1 has also been achieved at 1000 cd/m² using the mentioned material formula (II) for blue-emitting organic EL devices. The present invention formula (II) can be used as fluorescent blue host or dopant.

Example 15

Using a procedure analogous to the above mentioned general method, phosphorescent emitting organic EL device having the following device structures are produced (See FIG. 1): ITO/HAT-CN (20 nm)/NPB (50 nm)/phosphorescent host+ 10% dopant (30 nm)/NPhen (30 nm)/LiF (0.5 nm)/Al (160 nm). The I-V-B and half-life time of phosphorescent emitting organic EL device testing report as Table 2. The half-life time is defined that the initial luminance of 3000 cd/m² has dropped to half.

TABLE 2

| Phosphorescent host + 10% dopant | Voltage (V) | Luminance (cd/m²) | Yield (cd/A) | Device color | Half-life time(hour) Initial luminance = 3000 (cd/m²) |
|---|---|---|---|---|---|
| BAlq + 10% Ir(piq)₃ | 6 | 750 | 7.6 | red | 300 |
| BAlq + 10% Ir(phq)₃ | 6 | 450 | 13.2 | orange | 320 |
| III-8 + 10% Ir(piq)₃ | 6 | 910 | 6.9 | red | 610 |
| III-8 + 10% Ir(phq)₃ | 6 | 920 | 13.7 | yellow | 730 |
| III-29 + 10% Ir(piq)₃ | 6 | 980 | 8.8 | red | 580 |
| III-29 + 10% Ir(phq)₃ | 6 | 850 | 16.8 | yellow | 870 |
| III-30 + 10% Ir(piq)₃ | 6 | 1100 | 8.6 | red | 600 |
| III-30 + 10% Ir(phq)₃ | 6 | 660 | 15.6 | orange | 750 |
| III-31 + 10% Ir(piq)₃ | 6 | 760 | 7.7 | red | 580 |
| III-31 + 10% Ir(phq)₃ | 6 | 600 | 11.5 | yellow | 650 |
| III-33 + 10% Ir(piq)₃ | 6 | 870 | 7.1 | red | 550 |
| III-33 + 10% Ir(phq)₃ | 6 | 910 | 10.5 | yellow | 630 |

In the above preferred embodiments, we show the ditriphenylene derivative formula (III) used as phosphorescent host than comparable example BAlq with higher half-life time and practical operation durability. Higher luminance and efficiency than comparable BAlq has also been achieved at a driving voltage of 6V using the mentioned ditriphenylene derivative formula (III) for phosphorescent organic EL devices. The ditriphenylene derivative formula (III) can be used as phosphorescent organic EL devices for practice use.

To sum up, the present invention discloses a ditriphenylene derivative which can be used for organic EL device is disclosed. The mentioned ditriphenylene derivative are represented by the following formula (I):

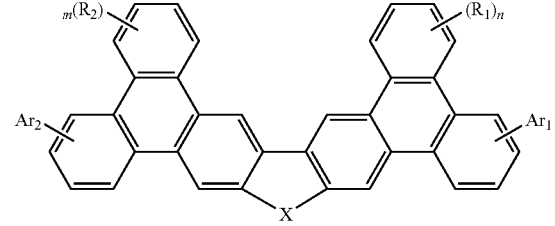

formula(I)

Wherein m, n represent an integer of 0 to 10. X is a divalent bridge selected from the atom or group consisting from O, S, $C(R_3)(R_4)$, $NR_5$, $Si(R_6)(R_7)$. $Ar_1$, $Ar_2$ are the same or different. $Ar_1$, $Ar_2$ represent a hydrogen atom, a halide, a substituted or unsubstituted arylamine group, a substituted or unsubstituted aryl group system having 5 to 60 aromatic ring atoms and each aromatic ring to form a mono or polycyclic ring system, a substituted or unsubstituted heteroaryl group system having 5 to 60 aromatic ring atoms and each aromatic ring to form a mono or polycyclic ring system. $R_1$ to $R_7$ are identical or different. $R_1$ to $R_7$ are independently selected from the group consisting of a hydrogen atom, alkyl group having 1 to 20 carbon atoms, a substituted or unsubstituted aryl group having 6 to 50 carbon atoms, a substituted or unsubstituted aralkyl group having 6 to 50 carbon atoms, a substituted or unsubstituted heteroaryl group having 6 to 50 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A ditriphenylene derivative with a general formula (I) as following:

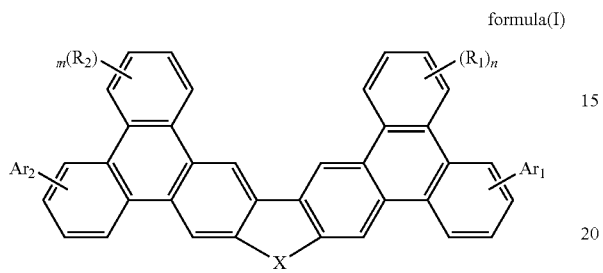

formula(I)

wherein m and n represent an integer of 0 to 10, X is a divalent bridge selected from the atom of group consisting of O, S, $C(R_3)(R_4)$, $NR_5$, and $Si(R_6)(R_7)$; $Ar_1$ and $Ar_2$ are the same or different, $Ar_1$ and $Ar_2$ represent a hydrogen atom, a halide, a substituted or unsubstituted arylamine group, a substituted or unsubstituted aryl group system having 5 to 60 aromatic ring atoms and each aromatic ring forms a mono or polycyclic ring system, or a substituted or unsubstituted heteroaryl group system having 5 to 60 aromatic ring atoms and each aromatic ring forms a mono or polycyclic ring system, $R_1$ to $R_7$ are identical or different, $R_1$ to $R_7$ are independently selected from the group consisting of a hydrogen atom, alkyl group having 1 to 20 carbon atoms, a substituted or unsubstituted aryl group having 6 to 50 carbon atoms, a substituted or unsubstituted aralkyl group having 6 to 50 carbon atoms, and a substituted or unsubstituted heteroaryl group having 6 to 50 carbon atoms.

2. The derivative according to claim 1, wherein the ditriphenylene derivative formula (I) is used as fluorescent host material or dopant material of an emitting layer for an organic EL device is represented by the following formula (II):

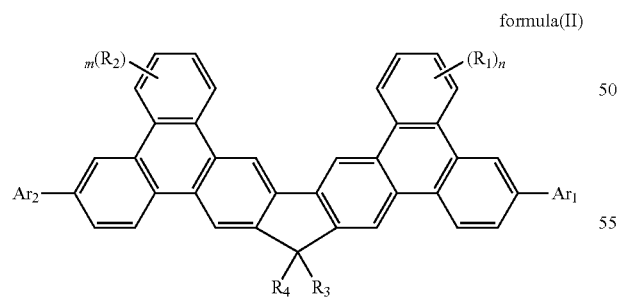

formula(II)

wherein m and n represent an integer of 0 to 10, $Ar_1$ and $Ar_2$ are the same or different, $Ar_1$ and $Ar_2$ represent a hydrogen atom, a halide, a substituted or unsubstituted arylamine group, a substituted or unsubstituted aryl group system having 5 to 60 aromatic ring atoms and each aromatic ring forms a mono or polycyclic ring system, or a substituted or unsubstituted heteroaryl group system having 5 to 60 aromatic ring atoms and each aromatic ring forms a mono or polycyclic ring system, $R_1$ to $R_4$ are identical or different, $R_1$ to $R_4$ are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 6 to 30 carbon atoms.

3. The derivative according to claim 2, wherein $Ar_1$ and $Ar_2$ are represented by the following formulas:

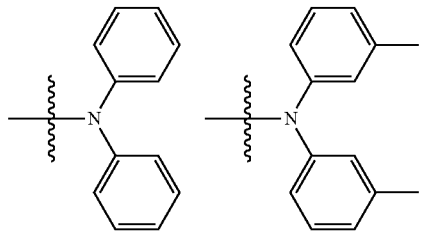

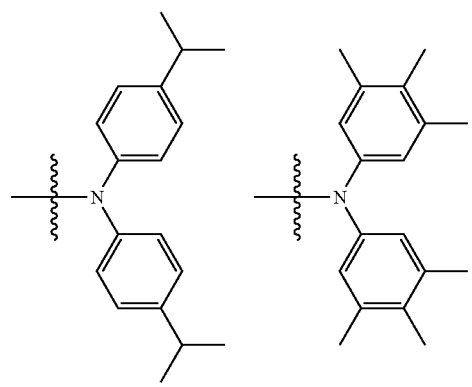

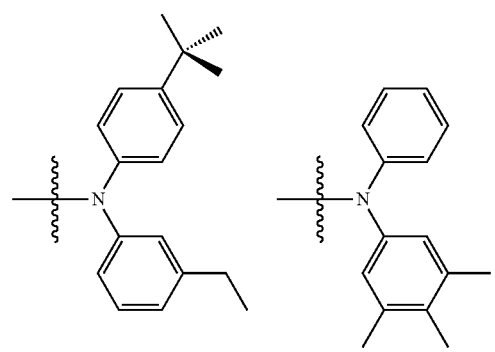

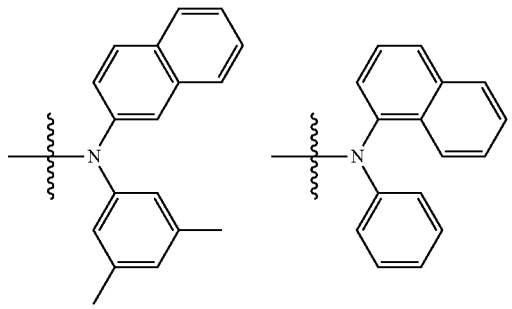

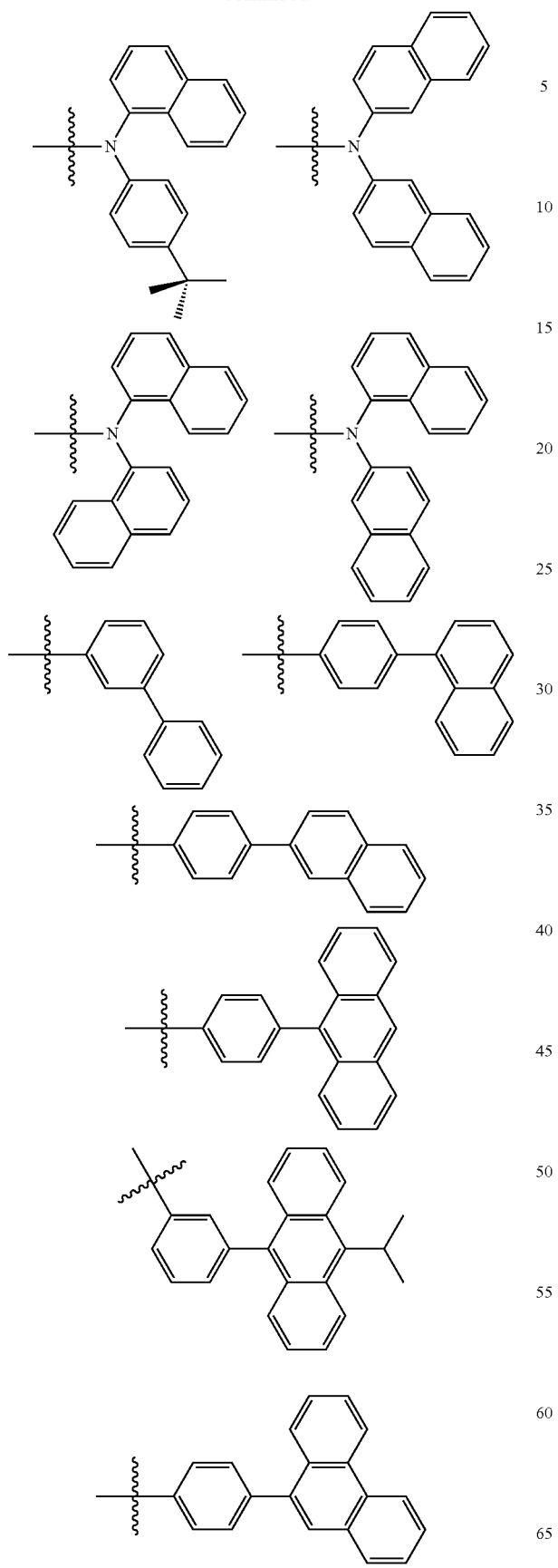
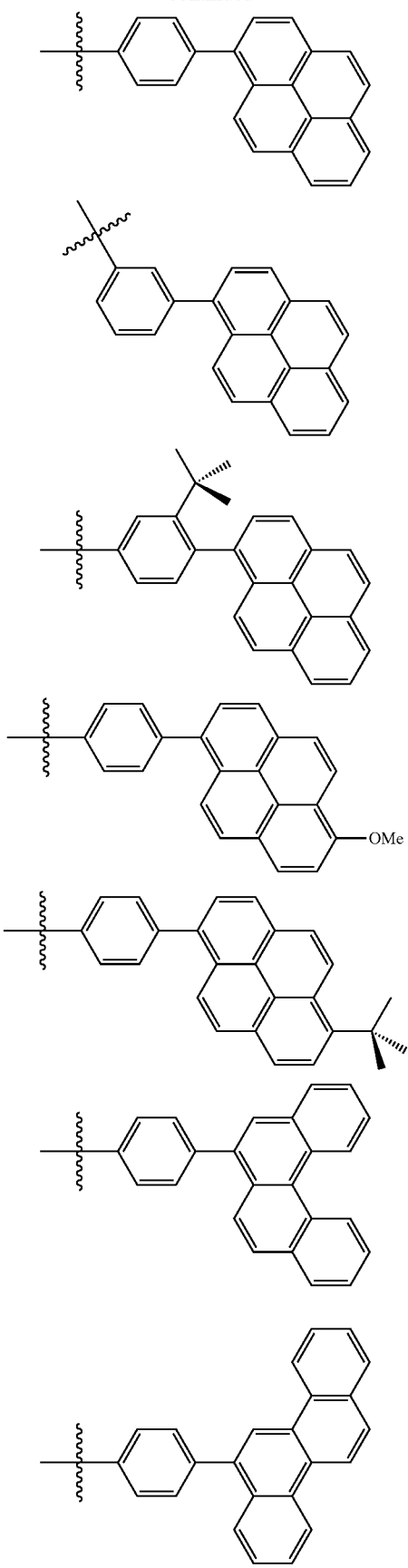

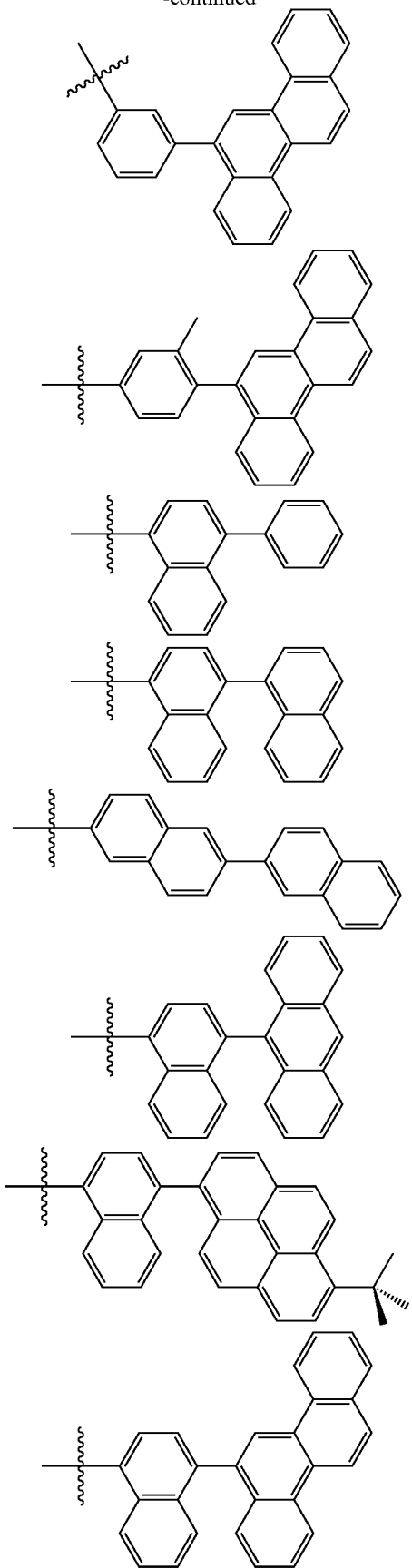
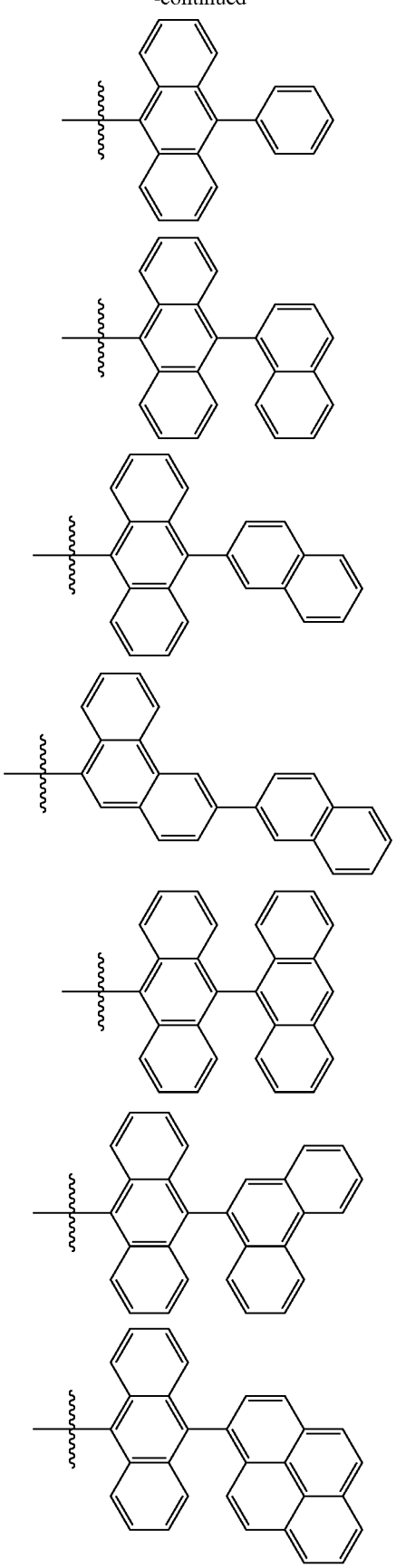

99
-continued
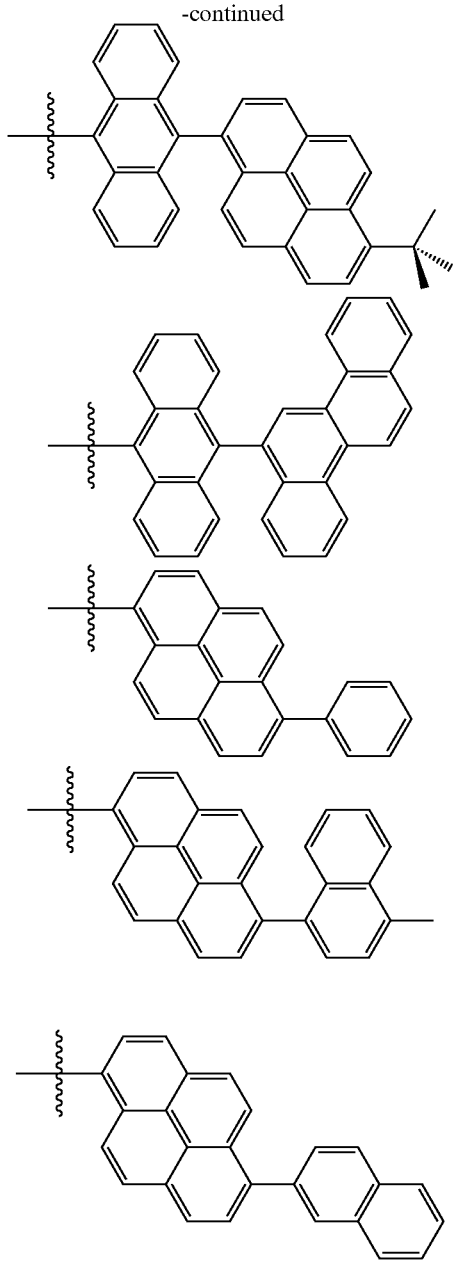
100
-continued
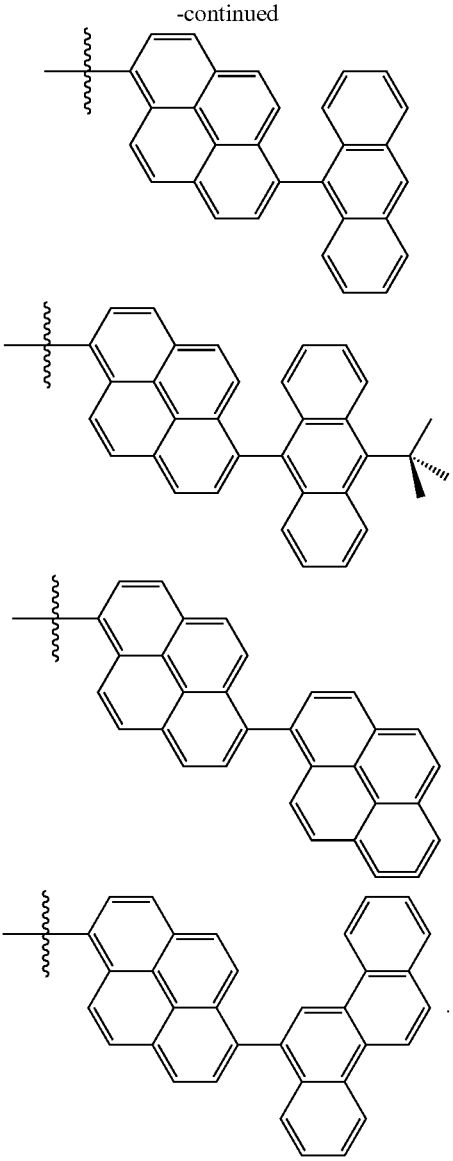
4. The derivative according to claim 2, wherein the ditriphenylene derivative is selected from compounds represented by the following structures:
II-1
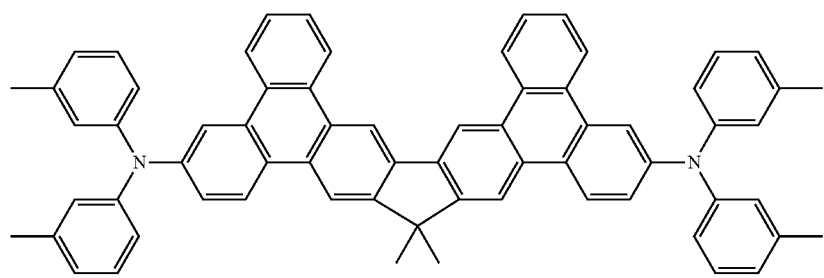

II-2
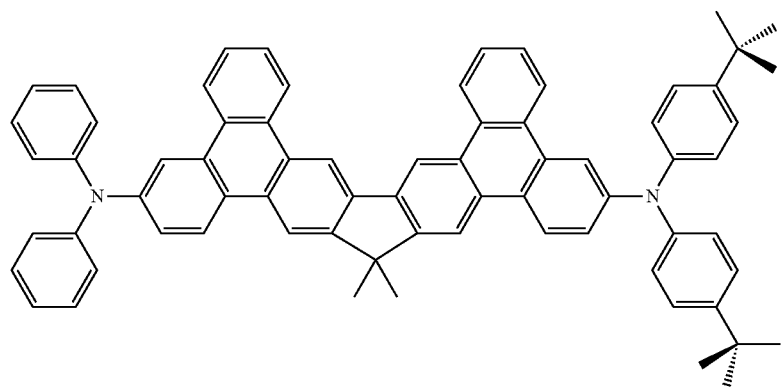
II-3
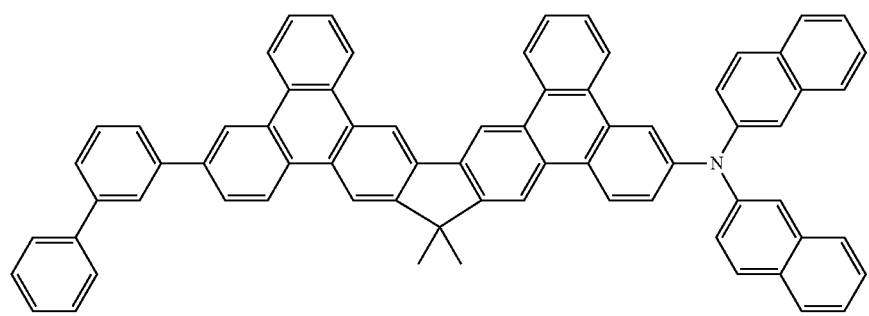
II-4
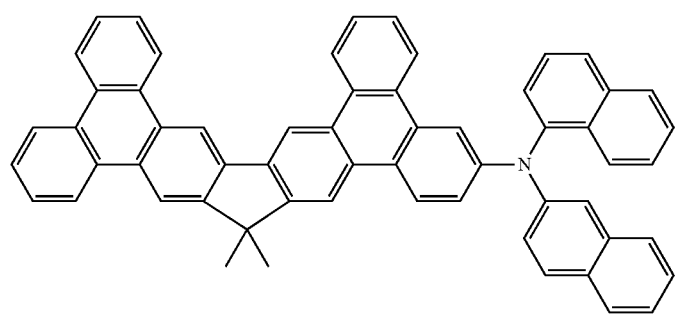
II-6
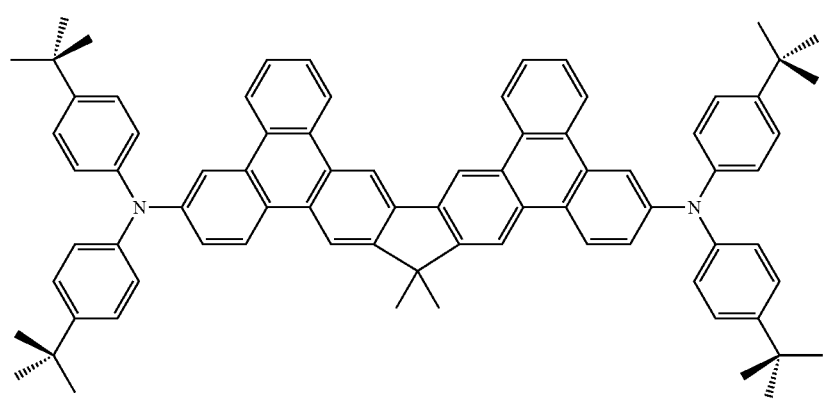

II-7
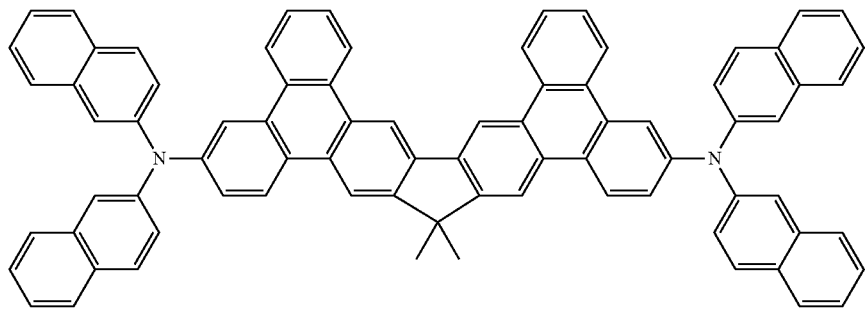
II-8
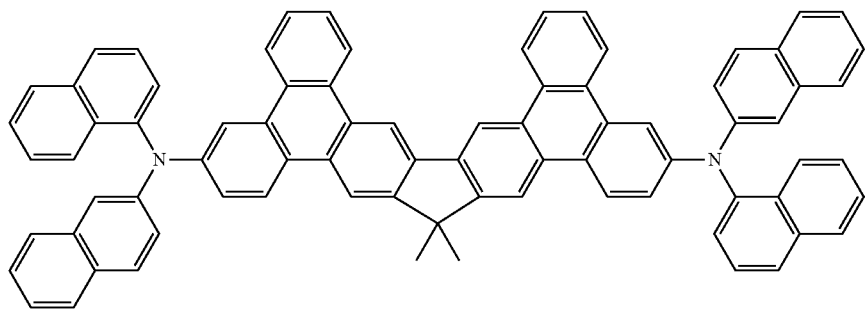
II-9
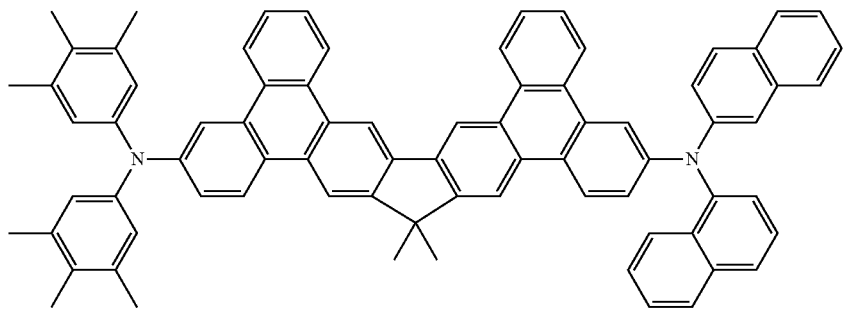
II-10
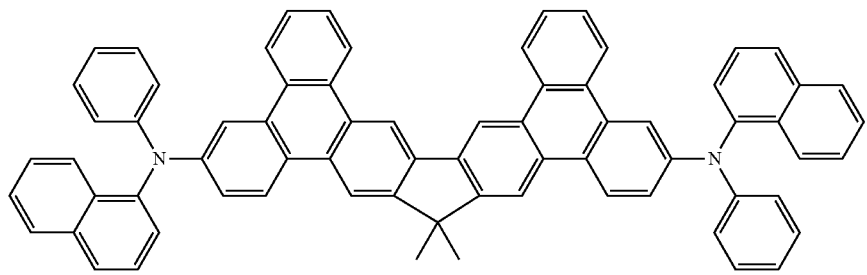
II-11
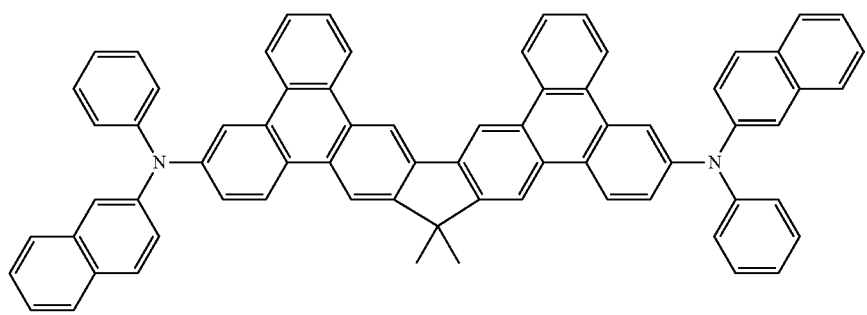

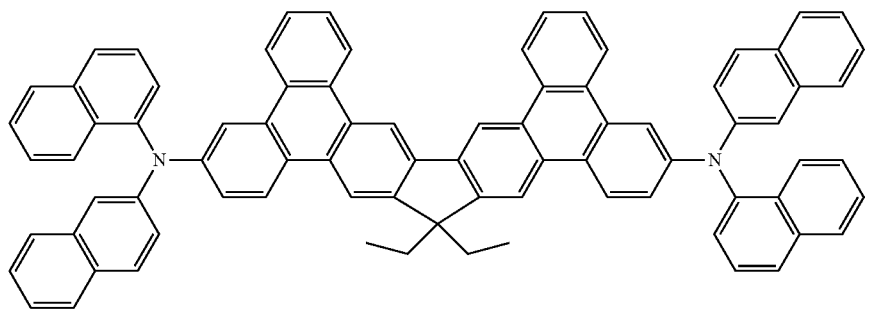
II-12
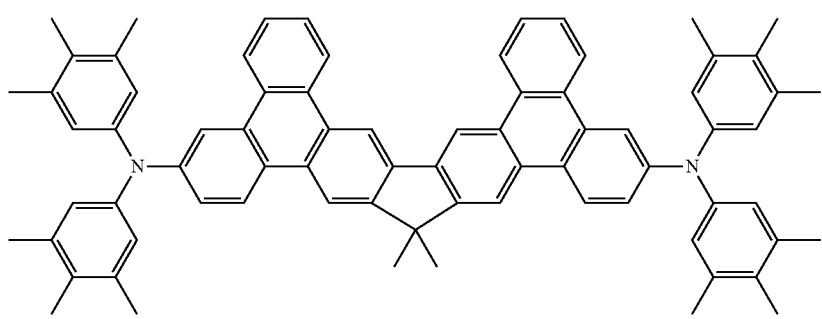
II-13
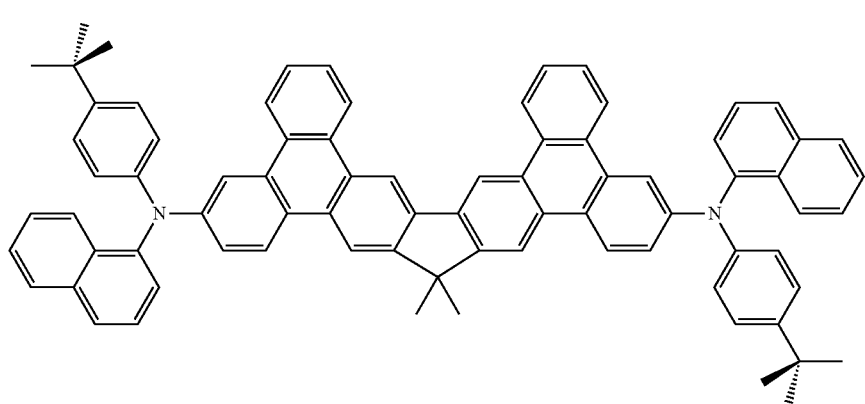
II-14
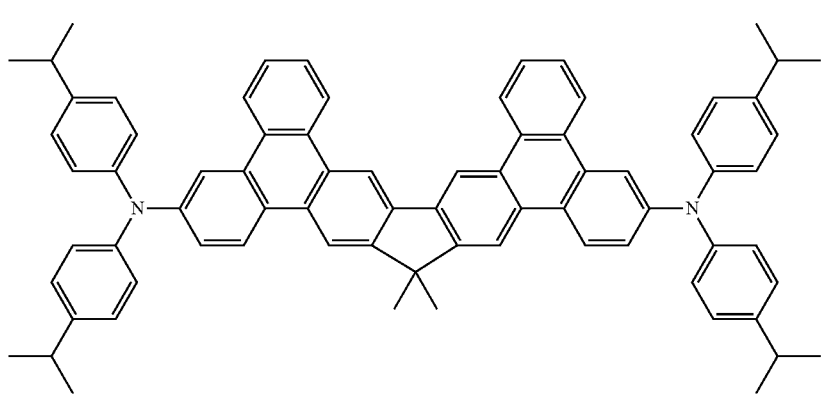
II-15

-continued
II-16
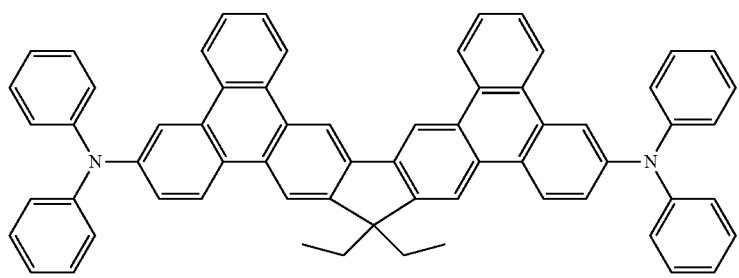
II-17
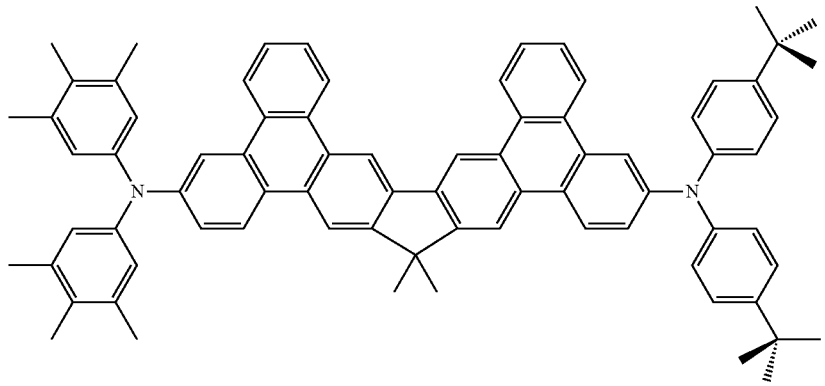
II-18
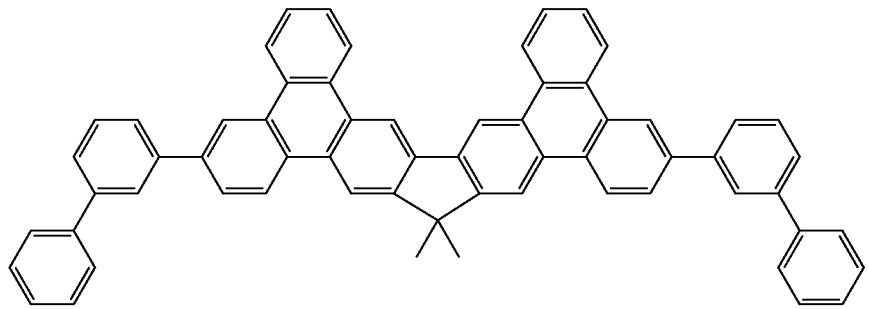
II-19
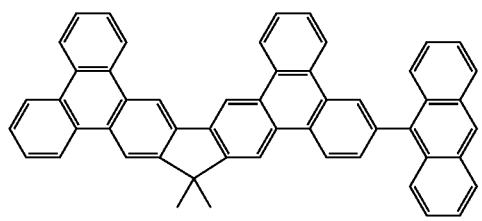
II-20
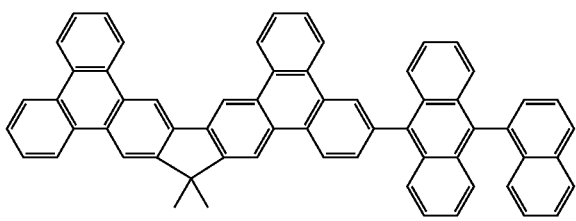
II-21
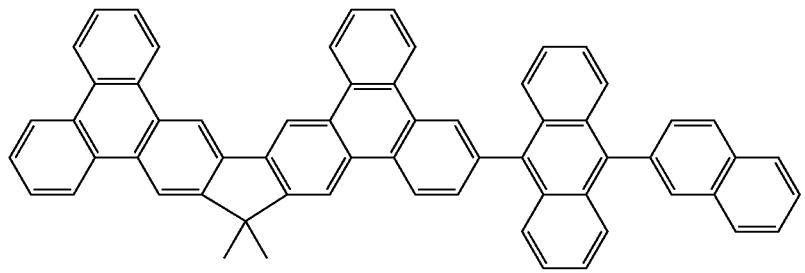

II-22
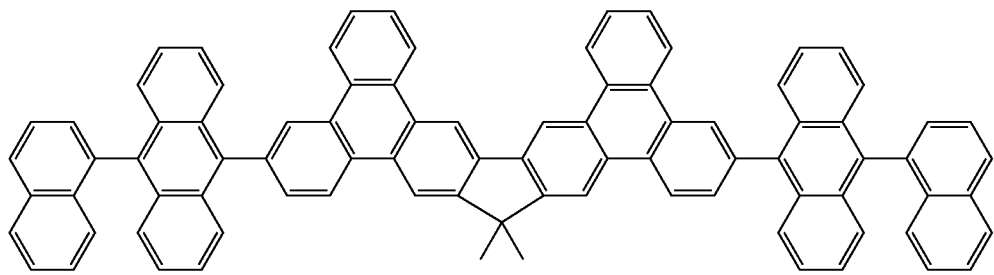
II-23
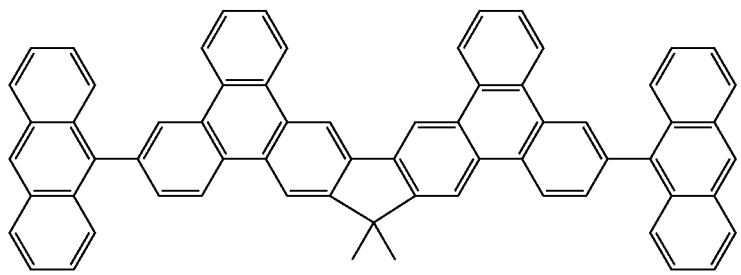
II-24
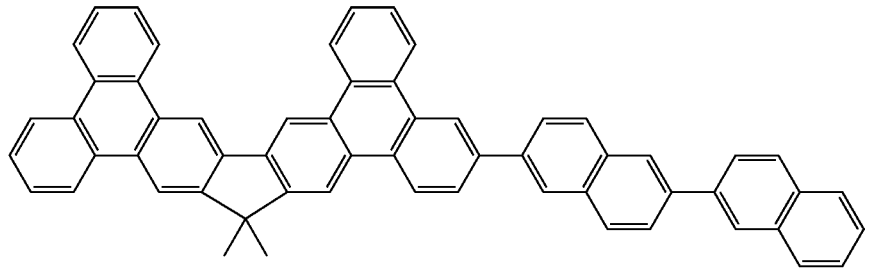
II-25    II-26
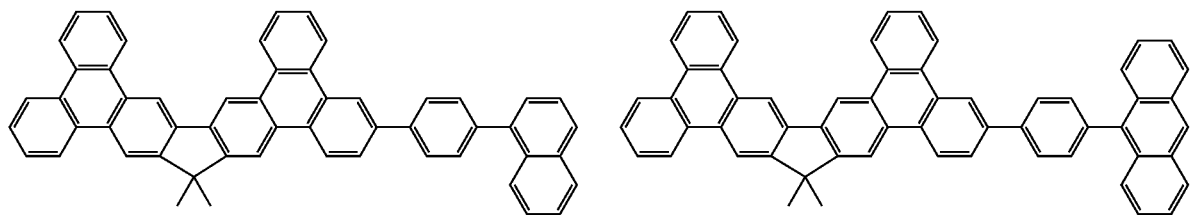
II-27
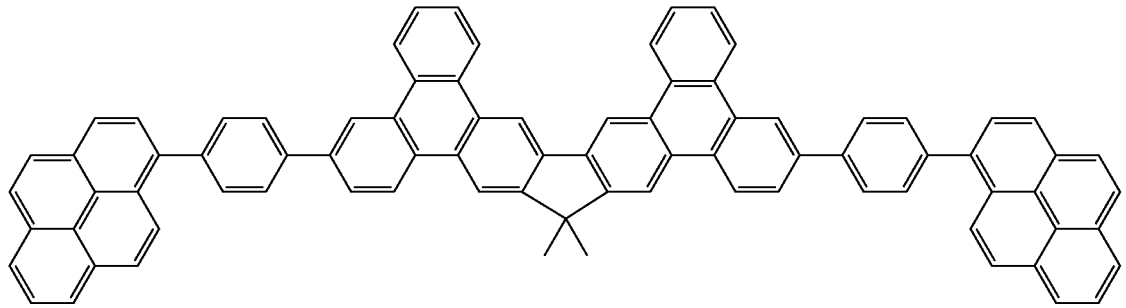

II-28
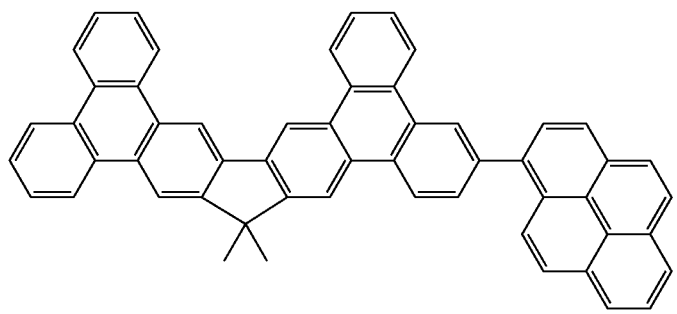
II-29
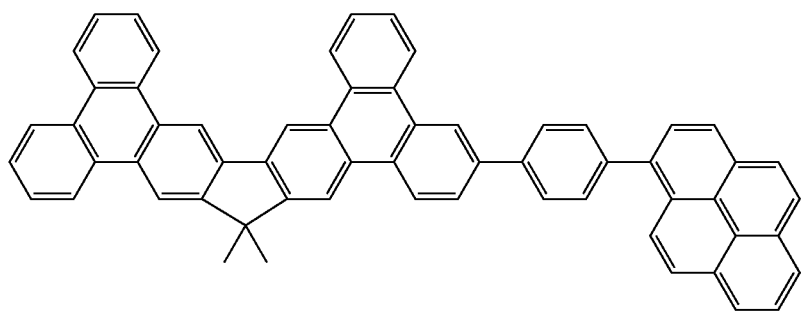
II-30
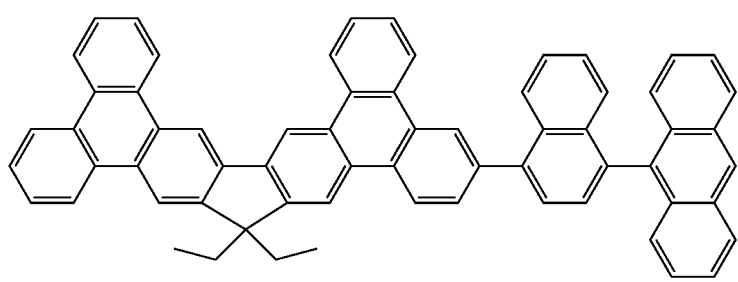
II-31
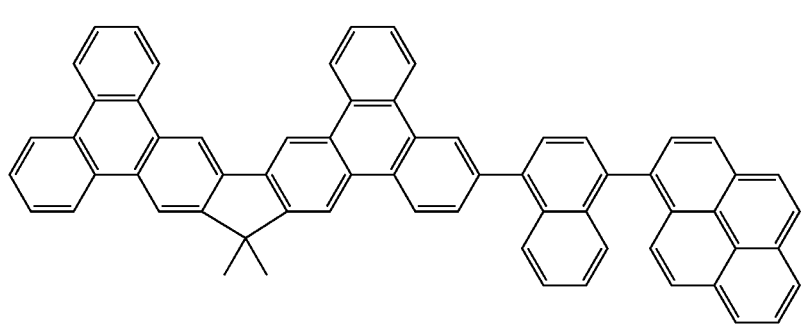
II-32
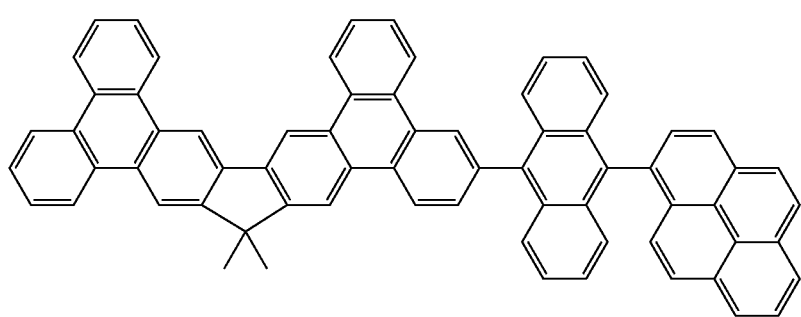

-continued
II-33
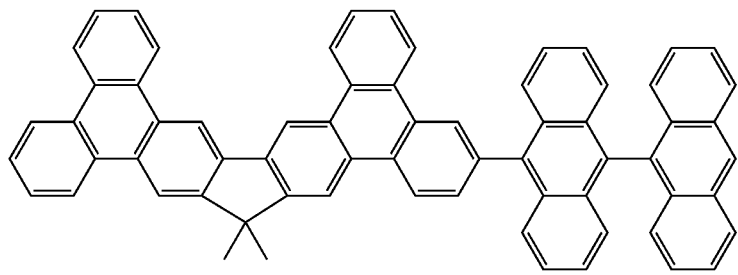
II-34
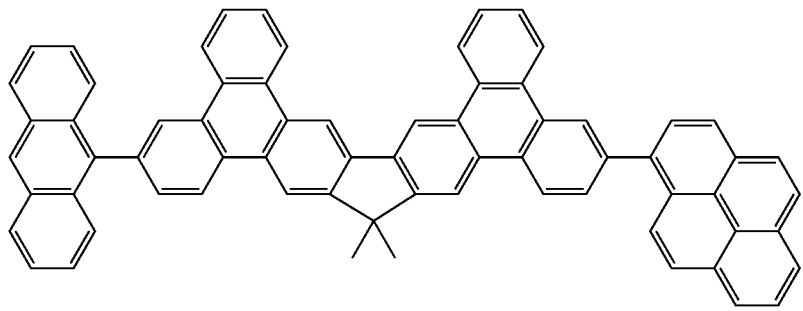
II-35
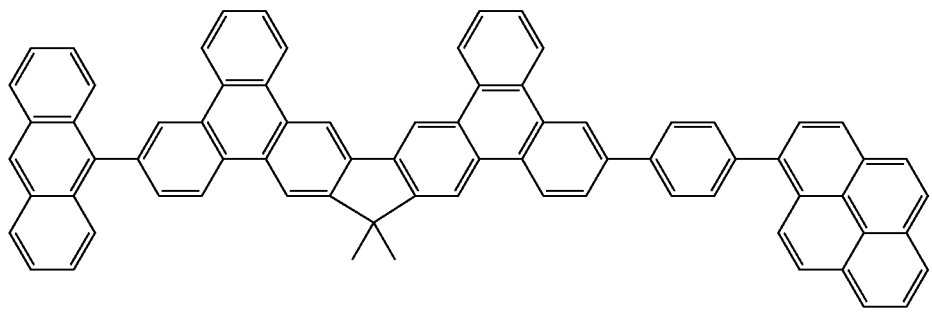
II-36
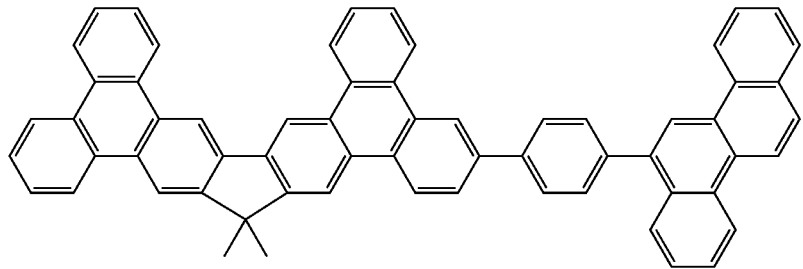
II-37
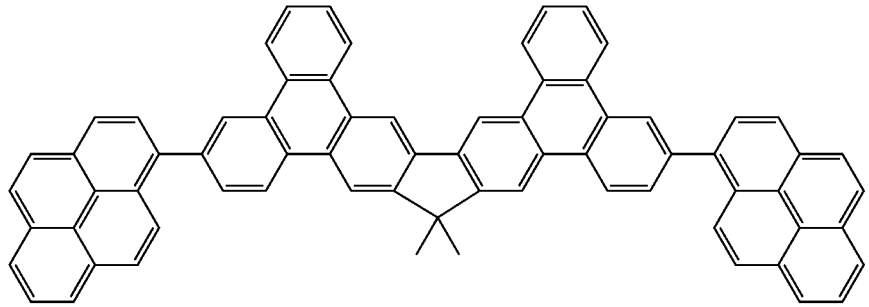

II-38

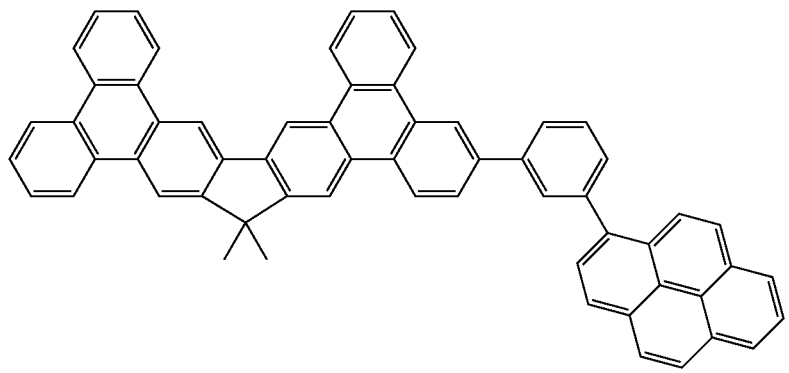

II-39

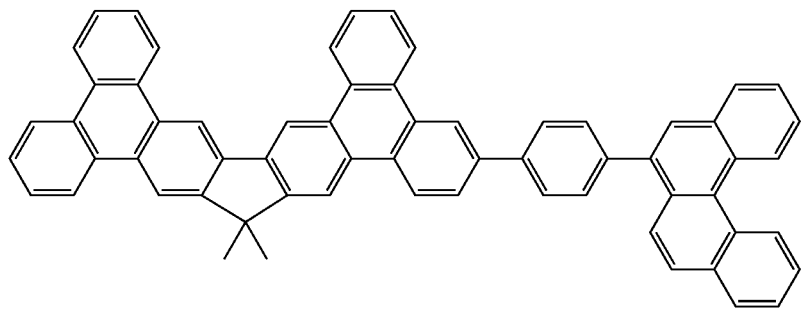

II-40

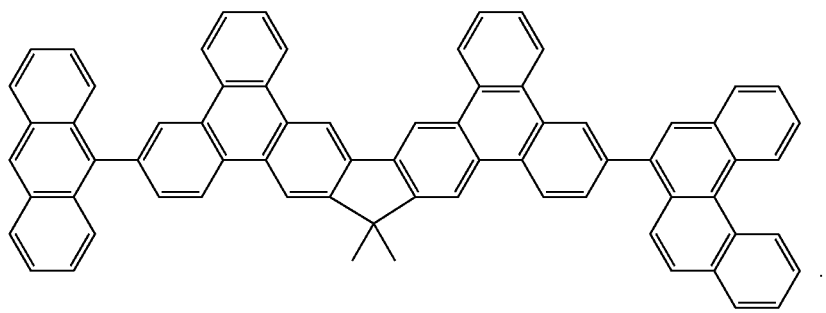

5. The derivative according to claim 1, wherein the ditriphenylene derivative formula (I) is used as phosphorescent host material of an emitting layer for an organic EL device is represented by the following formula (III):

formula(III)

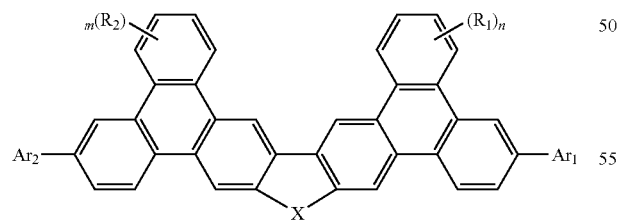

wherein m and n represent an integer of 0 to 10, X is a divalent bridge selected from the atom of group consisting of O, S, $NR_5$; $Ar_1$, $Ar_2$, and $R_5$ are the same or different; $Ar_1$, $Ar_2$, and $R_5$ represent a hydrogen atom, a halide, a substituted or unsubstituted arylamine group, a substituted or unsubstituted aryl group system having 5 to 60 aromatic ring atoms and each aromatic ring forms a mono or polycyclic ring system, or a substituted or unsubstituted heteroaryl group system having 5 to 60 aromatic ring atoms and each aromatic ring forms a mono or polycyclic ring system; $R_1$, $R_2$ are identical or different; $R_1$, $R_2$ are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 6 to 30 carbon atoms.

6. The derivative according to claim 5, wherein $Ar_1$, $Ar_2$, and $R_5$ are heteroaryl group or aryl group and are represented by the following:

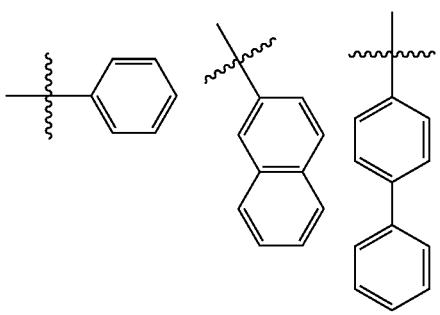

117
-continued
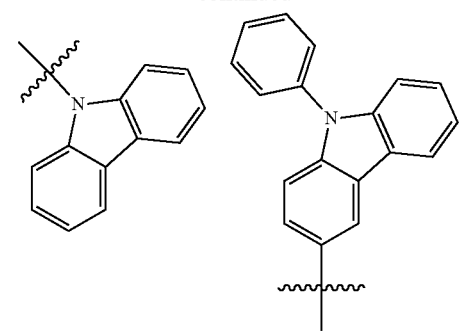
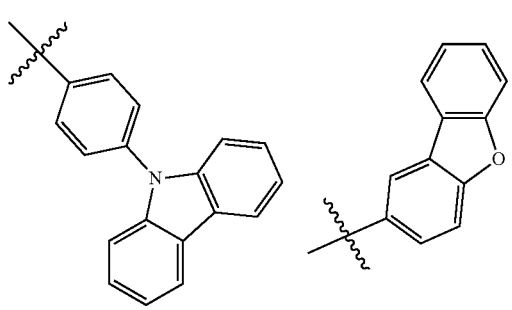
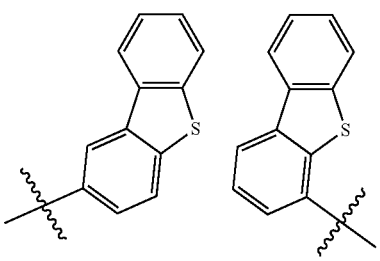
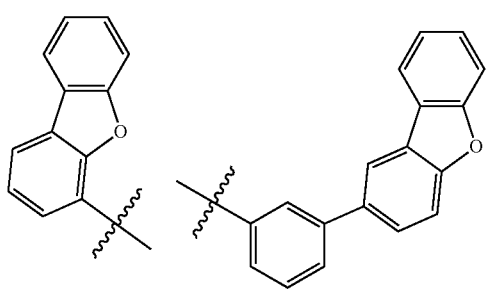
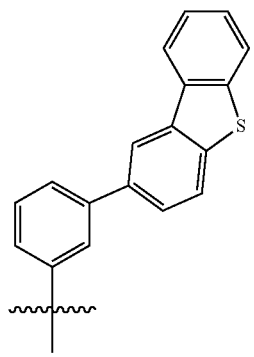
118
-continued
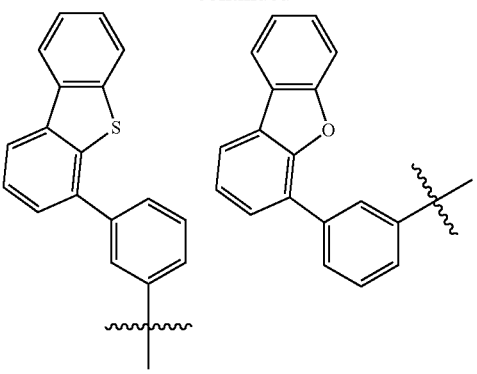
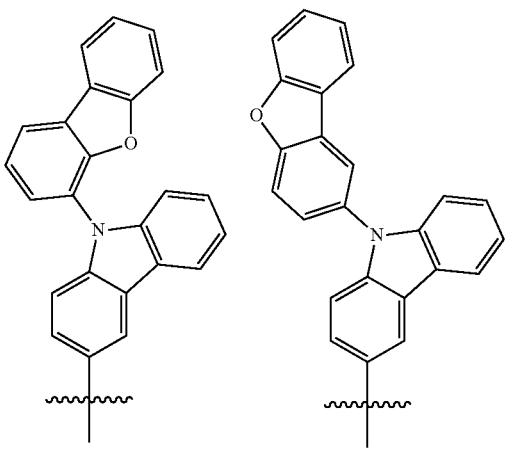
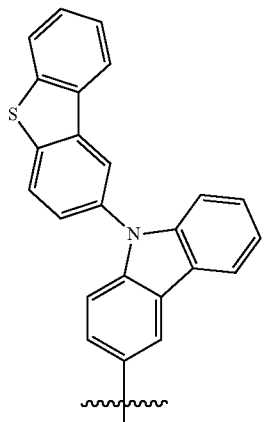
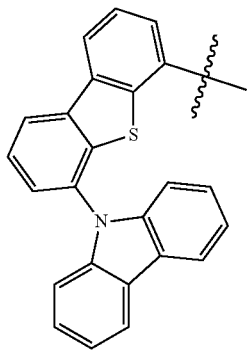
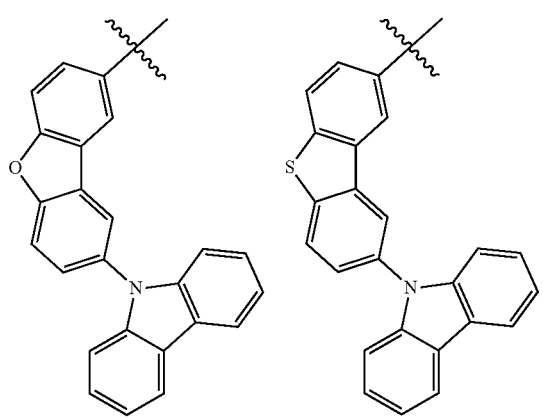

119
-continued
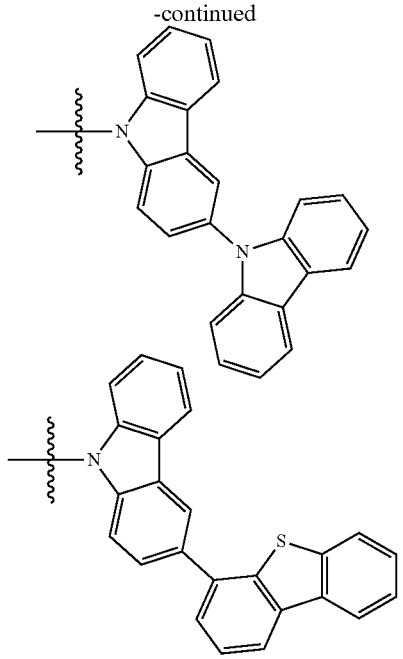
120
-continued
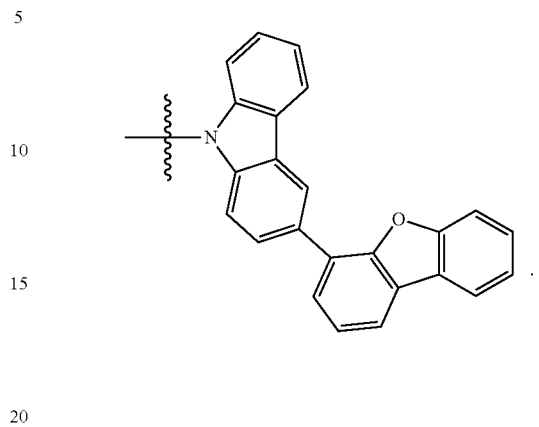
7. The derivative according to claim 5, wherein the ditriphenylene derivative is selected from compounds represented by the following structures:
III-1
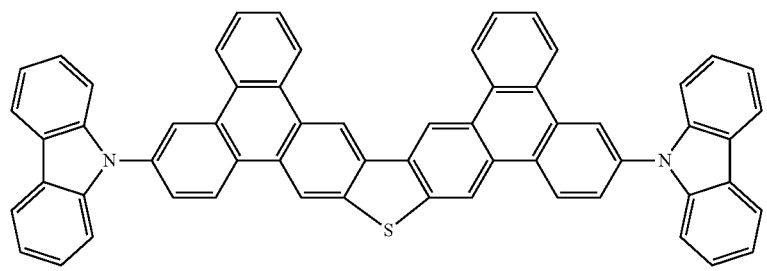
III-2
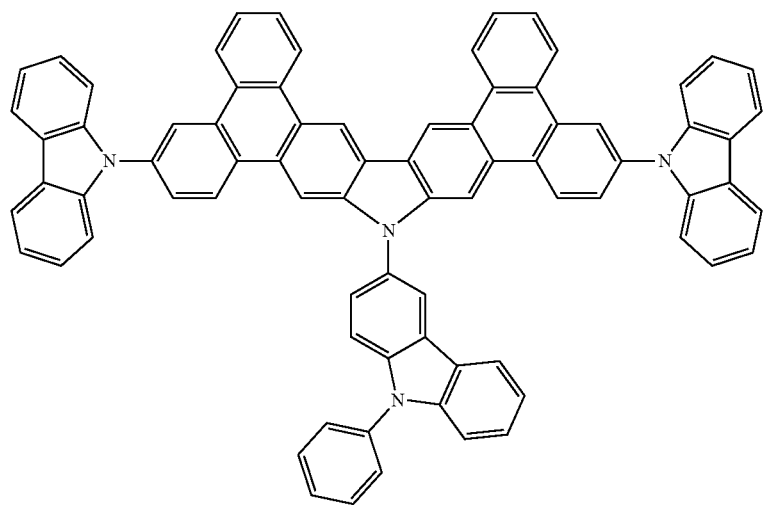

121 122
-continued
III-3
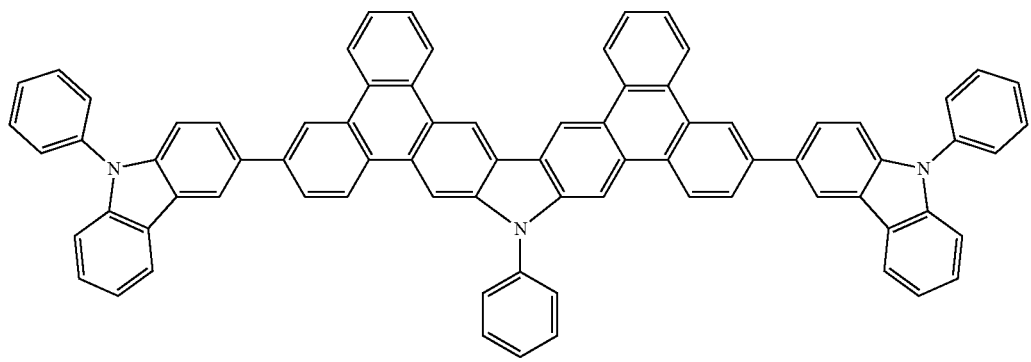
III-4
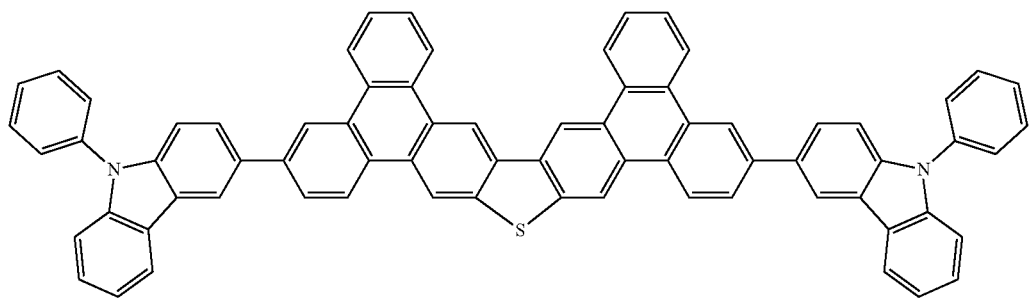
III-5
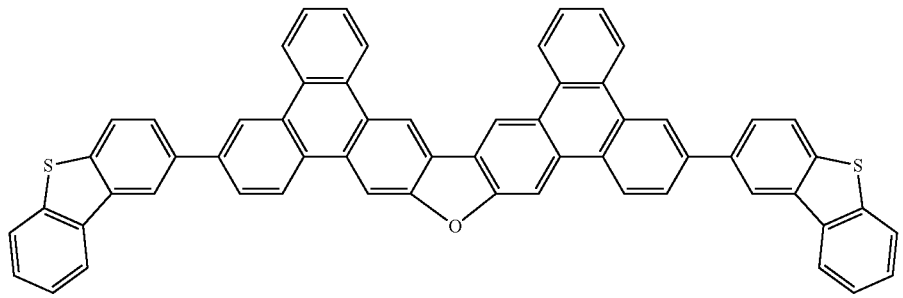
III-6
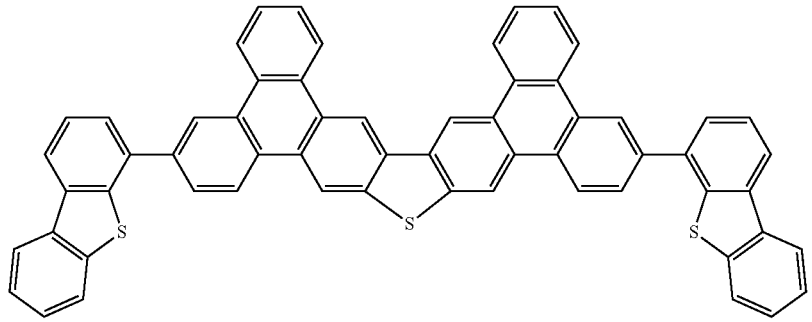
III-7
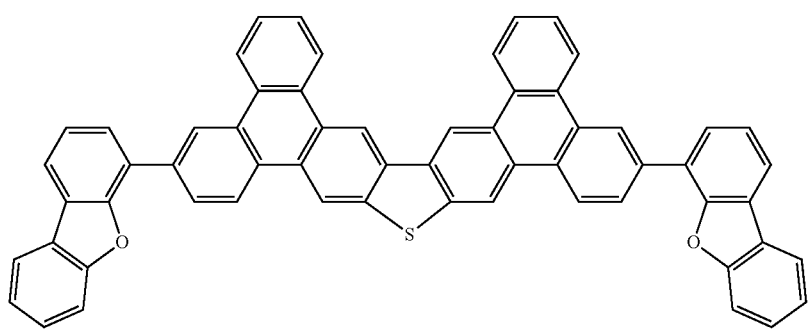

III-8
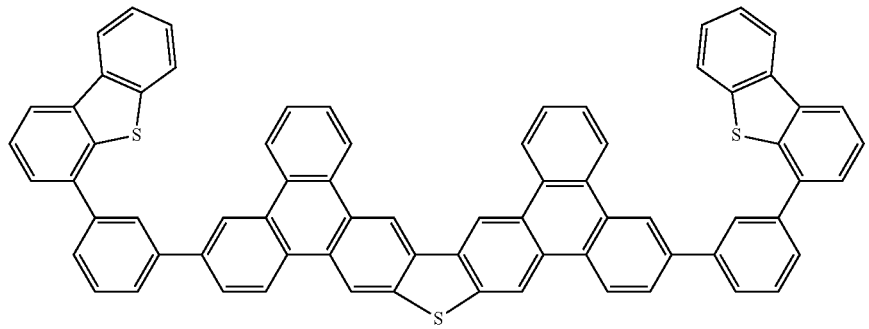
III-9
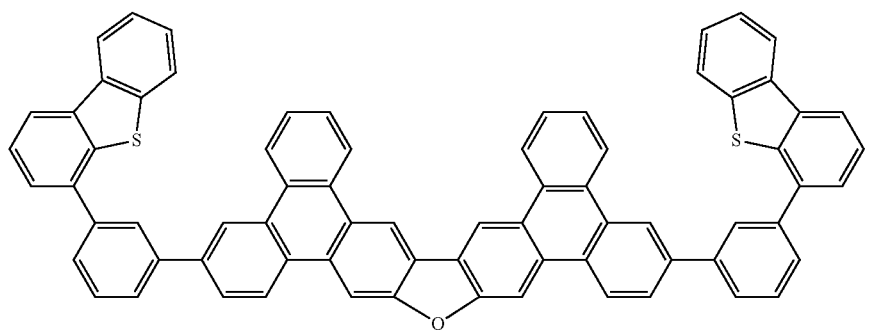
III-10
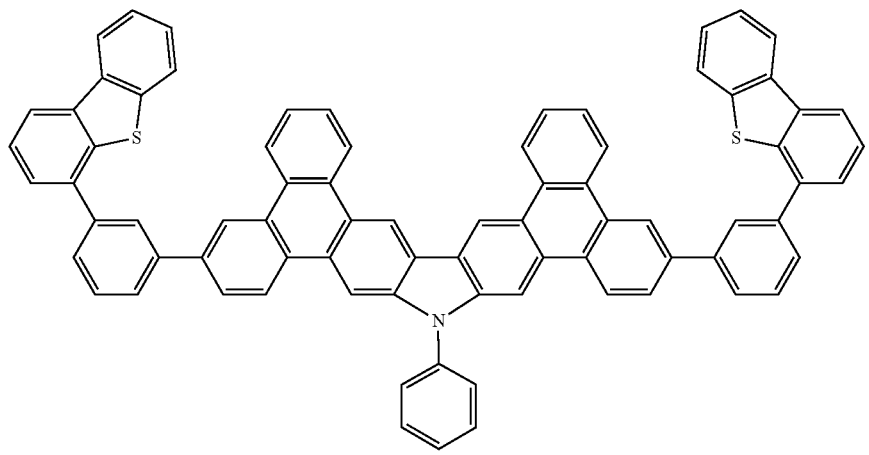
III-11
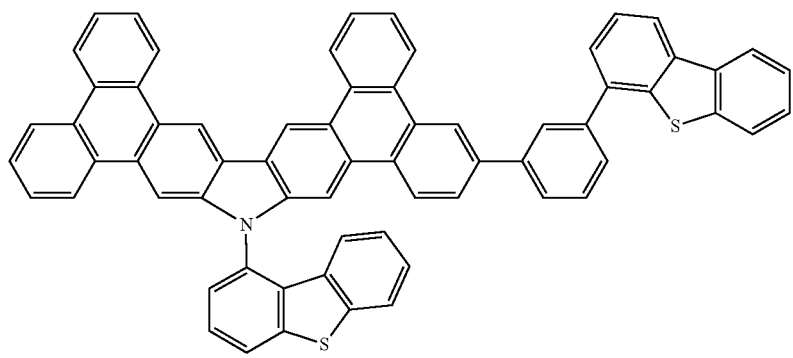

-continued
III-12
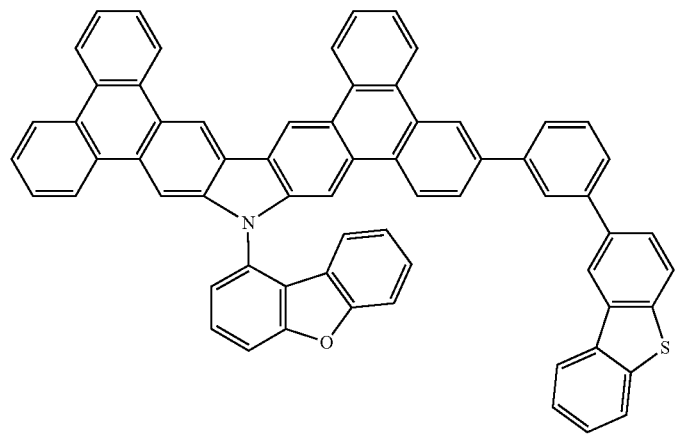
III-13
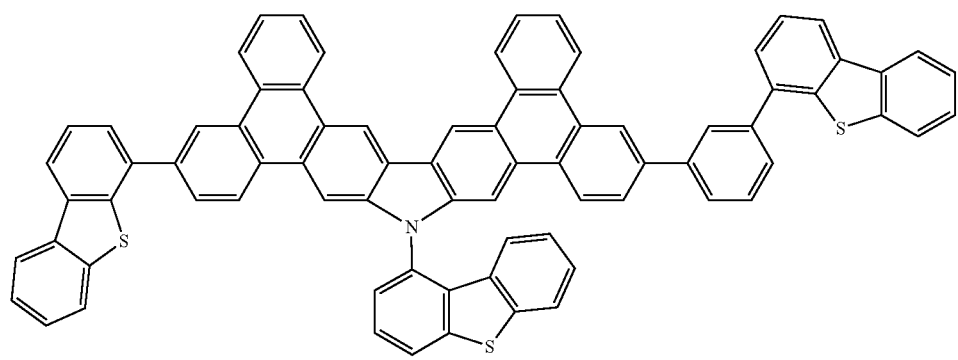
III-14
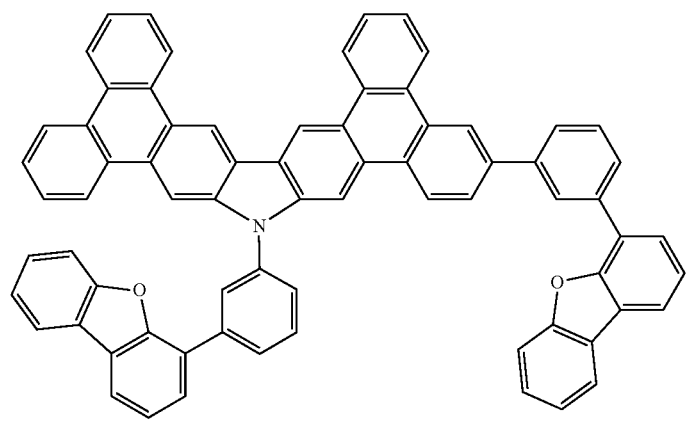
III-15
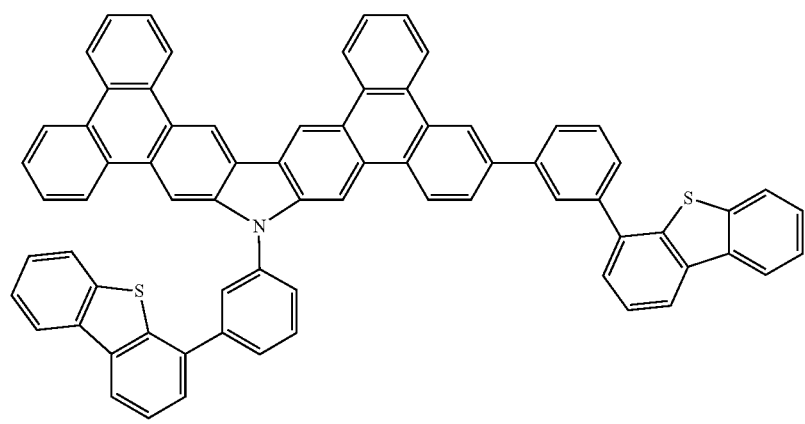

III-16
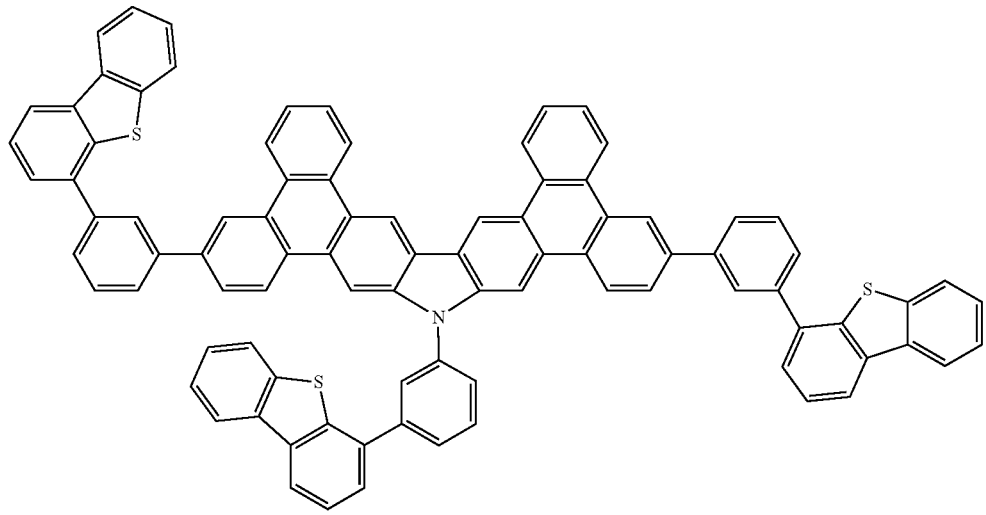
III-17
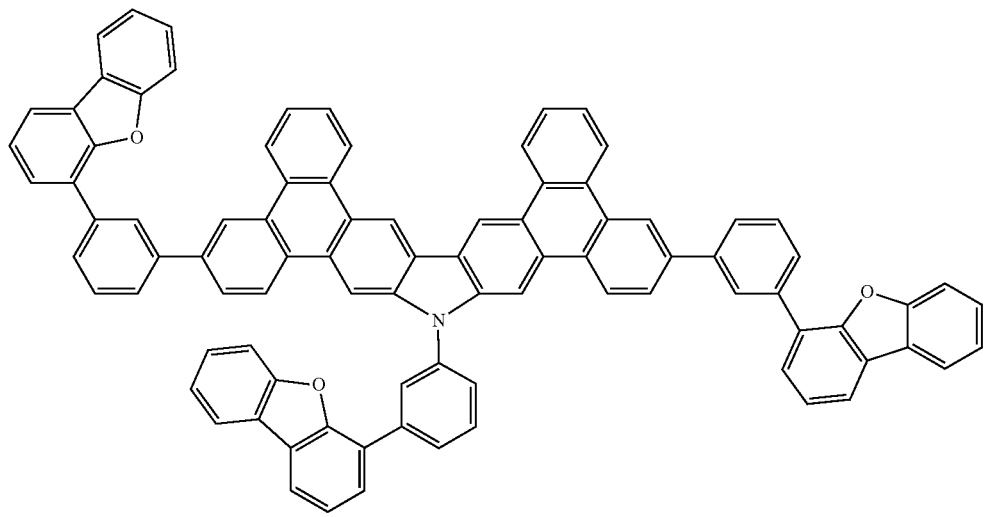
III-18
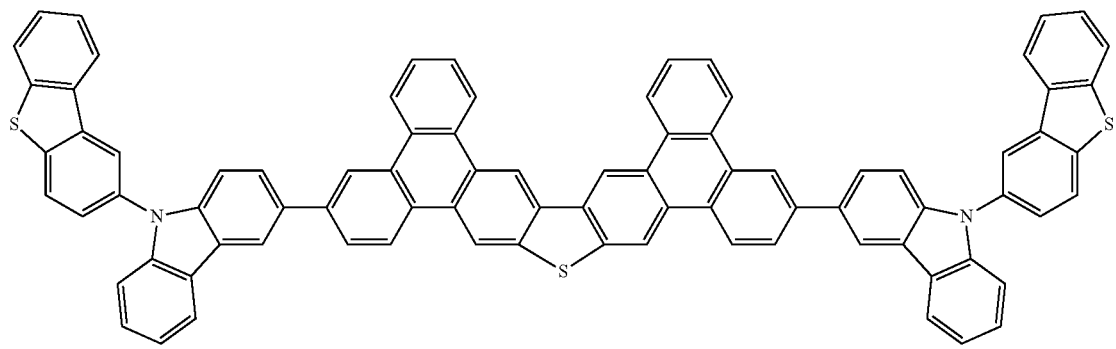

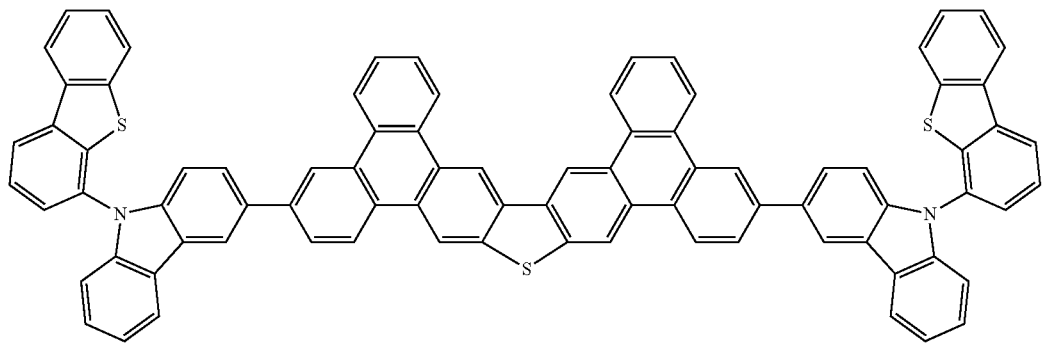
III-19
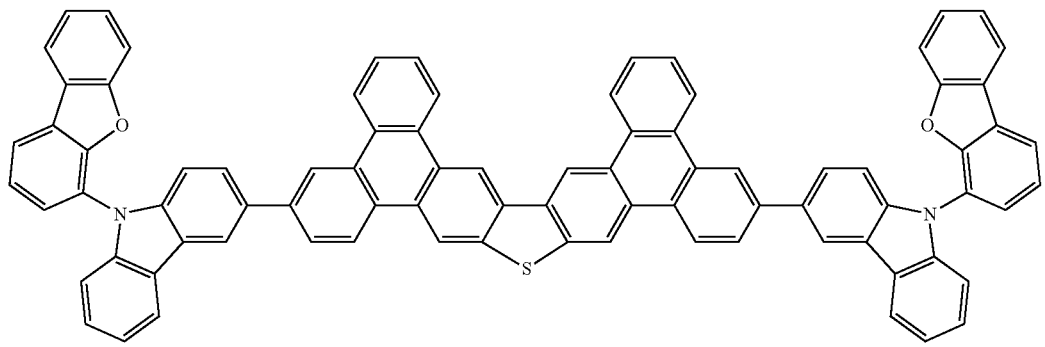
III-20
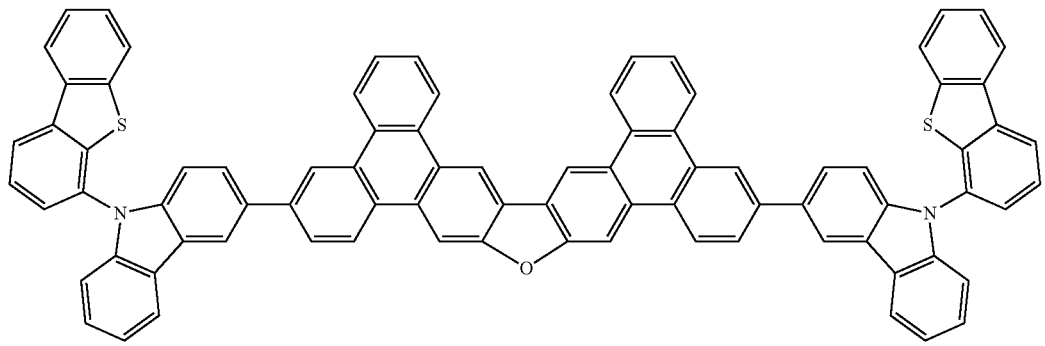
III-21
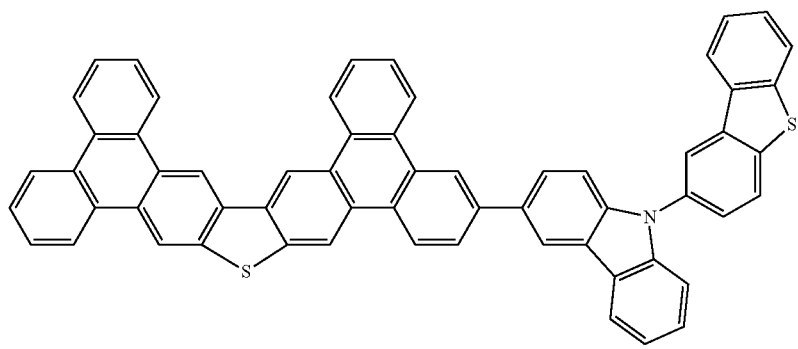
III-22

-continued
III-23
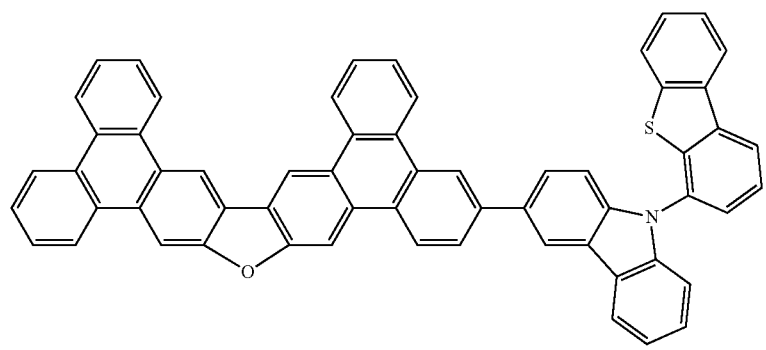
III-24
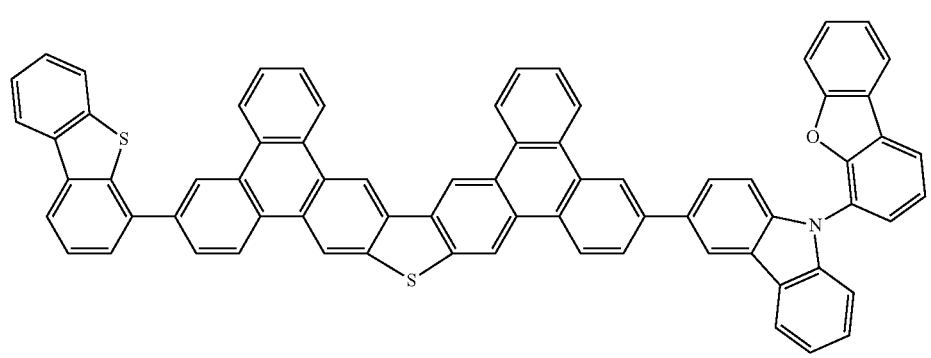
III-25
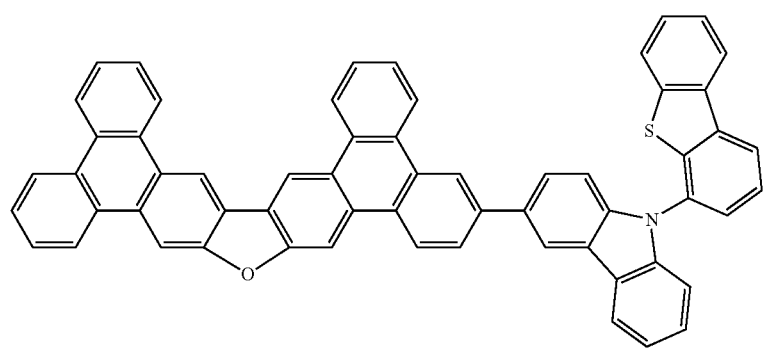
III-26
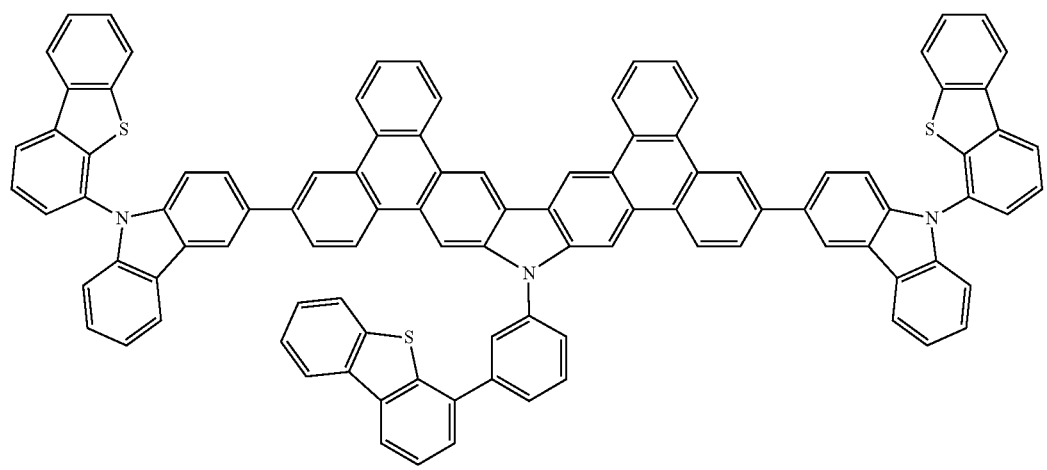

III-27
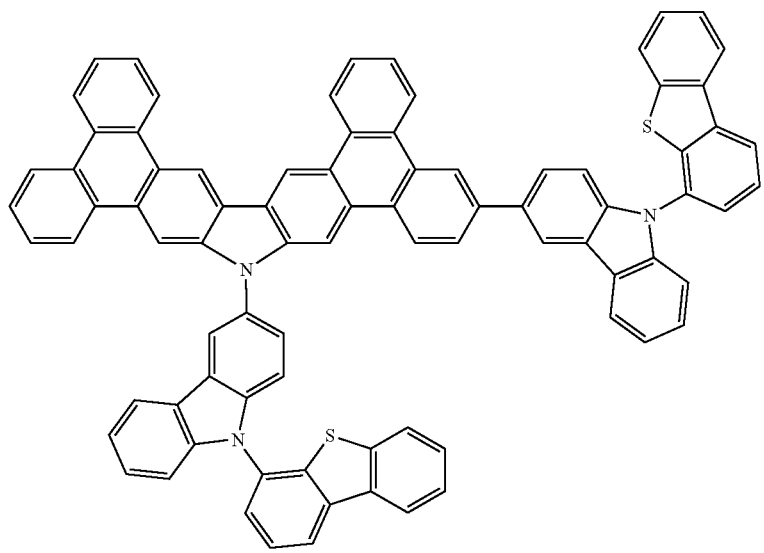
III-28
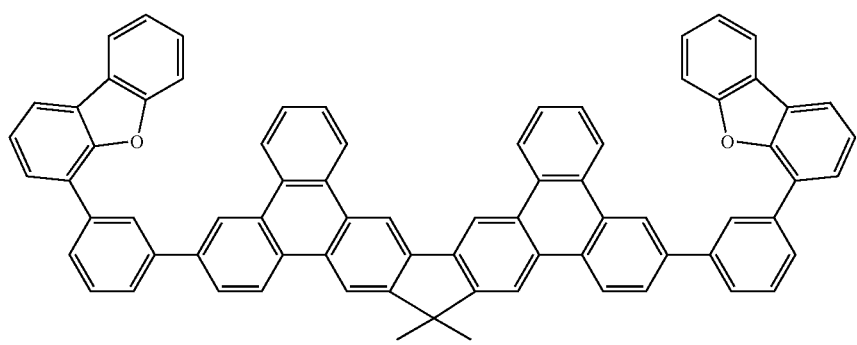
III-29
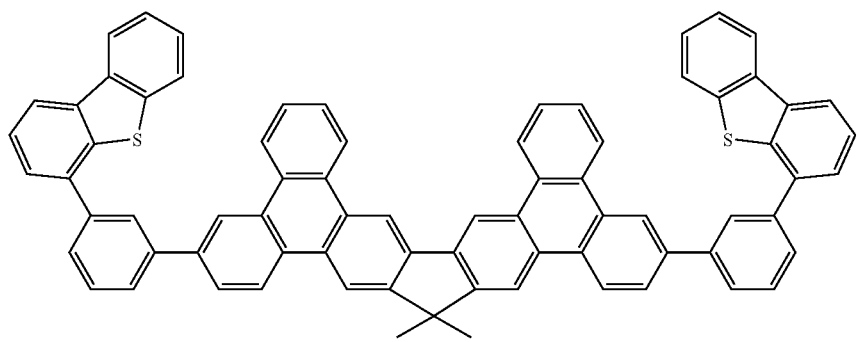
III-30
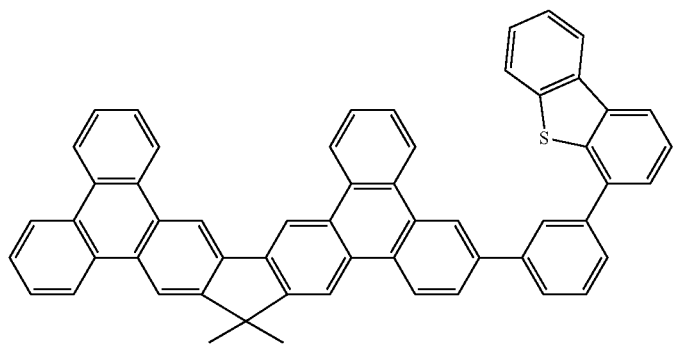

-continued
III-31
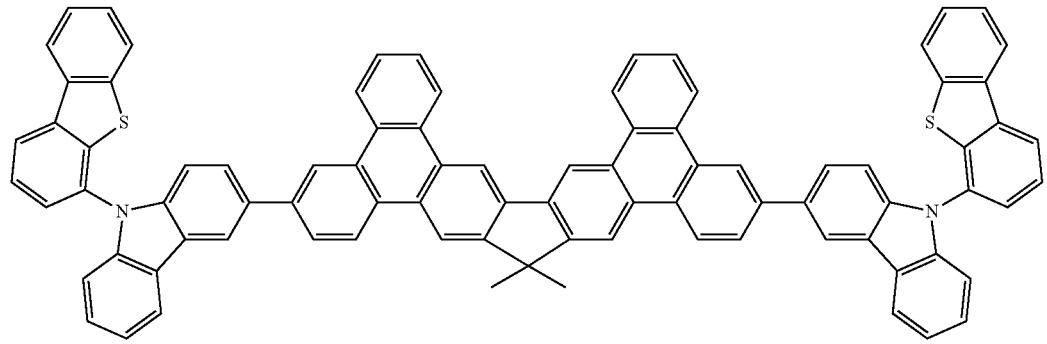
III-32
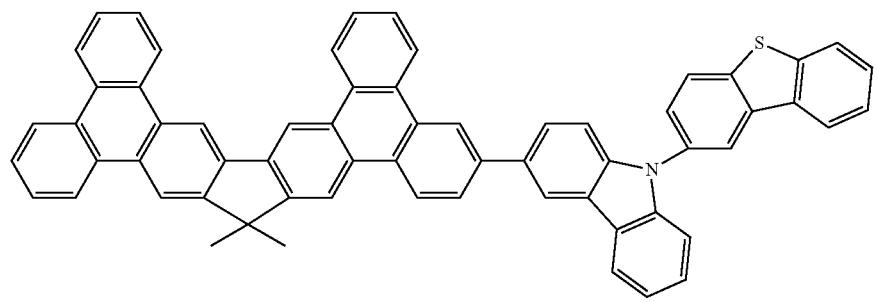
III-33
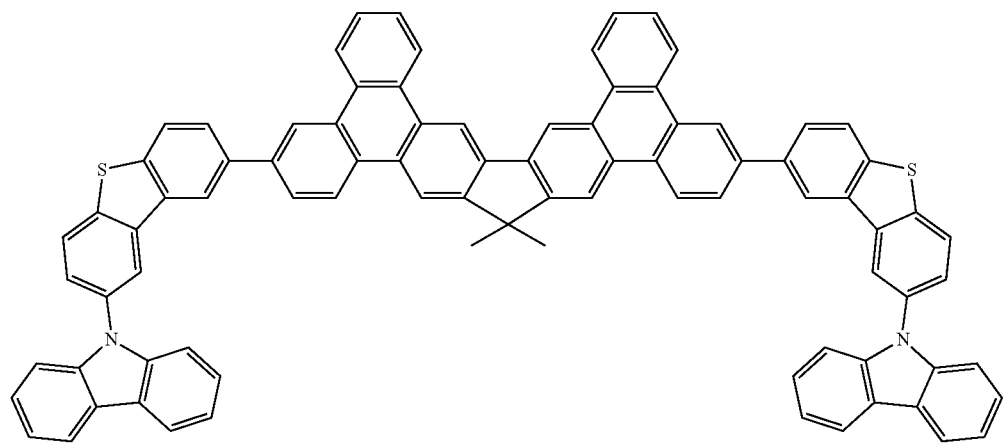
III-34
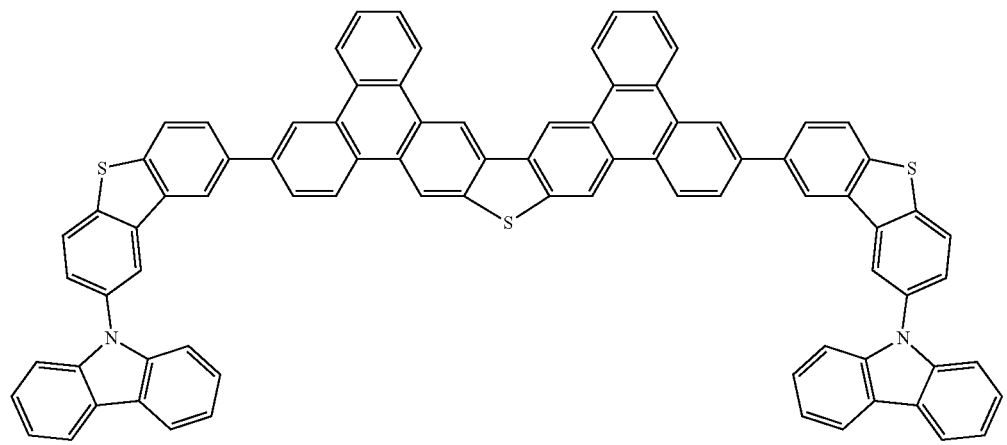

III-35
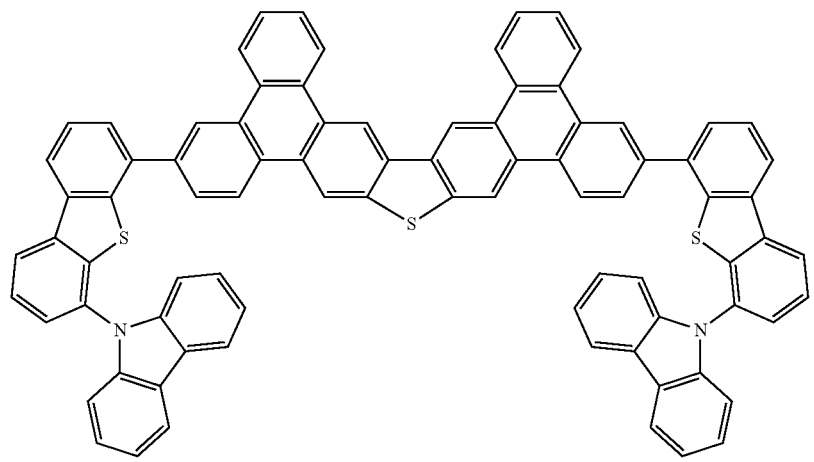
III-36
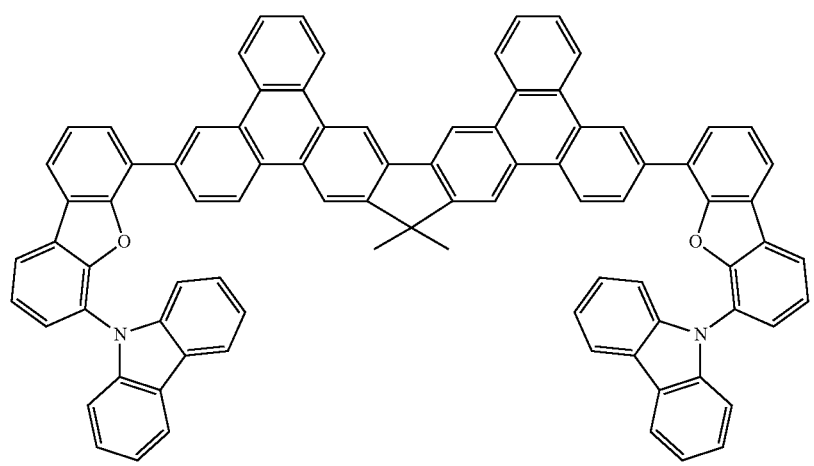
III-37
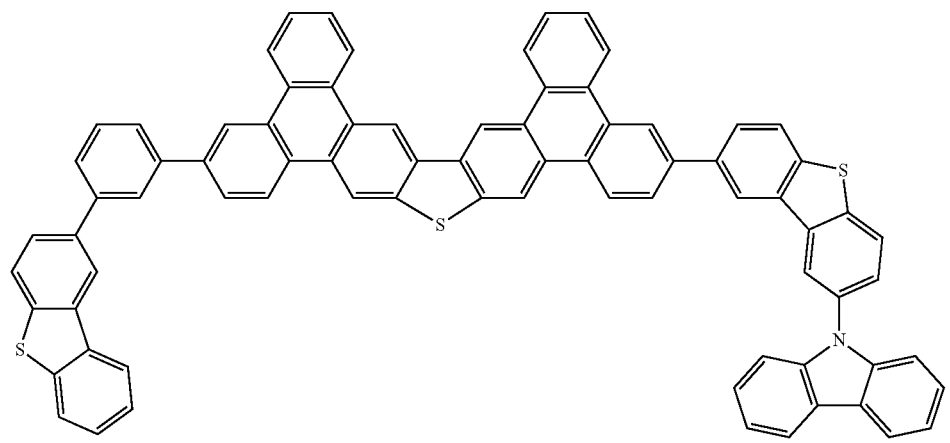

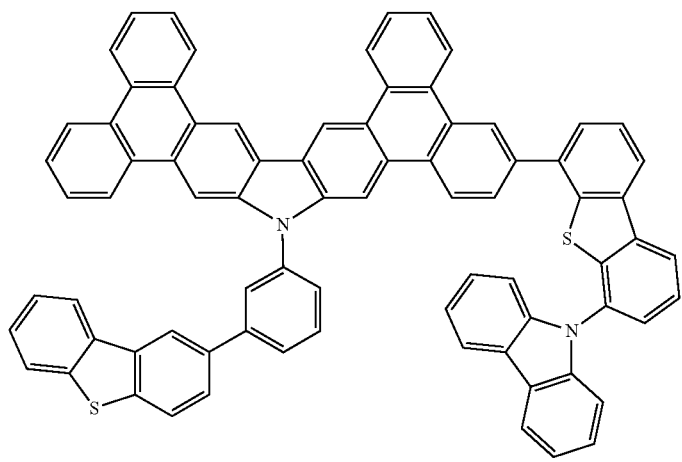
III-38
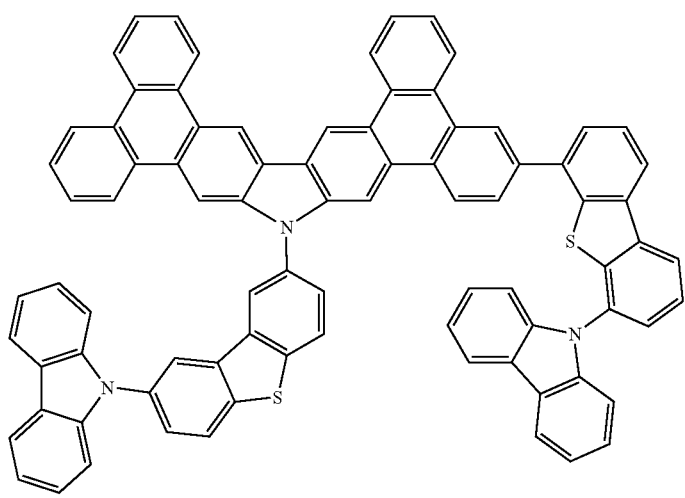
III-39
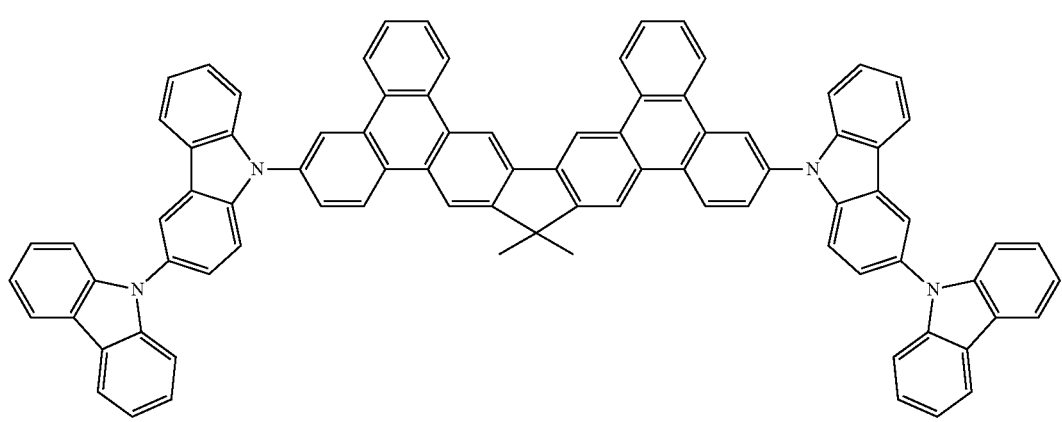
III-40

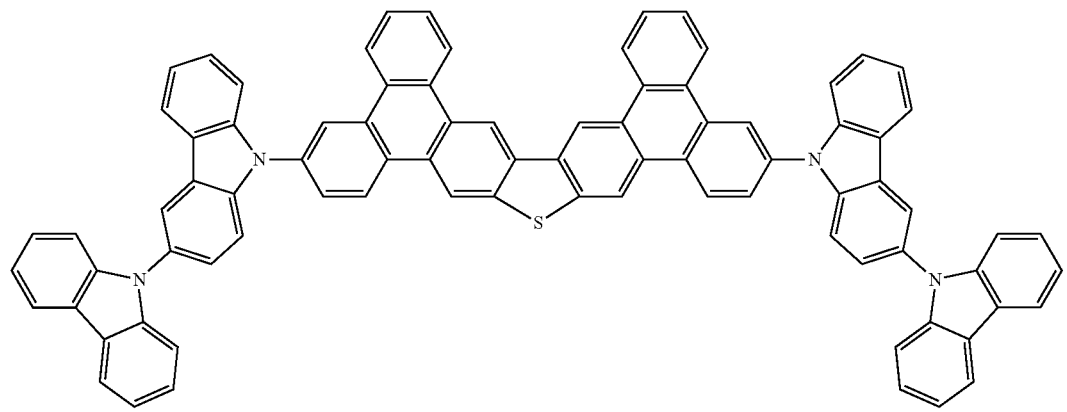
III-41
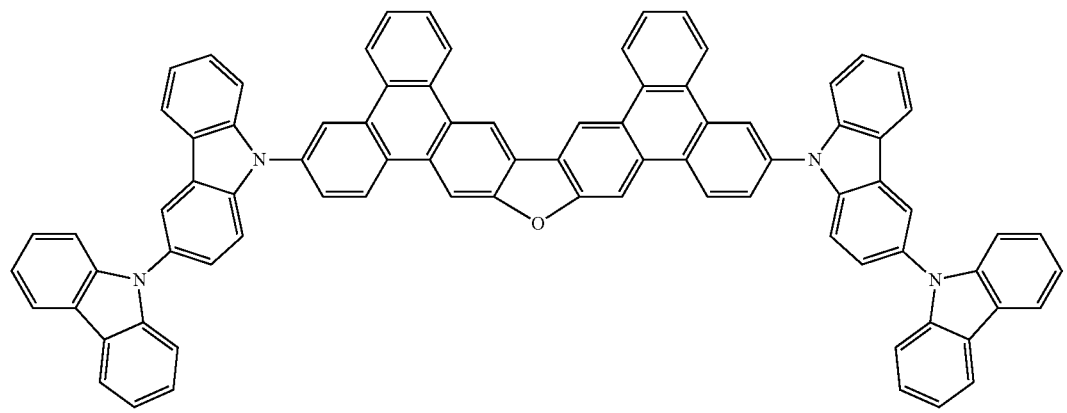
III-42
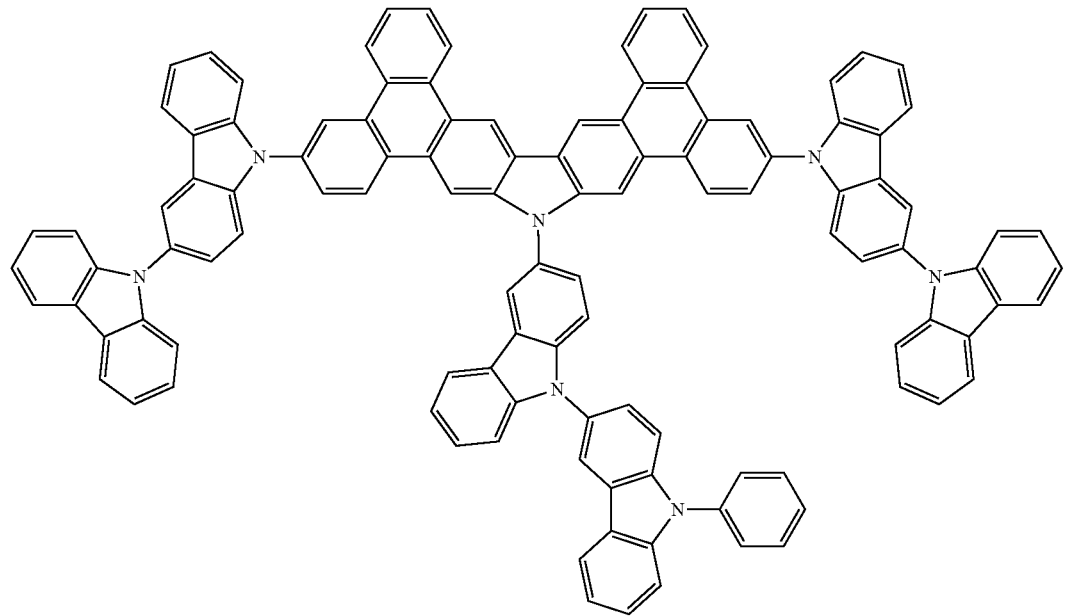
III-43

-continued
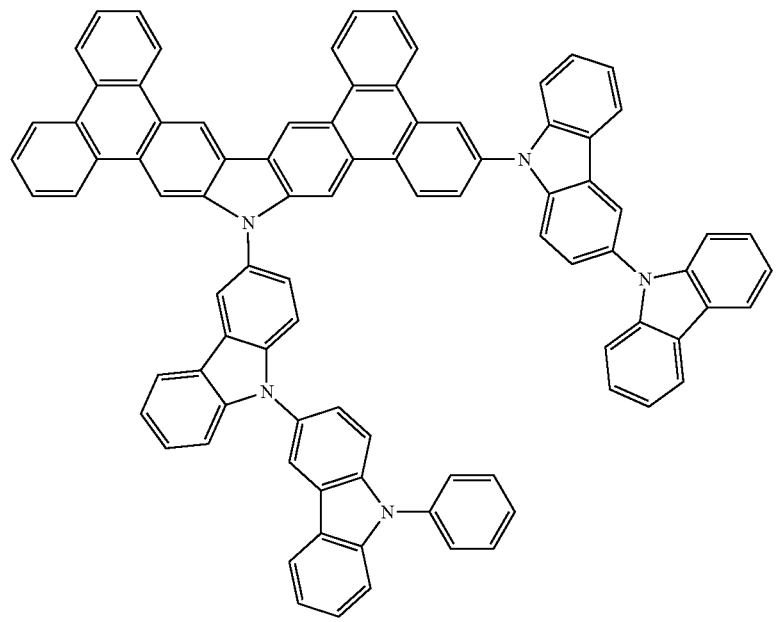
III-44
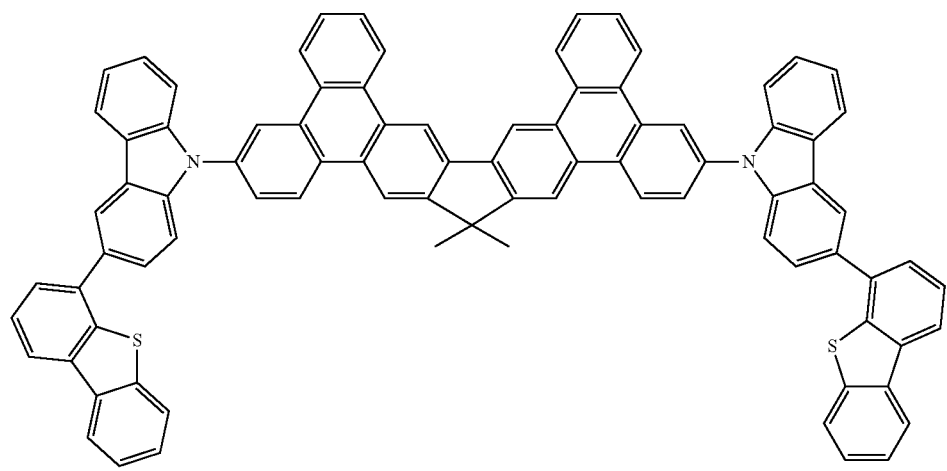
III-45
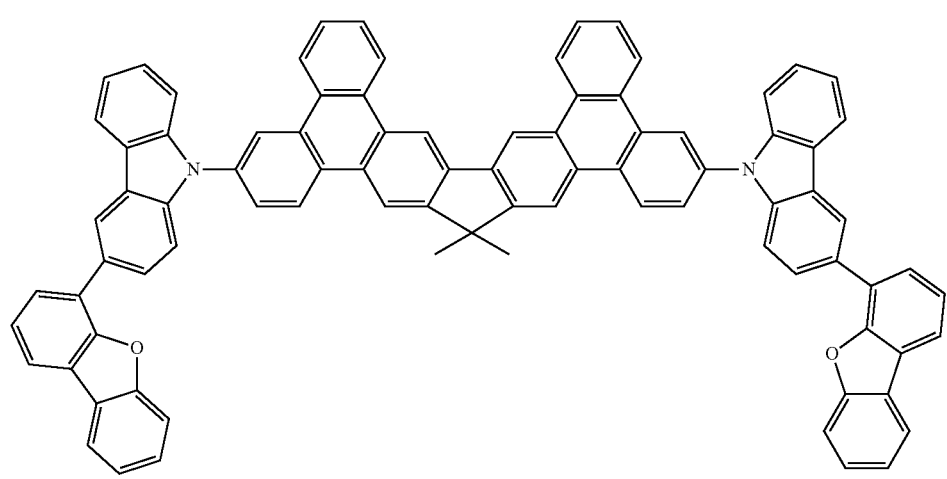
III-46

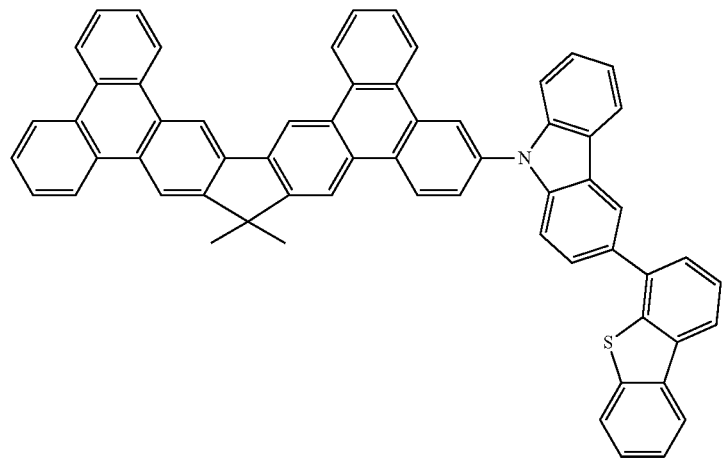
III-47
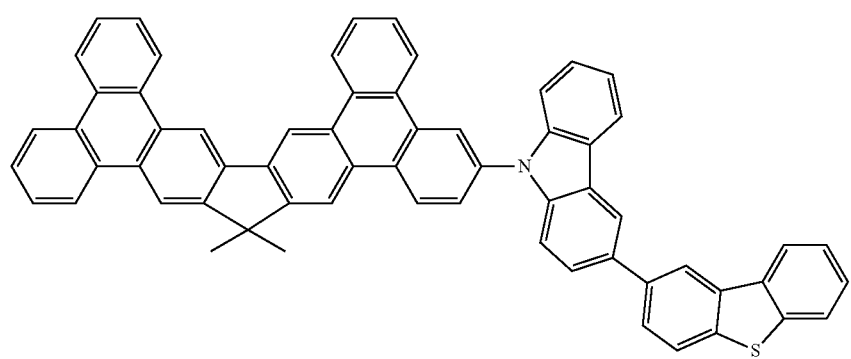
III-48
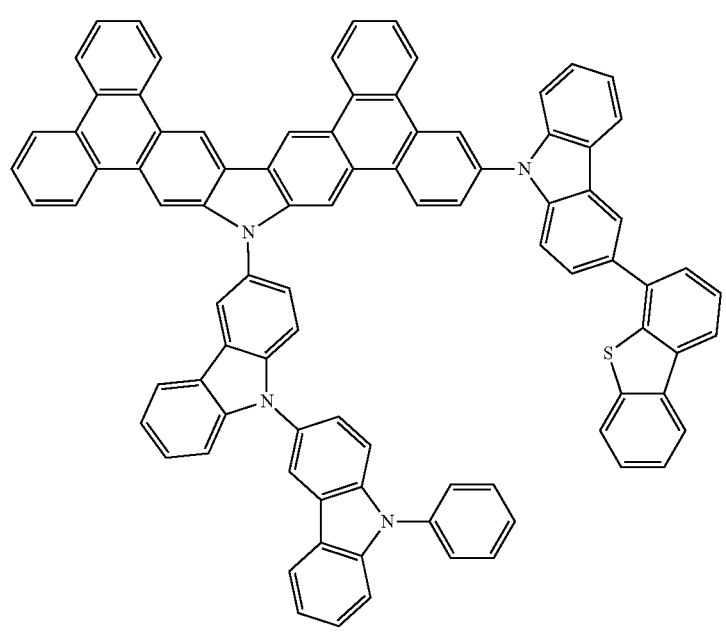
III-49

III-50

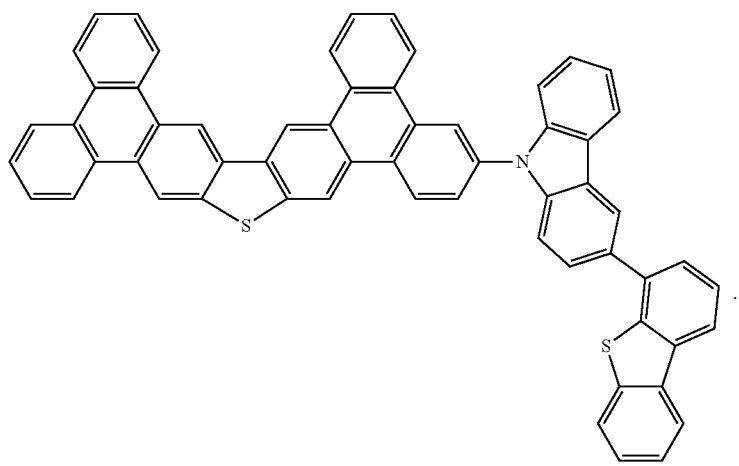

8. A organic EL device comprising a pair of electrodes consisting of a cathode and an anode and between the pairs of electrodes comprising a layer of ditriphenylene derivative with a general formula (I) as follows:

formula(I)

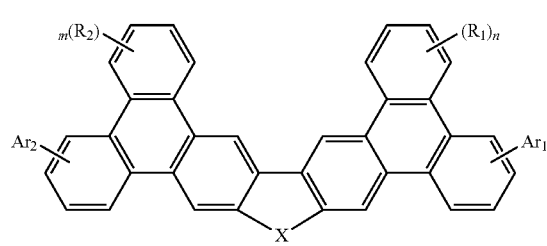

wherein m and n represent an integer of 0 to 10, X is a divalent bridge selected from the atom of group consisting of O, S, C($R_3$)($R_4$), $NR_5$, and Si($R_6$)($R_7$); $Ar_1$ and $Ar_2$ are the same or different, $Ar_1$ and $Ar_2$ represent a hydrogen atom, a halide, a substituted or unsubstituted arylamine group, a substituted or unsubstituted aryl group system having 5 to 60 aromatic ring atoms and each aromatic ring forms a mono or polycyclic ring system, or a substituted or unsubstituted heteroaryl group system having 5 to 60 aromatic ring atoms and each aromatic ring forms a mono or polycyclic ring system, $R_1$ to $R_7$ are identical or different, $R_1$ to $R_7$ are independently selected from the group consisting of a hydrogen atom, alkyl group having 1 to 20 carbon atoms, a substituted or unsubstituted aryl group having 6 to 50 carbon atoms, a substituted or unsubstituted aralkyl group having 6 to 50 carbon atoms, and a substituted or unsubstituted heteroaryl group having 6 to 50 carbon atoms.

9. The organic EL device according to claim 8, wherein the ditriphenylene derivative formula (I) is used as fluorescent host material or dopant material of an emitting layer for an organic EL device is represented by the following formula (II):

formula(II)

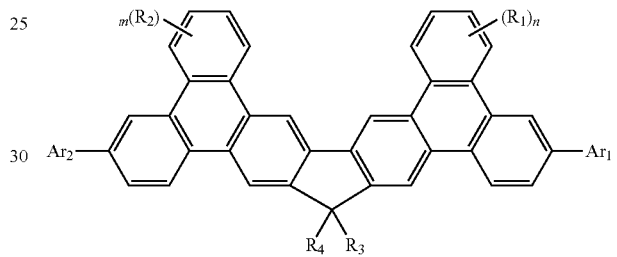

wherein m and n represent an integer of 0 to 10, $Ar_1$ and $Ar_2$ are the same or different, $Ar_1$ and $Ar_2$ represent a hydrogen atom, a halide, a substituted or unsubstituted arylamine group, a substituted or unsubstituted aryl group system having 5 to 60 aromatic ring atoms and each aromatic ring forms a mono or polycyclic ring system, or a substituted or unsubstituted heteroaryl group system having 5 to 60 aromatic ring atoms and each aromatic ring forms a mono or polycyclic ring system, $R_1$ to $R_4$ are identical or different, $R_1$ to $R_4$ are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 6 to 30 carbon atoms.

10. The organic EL device according to claim 8, wherein the ditriphenylene derivative formula (I) is used as phosphorescent host of an emitting layer for an organic EL device is represented by the following formula (III):

formula(III)

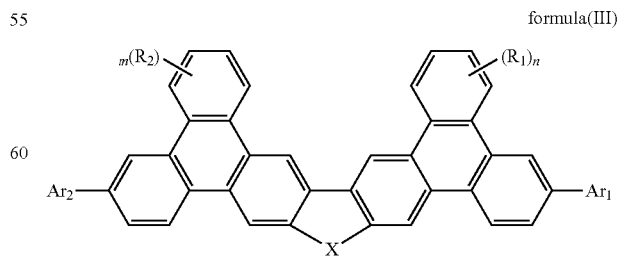

wherein m and n represent an integer of 0 to 10, X is a divalent bridge selected from the atom or group consisting from O, S, NR$_5$; Ar$_1$, Ar$_2$, and R$_5$ are the same or different; Ar$_1$, Ar$_2$, and R$_5$ represent a hydrogen atom, a halide, a substituted or unsubstituted arylamine group, a substituted or unsubstituted aryl group system having 5 to 60 aromatic ring atoms and each aromatic ring forms a mono or polycyclic ring system, or a substituted or unsubstituted heteroaryl group system having 5 to 60 aromatic ring atoms and each aromatic ring forms a mono or polycyclic ring system; R$_1$, R$_2$ are identical or different; R$_1$, R$_2$ are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 6 to 30 carbon atoms.

11. The organic EL device according to claim 9, wherein the formula (I) compound functions as a fluorescent blue emitting dopant of the organic EL device and is selected from compounds represented by following structures:

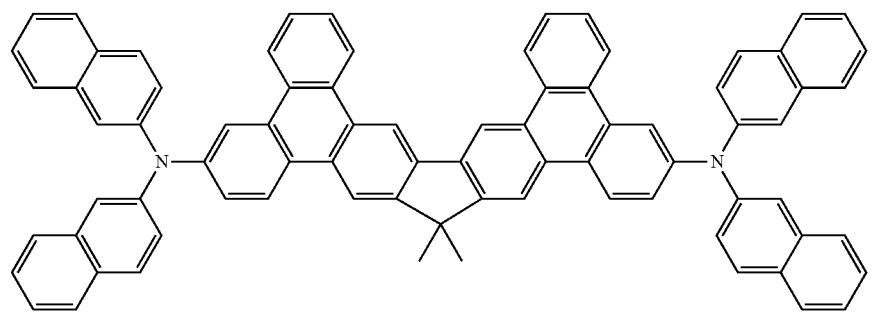

II-7

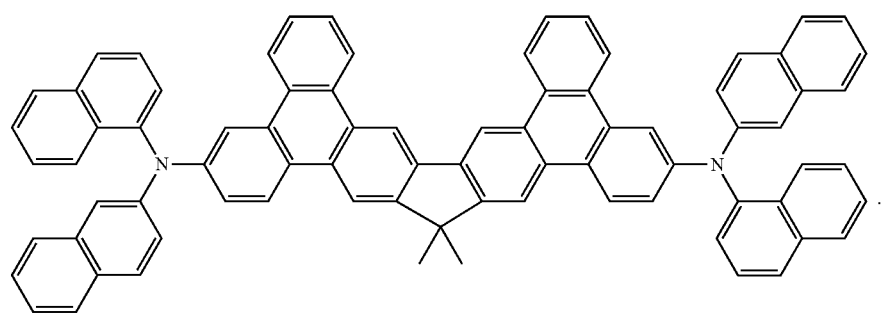

II-8

12. The organic EL device according to claim 9, wherein the formula (I) compound functions as a fluorescent blue emitting host of the organic EL device and is selected from compounds represented by following structures:

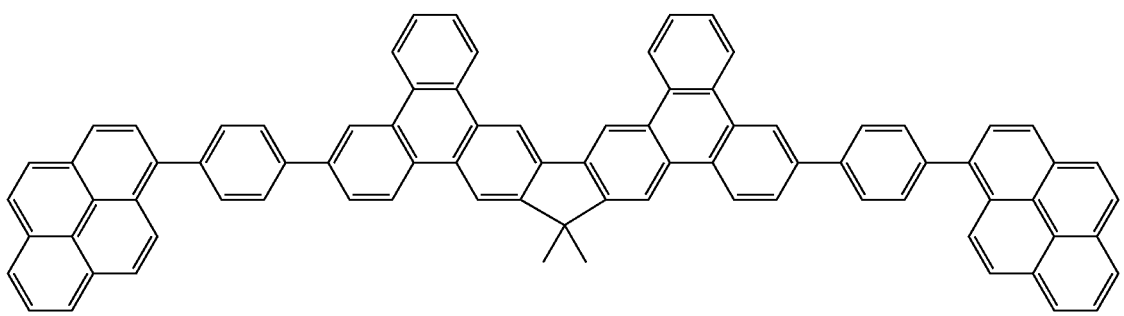

II-27

II-29
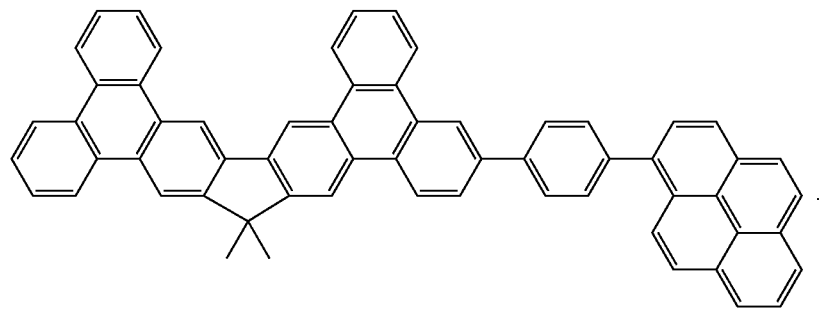
13. The organic EL device according to claim 10, wherein the formula (I) compound functions as a phosphorescent host of the organic EL device and is selected from compounds represented by following structures:
III-8
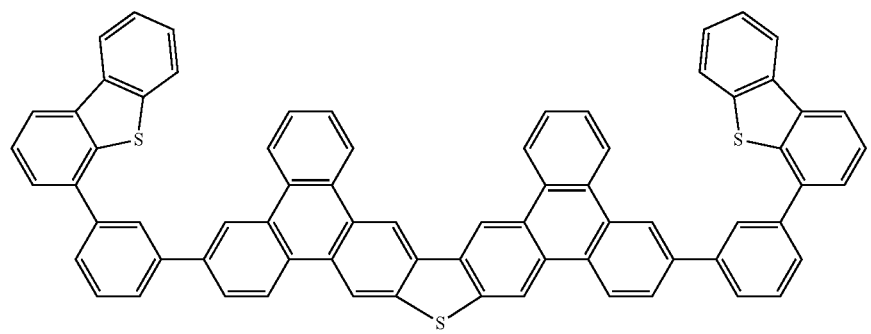
III-29
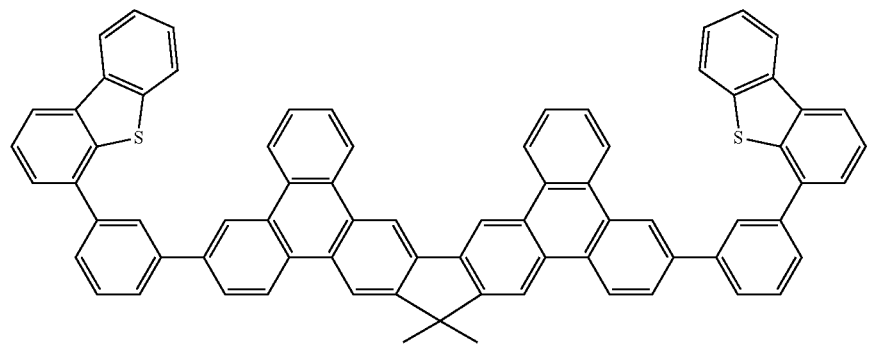
III-30
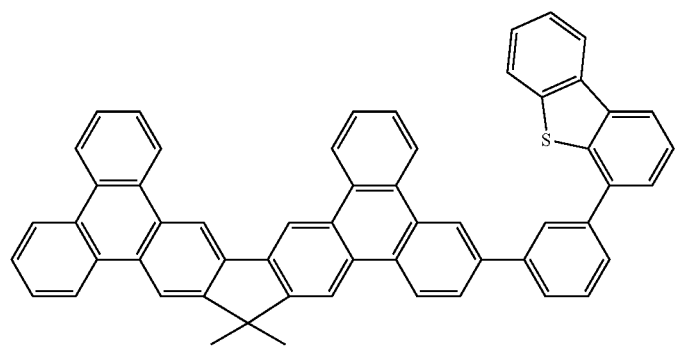

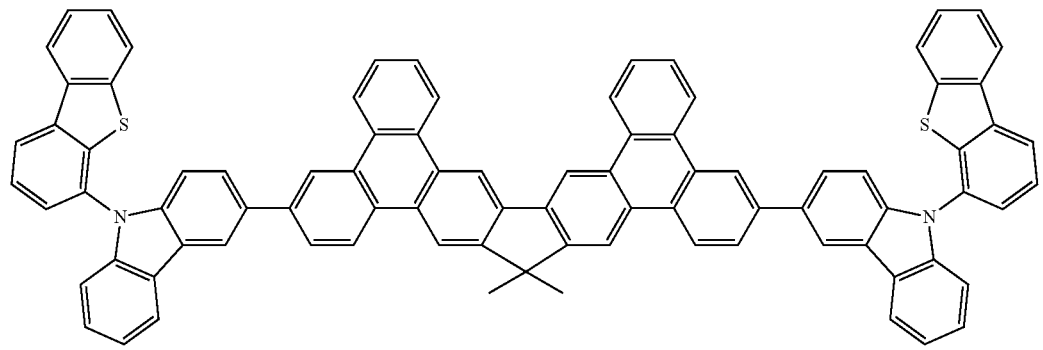
III-31
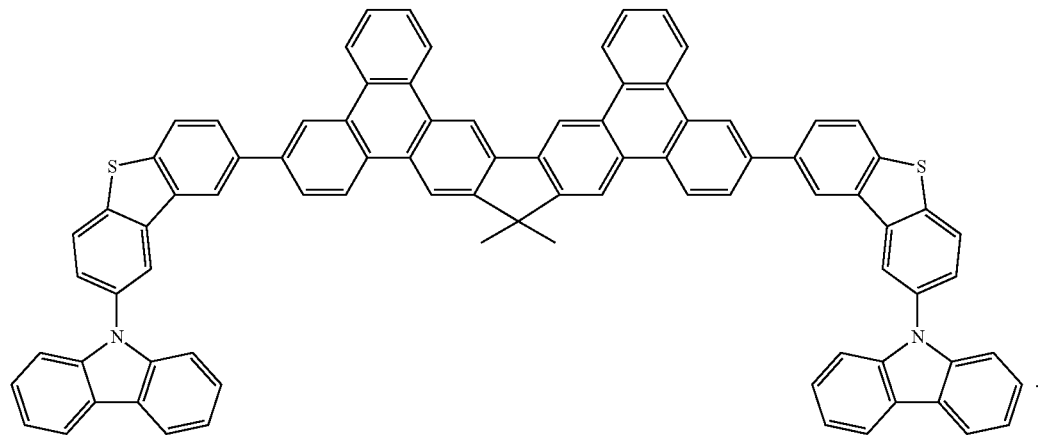
III-33
* * * * *